(12) United States Patent
Kubota et al.

(10) Patent No.: US 7,211,422 B2
(45) Date of Patent: May 1, 2007

(54) POLYPEPTIDE HAVING α-ISOMALTOSYLGLUCOSACCHARIDE SYNTHASE ACTIVITY

(75) Inventors: Michio Kubota, Okayama (JP);
Kazuhiko Maruta, Okayama (JP);
Takuo Yamamoto, Okayama (JP);
Shigeharu Fukuda, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 516 days.

(21) Appl. No.: 10/466,085

(22) PCT Filed: Jan. 9, 2002

(86) PCT No.: PCT/JP02/00052

§ 371 (c)(1),
(2), (4) Date: Jul. 11, 2003

(87) PCT Pub. No.: WO02/055708

PCT Pub. Date: Jul. 18, 2002

(65) Prior Publication Data

US 2004/0161835 A1    Aug. 19, 2004

(30) Foreign Application Priority Data

Jan. 12, 2001   (JP)   ............. 2001-005441

(51) Int. Cl.
*C12N 9/10* (2006.01)
*C12N 1/12* (2006.01)
*C12N 1/15* (2006.01)

(52) U.S. Cl. ............... 435/193; 435/4; 435/6; 435/183; 435/192; 435/252.3; 435/320.1; 536/23.2; 536/23.4; 536/23.5; 536/23.7; 530/350

(58) Field of Classification Search ........ 435/4, 435/6, 69.1, 183, 193, 252.3, 320.1; 536/23.2, 536/23.4, 23.7; 530/350
See application file for complete search history.

(56) References Cited

U.S. PATENT DOCUMENTS

| | | | |
|---|---|---|---|
| 4,521,252 A | 6/1985 | Miyake et al. | |
| 5,889,179 A | 3/1999 | Cote et al. | |
| 2003/0194762 A1 | 10/2003 | Kubota et al. | |
| 2005/0009017 A1 | 1/2005 | Kubota et al. | |

FOREIGN PATENT DOCUMENTS

| EP | 0606753 A2 | 7/1994 |
|---|---|---|
| EP | 0628630 A2 | 12/1994 |
| EP | 1 229 112 A1 | 8/2002 |
| EP | 1 284 286 A1 | 2/2003 |
| EP | 1284286 A1 | 2/2003 |
| GB | 2106912 | 4/1983 |

OTHER PUBLICATIONS

Yeon-Kye Kim et al. (BioSci. Biotechnol. Biochem., 1995, vol. 59(7):1367-1369).*
Aga, H. et al., "Cloning and Sequencing of the Genes Encoding Cyclic Tetrasaccharide-synthesizing Enzymes from *Bacillus globisporus* C11", Bioscience Biotechnology and Biochemistry, (May 2002), vol. 66, No. 5, pp. 1057-1068.
Biely, P. et al., "Purification and properties of alternanase, a novel endo-α-1, 3-60 -1, 6-β-glucanase", European Journal of Biochemistry, (1994), vol. 226, No. 2, pp. 633-639.
Jörk Nölling et al "Genome Sequence and Comparative Analysis of the Solvent-Producing Bacterium Clostridium Acetobutylicum", Journal of Bacteriology, Aug. 2001, vol. 183, No. 16, pp. 4823-4838.
Gregory L. Cote et al "Enzymically produced cyclic α-1,3-linked and α-1,6-linked Oligosaccharides of D-glucose" European Journal of Biochemistry, (1994) vol. 226, pp. 641-648.
Handbook of Amylases and Related Enzymes, Their Sources, Isolation Methods, Properties and Applications (1988) Pergamon Press, Tokyo, Japan.
Dexter French "Studies on the Schardinger Dextrins. The Preparation and Solubility Characteristics of Alpha, Beta and Gamma Dextrins" Journal of the American Chemical Society, (1949) vol. 71, pp. 353-358.

* cited by examiner

*Primary Examiner*—Manjunath Rao
(74) *Attorney, Agent, or Firm*—Browdy and Neimark, PLLC

(57) ABSTRACT

The object of the present invention is to provide a polypeptide which can be used to produce a saccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→}, a DNA encoding the polypeptide, and uses thereof. The present invention solves the above object by establishing a polypeptide which has an enzymatic activity of forming a saccharide with a glucose polymerization degree of 3 or higher and bearing both the α-1,6 glucosidic linkage as a linkage at the non-reducing end and the α-1,4 glucosidic linkage other than the linkage at the non-reducing end from a saccharide with a glucose polymerization degree of 2 or higher and bearing the α-1,4 glucosidic linkage as a linkage at the non-reducing end by α-glucosyl transferring reaction without substantially increasing the reducing power, a DNA encoding the polypeptide, a replicable recombinant DNA comprising the DNA encoding the polypeptide and an autonomously replicable vector, a transformant constructed by introducing the recombinant DNA into an appropriate host, and uses thereof.

10 Claims, 12 Drawing Sheets

SEQUENCE LISTING

<160> NUMBER OF SEQ ID NOS: 32

<210> SEQ ID NO 1
<211> LENGTH: 1249
<212> TYPE: PRT
<213> ORGANISM: Bacillus globisporus C11

<400> SEQUENCE: 1

```
Tyr Val Ser Ser Leu Gly Asn Leu Ile Ser Ser Val Thr Gly Asp
1               5                   10                  15

Thr Leu Thr Leu Thr Val Asp Asn Gly Ala Glu Pro Ser Asp Asp Leu
                20                  25                  30

Leu Ile Val Gln Ala Val Gln Asn Gly Ile Leu Lys Val Asp Tyr Arg
            35                  40                  45

Pro Asn Ser Ile Thr Pro Ser Ala Lys Thr Pro Met Leu Asp Pro Asn
        50                  55                  60

Lys Thr Trp Ser Ala Val Gly Ala Thr Ile Asn Thr Thr Ala Asn Pro
65                  70                  75                  80

Met Thr Ile Thr Thr Ser Asn Met Lys Ile Glu Ile Thr Lys Asn Pro
                85                  90                  95

Val Arg Met Thr Val Lys Lys Ala Asp Gly Thr Thr Leu Phe Trp Glu
                100                 105                 110

Pro Ser Gly Gly Val Phe Ser Asp Gly Val Arg Phe Leu His Ala
            115                 120                 125

Thr Gly Asp Asn Met Tyr Gly Ile Arg Ser Phe Asn Ala Phe Asp Ser
        130                 135                 140

Gly Gly Asp Leu Leu Arg Asn Ser Ser Asn His Ala Ala His Ala Gly
145                 150                 155                 160

Glu Gln Gly Asp Ser Gly Gly Pro Leu Ile Trp Ser Thr Ala Gly Tyr
                165                 170                 175

Gly Leu Leu Val Asp Ser Asp Gly Gly Tyr Pro Tyr Thr Asp Ser Thr
            180                 185                 190

Thr Gly Gln Met Glu Phe Tyr Tyr Gly Gly Thr Pro Pro Glu Gly Arg
        195                 200                 205

Arg Tyr Ala Lys Gln Asn Val Glu Tyr Tyr Ile Met Leu Gly Thr Pro
    210                 215                 220

Lys Glu Ile Met Thr Asp Val Gly Glu Ile Thr Gly Lys Pro Pro Met
225                 230                 235                 240

Leu Pro Lys Trp Ser Leu Gly Phe Met Asn Phe Glu Trp Asp Thr Asn
                245                 250                 255

Gln Thr Glu Phe Thr Asn Asn Val Asp Thr Tyr Arg Ala Lys Asn Ile
            260                 265                 270

Pro Ile Asp Ala Tyr Ala Phe Asp Tyr Asp Trp Lys Lys Tyr Gly Glu
```

-continued

```
                275                 280                 285
Thr Asn Tyr Gly Glu Phe Ala Trp Asn Thr Thr Asn Phe Pro Ser Ala
            290                 295                 300
Ser Thr Thr Ser Leu Lys Ser Thr Met Asp Ala Lys Gly Ile Lys Met
305                 310                 315                 320
Ile Gly Ile Thr Lys Pro Arg Ile Val Thr Lys Asp Ala Ser Ala Asn
                325                 330                 335
Val Thr Thr Gln Gly Thr Asp Ala Thr Asn Gly Gly Tyr Phe Tyr Pro
            340                 345                 350
Gly His Asn Glu Tyr Gln Asp Tyr Phe Ile Pro Val Thr Val Arg Ser
            355                 360                 365
Ile Asp Pro Tyr Asn Ala Asn Glu Arg Ala Trp Phe Trp Asn His Ser
        370                 375                 380
Thr Asp Ala Leu Asn Lys Gly Ile Val Gly Trp Trp Asn Asp Glu Thr
385                 390                 395                 400
Asp Lys Val Ser Ser Gly Gly Ala Leu Tyr Trp Phe Gly Asn Phe Thr
                405                 410                 415
Thr Gly His Met Ser Gln Thr Met Tyr Glu Gly Gly Arg Ala Tyr Thr
            420                 425                 430
Ser Gly Ala Gln Arg Val Trp Gln Thr Ala Arg Thr Phe Tyr Pro Gly
        435                 440                 445
Ala Gln Arg Tyr Ala Thr Thr Leu Trp Ser Gly Asp Ile Gly Ile Gln
    450                 455                 460
Tyr Asn Lys Gly Glu Arg Ile Asn Trp Ala Ala Gly Met Gln Glu Gln
465                 470                 475                 480
Arg Ala Val Met Leu Ser Ser Val Asn Asn Gly Gln Val Lys Trp Gly
                485                 490                 495
Met Asp Thr Gly Gly Phe Asn Gln Gln Asp Gly Thr Thr Asn Asn Pro
            500                 505                 510
Asn Pro Asp Leu Tyr Ala Arg Trp Met Gln Phe Ser Ala Leu Thr Pro
            515                 520                 525
Val Phe Arg Val His Gly Asn Asn His Gln Gln Arg Gln Pro Trp Tyr
    530                 535                 540
Phe Gly Ser Thr Ala Glu Glu Ala Ser Lys Glu Ala Ile Gln Leu Arg
545                 550                 555                 560
Tyr Ser Leu Ile Pro Tyr Met Tyr Ala Tyr Glu Arg Ser Ala Tyr Glu
                565                 570                 575
Asn Gly Asn Gly Leu Val Arg Pro Leu Met Gln Ala Tyr Pro Thr Asp
            580                 585                 590
Ala Ala Val Lys Asn Tyr Thr Asp Ala Trp Met Phe Gly Asp Trp Leu
        595                 600                 605
Leu Ala Ala Pro Val Val Asp Lys Gln Gln Thr Ser Lys Asp Ile Tyr
    610                 615                 620
Leu Pro Ser Gly Ser Trp Ile Asp Tyr Ala Arg Gly Asn Ala Ile Thr
625                 630                 635                 640
Gly Gly Gln Thr Ile Arg Tyr Ser Val Asn Pro Asp Thr Leu Thr Asp
                645                 650                 655
Met Pro Leu Phe Ile Lys Lys Gly Ala Ile Ile Pro Thr Gln Lys Val
            660                 665                 670
Gln Asp Tyr Val Gly Gln Ala Ser Val Thr Ser Val Asp Val Asp Val
        675                 680                 685
Phe Pro Asp Thr Thr Gln Ser Ser Phe Thr Tyr Tyr Asp Asp Asp Gly
    690                 695                 700
```

-continued

```
Ala Ser Tyr Asn Tyr Glu Ser Gly Thr Tyr Phe Lys Gln Asn Met Thr
705                 710                 715                 720

Ala Gln Asp Asn Gly Ser Gly Ser Leu Ser Phe Thr Leu Gly Ala Lys
            725                 730                 735

Ser Gly Ser Tyr Thr Pro Ala Leu Gln Ser Tyr Ile Val Lys Leu His
            740                 745                 750

Gly Ser Ala Gly Thr Ser Val Thr Asn Asn Ser Ala Ala Met Thr Ser
            755                 760                 765

Tyr Ala Ser Leu Glu Ala Leu Lys Ala Ala Ala Gly Glu Gly Trp Ala
770                 775                 780

Thr Gly Lys Asp Ile Tyr Gly Asp Val Thr Tyr Val Lys Val Thr Ala
785                 790                 795                 800

Gly Thr Ala Ser Ser Lys Ser Ile Ala Val Thr Gly Val Ala Ala Val
            805                 810                 815

Ser Ala Thr Thr Ser Gln Tyr Glu Ala Glu Asp Ala Ser Leu Ser Gly
            820                 825                 830

Asn Ser Val Ala Ala Lys Ala Ser Ile Asn Thr Asn His Thr Gly Tyr
            835                 840                 845

Thr Gly Thr Gly Phe Val Asp Gly Leu Gly Asn Asp Gly Ala Gly Val
850                 855                 860

Thr Phe Tyr Pro Lys Val Lys Thr Gly Gly Asp Tyr Asn Val Ser Leu
865                 870                 875                 880

Arg Tyr Ala Asn Ala Ser Gly Thr Ala Lys Ser Val Ser Ile Phe Val
            885                 890                 895

Asn Gly Lys Arg Val Lys Ser Thr Ser Leu Ala Asn Leu Ala Asn Trp
            900                 905                 910

Asp Thr Trp Ser Thr Gln Ser Glu Thr Leu Pro Leu Thr Ala Gly Val
            915                 920                 925

Asn Val Val Thr Tyr Lys Tyr Tyr Ser Asp Ala Gly Asp Thr Gly Asn
930                 935                 940

Val Asn Ile Asp Asn Ile Thr Val Pro Phe Ala Pro Ile Ile Gly Lys
945                 950                 955                 960

Tyr Glu Ala Glu Ser Ala Glu Leu Ser Gly Gly Ser Ser Leu Asn Thr
            965                 970                 975

Asn His Trp Tyr Tyr Ser Gly Thr Ala Phe Val Asp Gly Leu Ser Ala
            980                 985                 990

Val Gly Ala Gln Val Lys Tyr Asn  Val Asn Val Pro Ser  Ala Gly Ser
            995                 1000                1005

Tyr Gln  Val Ala Leu Arg Tyr  Ala Asn Gly Ser Ala  Ala Thr Lys
    1010                1015                1020

Thr Leu  Ser Thr Tyr Ile Asn  Gly Ala Lys Leu Gly  Gln Thr Ser
    1025                1030                1035

Phe Thr  Ser Pro Gly Thr Asn  Trp Asn Val Trp Gln  Asp Asn Val
    1040                1045                1050

Gln Thr  Val Thr Leu Asn Ala  Gly Ala Asn Thr Ile  Ala Phe Lys
    1055                1060                1065

Tyr Asp  Ala Ala Asp Ser Gly  Asn Ile Asn Val Asp  Arg Leu Leu
    1070                1075                1080

Leu Ser  Thr Ser Ala Ala Gly  Thr Pro Val Ser Glu  Gln Asn Leu
    1085                1090                1095

Leu Asp  Asn Pro Gly Phe Glu  Arg Asp Thr Ser Gln  Thr Asn Asn
    1100                1105                1110
```

-continued

```
Trp Ile Glu Trp His Pro Gly Thr Gln Ala Val Ala Phe Gly Val
1115                1120                1125

Asp Ser Gly Ser Thr Thr Asn Pro Pro Glu Ser Pro Trp Ser Gly
    1130                1135                1140

Asp Lys Arg Ala Tyr Phe Phe Ala Ala Gly Ala Tyr Gln Gln Ser
    1145                1150                1155

Ile His Gln Thr Ile Ser Val Pro Val Asn Asn Val Lys Tyr Lys
    1160                1165                1170

Phe Glu Ala Trp Val Arg Met Lys Asn Thr Thr Pro Thr Thr Ala
    1175                1180                1185

Arg Ala Glu Ile Gln Asn Tyr Gly Gly Ser Ala Ile Tyr Ala Asn
    1190                1195                1200

Ile Ser Asn Ser Gly Val Trp Lys Tyr Ile Ser Val Ser Asp Ile
    1205                1210                1215

Met Val Thr Asn Gly Gln Ile Asp Val Gly Phe Tyr Val Asp Ser
    1220                1225                1230

Pro Gly Gly Thr Thr Leu His Ile Asp Asp Val Arg Val Thr Lys
    1235                1240                1245

Gln

<210> SEQ ID NO 2
<211> LENGTH: 1251
<212> TYPE: PRT
<213> ORGANISM: Bacillus globisporus N75

<400> SEQUENCE: 2

His Val Ser Ala Leu Gly Asn Leu Leu Ser Ser Ala Val Thr Gly Asp
1               5                   10                  15

Thr Leu Thr Leu Thr Ile Asp Asn Gly Ala Glu Pro Asn Asp Asp Ile
                20                  25                  30

Leu Val Leu Gln Ala Val Gln Asn Gly Ile Leu Lys Val Asp Tyr Arg
            35                  40                  45

Pro Asn Gly Val Ala Pro Ser Ala Asp Thr Pro Met Leu Asp Pro Asn
        50                  55                  60

Lys Thr Trp Pro Ser Ile Gly Ala Val Ile Asn Thr Ala Ser Asn Pro
65                  70                  75                  80

Met Thr Ile Thr Thr Pro Ala Met Lys Ile Glu Ile Ala Lys Asn Pro
                85                  90                  95

Val Arg Leu Thr Val Lys Lys Pro Asp Gly Thr Ala Leu Leu Trp Glu
            100                 105                 110

Pro Pro Thr Gly Gly Val Phe Ser Asp Gly Val Arg Phe Leu His Gly
        115                 120                 125

Thr Gly Asp Asn Met Tyr Gly Ile Arg Ser Phe Asn Ala Phe Asp Ser
    130                 135                 140

Gly Gly Asp Leu Leu Arg Asn Ser Ser Thr Gln Ala Ala Arg Ala Gly
145                 150                 155                 160

Asp Gln Gly Asn Ser Gly Gly Pro Leu Ile Trp Ser Thr Ala Gly Tyr
                165                 170                 175

Gly Val Leu Val Asp Ser Asp Gly Gly Tyr Pro Phe Thr Asp Glu Ala
            180                 185                 190

Thr Gly Lys Leu Glu Phe Tyr Tyr Gly Gly Thr Pro Pro Glu Gly Arg
        195                 200                 205

Arg Tyr Thr Lys Gln Asp Val Glu Tyr Tyr Ile Met Leu Gly Thr Pro
    210                 215                 220
```

-continued

```
Lys Glu Ile Met Ser Gly Val Gly Glu Ile Thr Gly Lys Pro Pro Met
225                 230                 235                 240

Leu Pro Lys Trp Ser Leu Gly Phe Met Asn Phe Glu Trp Asp Leu Asn
            245                 250                 255

Glu Ala Glu Leu Lys Asn His Val Asp Thr Tyr Arg Ala Lys Asn Ile
        260                 265                 270

Pro Ile Asp Gly Tyr Ala Ile Asp Phe Asp Trp Lys Lys Tyr Gly Glu
    275                 280                 285

Asn Asn Tyr Gly Glu Phe Ala Trp Asn Thr Ala Asn Phe Pro Ser Ala
290                 295                 300

Ala Thr Thr Ala Leu Lys Ser Gln Met Asp Ala Lys Gly Ile Lys Met
305                 310                 315                 320

Ile Gly Ile Thr Lys Pro Arg Ile Ala Thr Lys Asp Phe Ser Asn Asn
            325                 330                 335

Pro Thr Val Gln Gly Thr Asp Ala Ala Ser Gly Gly Tyr Phe Tyr Pro
        340                 345                 350

Gly His Ser Glu Tyr Lys Asp Tyr Phe Ile Pro Val Phe Val Arg Ser
    355                 360                 365

Ile Asp Pro Tyr Asn Pro Ala Ala Arg Ser Trp Phe Trp Asn His Ser
370                 375                 380

Lys Asp Ala Phe Asp Lys Gly Ile Val Gly Trp Trp Asn Asp Glu Thr
385                 390                 395                 400

Asp Ala Val Ser Ser Gly Gly Ala Ser Tyr Trp Phe Gly Asn Phe Thr
            405                 410                 415

Thr Gly His Met Ser Gln Ala Leu Tyr Glu Gly Gln Arg Ala Tyr Thr
        420                 425                 430

Ser Asn Ala Gln Arg Val Trp Gln Thr Ala Arg Thr Phe Tyr Pro Gly
    435                 440                 445

Ala Gln Arg Tyr Ala Thr Thr Leu Trp Ser Gly Asp Ile Gly Ile Gln
450                 455                 460

Tyr Thr Lys Gly Glu Arg Ile Asn Trp Ala Ala Gly Met Gln Glu Gln
465                 470                 475                 480

Arg Ala Val Met Leu Ser Ser Ile Asn Asn Gly Gln Val Lys Trp Gly
            485                 490                 495

Met Asp Thr Gly Gly Phe Asn Gln Gln Asp Gly Thr Thr Asn Asn Pro
        500                 505                 510

Asn Pro Asp Leu Tyr Ala Arg Trp Met Gln Phe Ser Ala Leu Thr Pro
    515                 520                 525

Val Phe Arg Val His Gly Asn Asn His Gln Gln Arg Gln Pro Trp Tyr
530                 535                 540

Tyr Gly Ser Thr Ala Glu Glu Ala Ser Lys Glu Ala Leu Gln Leu Arg
545                 550                 555                 560

Tyr Ser Leu Ile Pro Tyr Met Tyr Ala Tyr Glu Arg Ser Ala Tyr Glu
            565                 570                 575

Asn Gly Asn Gly Leu Val Arg Pro Leu Met Gln Glu Tyr Pro Ala Asp
        580                 585                 590

Ala Asn Ala Lys Asn Tyr Leu Asp Ala Trp Met Phe Gly Asp Trp Leu
    595                 600                 605

Leu Ala Ala Pro Val Val Glu Lys Gln Gln Thr Ser Lys Glu Ile Tyr
610                 615                 620

Leu Pro Ala Gly Thr Trp Ile Asp Tyr Asn Arg Gly Thr Val Leu Thr
625                 630                 635                 640

Gly Gly Gln Lys Ile Ser Tyr Ala Val Asn Pro Asp Thr Leu Thr Asp
```

-continued

```
                645                 650                 655
Ile Pro Leu Phe Ile Lys Lys Gly Ala Ile Pro Ser Gln Lys Val
            660                 665                 670
Gln Asp Tyr Val Gly Gln Ala Pro Val Gln Thr Val Asp Val Asp Val
            675                 680                 685
Phe Pro Asn Thr Ala Gln Ser Ser Phe Thr Tyr Tyr Asp Asp Asp Gly
690                 695                 700
Ser Ser Tyr Asn Tyr Glu Ser Gly Ala Tyr Phe Lys Gln Leu Met Thr
705                 710                 715                 720
Ala Gln Asp Asn Gly Ser Gly Ala Leu Ser Phe Thr Leu Gly Ala Lys
            725                 730                 735
Thr Gly Thr Tyr Ser Pro Ala Leu Gln Ser Tyr Ile Val Lys Leu His
            740                 745                 750
Gly Ala Gly Ala Ser Val Thr Ser Asn Gly Ala Ala Leu Ala Ser
            755                 760                 765
Tyr Ala Ser Leu Gln Ala Leu Lys Ala Ser Ala Ser Glu Gly Trp Ala
            770                 775                 780
Lys Gly Lys Asp Ile Tyr Gly Asp Val Thr Tyr Val Lys Leu Ser Ala
785                 790                 795                 800
Gly Ala Ala Ala Lys Ala Ile Ala Val Thr Gly Asn Ser Pro Val
            805                 810                 815
Ser Val Ala Asp Val Gln Tyr Glu Ala Glu Ala Ser Leu Ser Gly
            820                 825                 830
Asn Thr Thr Ala Thr Lys Ala Thr Val Asn Thr Asn His Ala Gly Tyr
            835                 840                 845
Thr Gly Ser Gly Phe Val Asp Gly Leu Ser Asn Pro Gly Ala Ala Val
            850                 855                 860
Thr Phe Tyr Pro Lys Val Lys Thr Gly Gly Asp Tyr Asn Val Ser Leu
865                 870                 875                 880
Arg Tyr Ala Asn Ser Thr Gly Ala Ala Lys Ser Val Ser Ile Phe Val
            885                 890                 895
Asn Gly Lys Arg Val Lys Ser Thr Ser Leu Ala Asn Leu Pro Asn Trp
            900                 905                 910
Asp Thr Trp Gly Thr Gln Ala Glu Thr Leu Pro Leu Thr Ala Gly Thr
            915                 920                 925
Asn Val Val Thr Tyr Lys Phe Tyr Ser Asp Ala Gly Asp Thr Gly Ser
930                 935                 940
Val Asn Leu Asp Asn Ile Thr Val Pro Phe Ala Pro Ile Gly Lys
945                 950                 955                 960
Tyr Glu Ala Glu Ser Ala Glu Leu Ser Gly Gly Ser Thr Val Asn Gln
            965                 970                 975
Asn His Trp Phe Tyr Ser Gly Thr Ala Phe Val Asp Gly Leu Thr Ala
            980                 985                 990
Pro Gly Ala Gln Val Lys Tyr Thr  Val Asn Ala Pro Ala  Ala Gly Ser
            995                 1000                1005
Tyr Gln  Ile Ala Leu Arg Tyr  Ala Asn Gly Thr Gly  Ala Ala Lys
1010                1015                1020
Thr Leu  Ser Thr Tyr Val Asn  Gly Thr Lys Leu Gly  Gln Thr Ala
1025                1030                1035
Phe Ala  Ser Pro Gly Gly Asn  Trp Asn Val Trp Gln  Asp Ser Val
1040                1045                1050
Gln Thr  Val Ala Leu Ala Ala  Gly Thr Asn Thr Ile  Ala Phe Lys
1055                1060                1065
```

-continued

```
Tyr Asp Ala Gly Asp Ser Gly Ser Gly Ser Val Asn Leu Asp Arg
    1070            1075            1080

Leu Leu Leu Ser Ala Ala Ala Pro Gly Val Pro Val Ser Glu Gln
    1085            1090            1095

Asn Leu Leu Asp Asn Gly Gly Phe Glu Arg Asp Pro Ser Gln Ser
    1100            1105            1110

Ser Asn Trp Thr Glu Trp His Pro Ala Ser Gln Ala Ile Ala Tyr
    1115            1120            1125

Gly Ile Asp Ser Gly Ser Gly Met Asn Pro Pro Glu Ser Pro Trp
    1130            1135            1140

Ala Gly Asp Lys Arg Ala Tyr Phe Tyr Ala Ala Gly Pro Tyr Gln
    1145            1150            1155

Gln Ser Ile His Gln Thr Val Ser Val Pro Val Asn Asn Ala Lys
    1160            1165            1170

Tyr Lys Phe Glu Ala Trp Val Leu Leu Lys Asn Thr Thr Pro Thr
    1175            1180            1185

Thr Ala Arg Val Glu Ile Gln Asn Tyr Gly Gly Ser Pro Ile Phe
    1190            1195            1200

Thr Asn Ile Ser Lys Asp Gly Val Trp Lys Tyr Ile Ser Val Ser
    1205            1210            1215

Asp Ile Gln Val Thr Asn Gly Gln Ile Asp Ile Gly Phe Tyr Val
    1220            1225            1230

Asp Ser Pro Gly Gly Thr Thr Leu His Ile Asp Asp Val Arg Val
    1235            1240            1245

Thr Lys Gln
    1250

<210> SEQ ID NO 3
<211> LENGTH: 929
<212> TYPE: PRT
<213> ORGANISM: Arthrobacter globiformis A19

<400> SEQUENCE: 3

Ala Pro Leu Gly Val Gln Arg Ala Gln Phe Gln Ser Gly Ser Ser Tyr
1               5                   10                  15

Leu Val Val Glu Val Leu Asp Asp Leu Val His Phe Glu Leu Ala
            20                  25                  30

Gly Gly Gly Thr Ala Pro Gly Thr Gly Ser Pro Leu Phe Thr Thr Pro
        35                  40                  45

Gln Val Ala Lys His Asp Tyr Ala Gly Pro Asp Val Phe Thr Gln Thr
    50                  55                  60

Gly Ser Val Leu Gln Thr Ala Ala Met Arg Ile Glu Val Asp Pro Ala
65                  70                  75                  80

Asp Leu Cys Val Thr Ala Thr Asp Ile Thr Arg Thr Pro Asn Leu Val
                85                  90                  95

Leu His Glu Ala Cys Pro Ala Asp Leu Gly Gln Ala Trp Lys Gly Leu
            100                 105                 110

Asn Ile Thr Arg Ser Ala Met Glu Asn Ala Tyr Gly Leu Gly Gln Gln
        115                 120                 125

Phe Phe Thr Gly Gly Ser Ala Asp Gly Asp Trp Val Gly Arg Thr Arg
    130                 135                 140

Thr Pro Gly Gly Thr Tyr Gly Asn Ala Met Val Phe Asp Pro Glu Asn
145                 150                 155                 160

Gly Pro Val Gly Asn Thr Gln Ile Pro Val Leu Phe Ala Val Gly Asp
```

-continued

```
                     165                 170                 175
Asp Asn Ala Asn Tyr Gly Leu Phe Val Asp Gln Leu Tyr Lys Gln Glu
                180                 185                 190
Trp Asn Leu Thr Gly Asp Pro Trp Thr Val Arg Met Trp Gly Asp Gln
            195                 200                 205
Val Arg Trp Tyr Leu Met Ser Gly Asp Asp Leu Pro Asp Leu Arg His
210                 215                 220
Asp Tyr Met Glu Leu Thr Gly Thr Pro Val Pro Pro Lys Lys Ala
225                 230                 235                 240
Phe Gly Leu Trp Val Ser Glu Phe Gly Tyr Asp Asn Trp Ser Glu Val
                245                 250                 255
Asp Asn Thr Ile Ala Gly Leu Arg Ser Ala Asp Phe Pro Val Asp Gly
            260                 265                 270
Ala Met Leu Asp Val Gln Trp Phe Gly Gly Val Thr Ala Asp Ser Asp
        275                 280                 285
Asp Thr Arg Met Gly Thr Leu Asp Trp Asp Thr Ser Arg Phe Pro Asp
    290                 295                 300
Pro Ala Gly Lys Ile Ala Asp Leu Ala Glu Asp Gly Val Gly Ile Ile
305                 310                 315                 320
Pro Ile Glu Glu Ser Tyr Val Gly Arg Asn Leu Pro Glu His Ala Arg
                325                 330                 335
Met Ala Ala Asp Gly Tyr Leu Val Arg Ser Gly Cys Ala Thr Cys Pro
            340                 345                 350
Pro Val Tyr Leu Thr Gly Asn Pro Trp Trp Gly Lys Gly Met Ile
        355                 360                 365
Asp Trp Thr Gln Pro Glu Ala Gly Ala Val Trp His Asp Glu Gln Arg
    370                 375                 380
Gln His Leu Val Asp Glu Gly Val Leu Gly His Trp Leu Asp Leu Gly
385                 390                 395                 400
Glu Pro Glu Met Tyr Asp Pro Asn Asp Trp Thr Ala Gly Val Ile Pro
                405                 410                 415
Gly Lys His Ala His Ala Asp Tyr His Asn Ala Tyr Asn Leu Leu Trp
            420                 425                 430
Ala Gln Ser Ile Ala Asp Gly Tyr Ala Asp Asn Gly Val Gln Lys Arg
        435                 440                 445
Pro Phe Met Leu Thr Arg Ala Ala Ala Gly Ile Gln Arg His Gly
    450                 455                 460
Ala Gly Met Trp Ser Ala Asp Ile Gly Ser Thr Met Lys Ala Leu Gly
465                 470                 475                 480
Ser Gln Gln Asn Ala Gln Met His Met Ser Met Ser Gly Ile Asp Tyr
                485                 490                 495
Tyr Gly Ser Asp Ile Gly Gly Phe Arg Arg Glu Met Ala Asp Gly Asp
            500                 505                 510
Val Asn Glu Leu Tyr Thr Gln Trp Phe Ala Asp Ser Ala Trp Phe Asp
        515                 520                 525
Thr Pro Leu Arg Pro His Thr Asp Asn Leu Cys Asn Cys Leu Glu Thr
    530                 535                 540
Ser Pro Asp Ser Ile Gly Asp Val Ala Ser Asn Arg Glu Asn Leu Val
545                 550                 555                 560
Arg Arg Tyr Glu Leu Ala Pro Tyr Tyr Ser Leu Ala His Arg Ala
                565                 570                 575
His Gln Phe Gly Glu Pro Leu Ala Pro Pro Leu Val Tyr Tyr Gln
            580                 585                 590
```

-continued

```
Asn Asp Asp His Val Arg Glu Met Gly His Gln Lys Met Leu Gly Arg
        595                 600                 605
Asp Leu Leu Ile Ala Ile Val Ala Gly Glu Gly Arg Glu Arg Asp
    610                 615                 620
Val Tyr Leu Pro Ala Gly Glu Trp Ile Asp Ile His Thr Asn Glu Arg
625                 630                 635                 640
Ile Gln Ser Thr Gly Gln Trp Ile Asp Asn Val Pro Leu Trp Arg Asp
                645                 650                 655
Gly Val Phe Thr Leu Pro Ala Tyr Ala Arg Ala Gly Ala Ile Ile Pro
                660                 665                 670
Lys Ala Phe Val Asp Ala Ser Thr Lys Asp Ile Thr Gly Lys Arg Glu
            675                 680                 685
Asp Ala Val Arg Asn Glu Leu Ile Ala Thr Val Tyr Ala Asp Asp
        690                 695                 700
Val Ala Ser Asp Phe Thr Leu Tyr Glu Asp Asp Gly Ala Thr Thr Ala
705                 710                 715                 720
Tyr Ala Asp Gly Ala Val Arg Thr Thr Gln Ile Ser Gln Ser Leu Thr
                725                 730                 735
Asn Gly Val Ala Thr Val Thr Val Gly Ala Ala Ser Gly Thr Tyr Ser
                740                 745                 750
Gly Ala Pro Ser Thr Arg Pro Thr Val Val Glu Leu Val Thr Asp Gly
                755                 760                 765
Thr Gln Ala Ser Thr Val Ser Leu Gly Ser Val Pro Leu Thr Glu His
    770                 775                 780
Ala Asn Lys Ala Ala Phe Asp Ala Ala Ser Ser Gly Trp Tyr Asn Ala
785                 790                 795                 800
Gly Gly Gly Leu Val Val Ala Lys Ala Ser Ser Val Asn Thr
                805                 810                 815
Ala Lys Thr Phe Ser Phe Thr Leu Gly Glu Glu Ser Val Trp Ala Thr
                820                 825                 830
Phe Ser Cys Glu Asn Ala Thr Thr Thr Phe Gly Gln Ser Val Tyr Val
                835                 840                 845
Val Gly Asn Val Pro Gln Leu Gly Asn Trp Ser Pro Ala Asp Ala Val
850                 855                 860
Lys Leu Glu Pro Ser Ala Tyr Pro Thr Trp Thr Gly Val Val Arg Asn
865                 870                 875                 880
Leu Pro Pro Ser Ser Thr Val Glu Trp Lys Cys Ile Lys Arg Gln Glu
                885                 890                 895
Ala Gly Leu Pro Asn Thr Ala Asp Ala Trp Glu Pro Gly Gly Asn Asn
                900                 905                 910
Ile Leu Ser Thr Pro Pro Ser Gly Ser Ala Gly Ile Thr Thr Gly Ala
            915                 920                 925
Phe
```

<210> SEQ ID NO 4
<211> LENGTH: 3747
<212> TYPE: DNA
<213> ORGANISM: Bacillus globisporus C11

<400> SEQUENCE: 4

| tatgtcagca gcctaggaaa tctcatttct tcgagtgtca ccggagatac cttgacgcta | 60 |
| actgttgata acggtgcgga gccgagtgat gacctcttga ttgttcaagc ggtgcaaaac | 120 |
| ggtattttga aggtggatta tcgtccaaat agcataacgc cgagcgcgaa gacgccgatg | 180 |

-continued

```
ctggatccga acaaaacttg gtcagctgta ggagctacga ttaatacgac agccaatcca    240
atgaccatca cgacttccaa tatgaagatt gagattacca agaatccagt acgaatgacg    300
gtcaagaagg cggacggcac tacgctattc tgggaaccat caggcggagg ggtattctca    360
gacggtgtgc gcttccttca tgccacaggg gataatatgt atggcatccg gagcttcaat    420
gcttttgata gcggggtgga cctgctgcgg aattcgtcca atcatgccgc ccatgcgggt    480
gaacagggag attccggtgg tccgcttatt tggagtacgg caggatatgg actattagtc    540
gatagcgatg gcggctaccc ctatacagat agcacaaccg gtcaaatgga gttttattat    600
ggtgggaccc ctcctgaggg acgtcgttat gcgaaacaaa acgtggaata ttatattatg    660
ctcggaaccc ccaaggaaat tatgaccgac gtaggggaaa tcacagggaa accgcctatg    720
ctgcctaagt ggtcgcttgg attcatgaac tttgagtggg atacgaatca aacggagttt    780
acgaataatg tggatacgta tcgtgccaaa aatatcccca tagatgctta cgccttcgac    840
tatgactgga aaagtacggg ggaaaccaac tatggtgaat tcgcgtggaa tacgactaat    900
ttcccttctg cgtcaacgac ttctttaaag tcaacaatgg atgctaaagg catcaaaatg    960
atcggaatta caaaaccccg catcgttacg aaggatgctt cagcgaatgt gacgacccaa   1020
gggacggacg cgacaaatgg cggttatttt tatccaggcc ataacgagta tcaggattat   1080
ttcattcccg taactgtgcg tagtatcgat ccttacaatg ctaacgaacg tgcttggttc   1140
tggaatcatt ccacagatgc gcttaataaa gggatcgtag gttggtggaa tgacgagacg   1200
gataaagtat cttcgggtgg agcgttatat tggtttggca atttcacaac aggccacatg   1260
tctcagacga tgtacgaagg ggggcgggct tacacgagtg gagcgcagcg tgtttggcaa   1320
acggctagaa ccttctaccc agtgcccagc ggtatgcga ctacgctttg gtctggcgat   1380
attggcattc aatacaataa aggcgaacgg atcaattggg ctgccgggat gcaggagcaa   1440
agggcagtta tgctatcctc cgtgaacaat ggccaggtga atggggcat ggataccggc   1500
ggattcaatc agcaggatgg cacgacgaac aatccgaatc ccgatttata cgctcggtgg   1560
atgcagttca gtgccctaac gcctgttttc cgagtgcatg ggaacaacca tcagcagcgc   1620
cagccatggt acttcggatc gactgcggag gaggcctcca agaggcaat tcagctgcgg   1680
tactccctga tcccttatat gtatgcctat gagagaagtg cttacgagaa tgggaatggg   1740
ctcgttcggc cattgatgca agcctatcca acagatgcgg ccgtcaaaaa ttacacggat   1800
gcttggatgt tggtgactg gctgctggct gcacctgtgg tagataaaca gcagacgagt   1860
aaggatatct atttaccgtc tgggtcatgg attgactatg cgcgaggcaa tgcaataact   1920
ggcggtcaaa ccatccgata ttcggttaat ccggacacgt tgacagacat gcctctcttt   1980
attaaaaaag gtgccattat tccaacacag aaagtgcagg attacgtagg gcaggcttcc   2040
gtcacttccg ttgatgtgga tgtgtttccg gatacgacgc agtcgagttt cacgtactac   2100
gatgatgatg gcgccagtta taactatgag agcggcactt atttttaagca aaatatgact   2160
gctcaggata tgggtcagg ctcgttaagt tttactttag gagcaaagag tggcagttac   2220
acgccggctc tccaatccta tatcgttaag ctgcacggtt ctgctggaac ttctgttacg   2280
aataacagcg cagctatgac atcttatgca agcttggaag cattaaaagc tgctgctggg   2340
gaaggctggg cgactgggaa ggacatttat ggggatgtca cctatgtgaa agtgacggca   2400
ggtacagctt cttctaaatc tattgctgtt acaggtgttg ctgccgtgag cgcaactact   2460
tcgcaatacg aagctgagga tgcatcgctt tctggcaatt cggttgctgc aaaggcgtcc   2520
```

| | |
|---|---|
| ataaacacga atcataccgg atatacggga actggatttg tagatggttt ggggaatgat | 2580 |
| ggcgctggtg tcaccttcta tccaaaggtg aaaactggcg gtgactacaa tgtctccttg | 2640 |
| cgttatgcga atgcttcagg cacggctaag tcagtcagta ttttttgttaa tggaaaaaga | 2700 |
| gtgaagtcca cctcgctcgc taatctcgca aattgggaca cttggtctac acaatctgag | 2760 |
| acactgccgt tgacggcagg tgtgaatgtt gtgacctata aatattactc cgatgcggga | 2820 |
| gatacaggca atgttaacat cgacaacatc acggtaccct ttgcgccaat tatccggtaag | 2880 |
| tatgaagcag agagtgctga gctttctggt ggcagctcat tgaacacgaa ccattggtac | 2940 |
| tacagtggta cggcttttgt agacggtttg agtgctgtag gcgcgcaggt gaaatacaac | 3000 |
| gtgaatgtcc ctagcgcagg aagttatcag gtagcgctgc gatatgcgaa tggcagtgca | 3060 |
| gcgacgaaaa cgttgagtac ttatatcaat ggagccaagc tggggcaaac cagttttacg | 3120 |
| agtcctggta cgaattggaa tgtttggcag gataatgtgc aaacggtgac gttaaatgca | 3180 |
| ggggcaaaca cgattgcgtt taaatacgac gccgctgaca cgggaacat caacgtagat | 3240 |
| cgtctgcttc tttcaacttc ggcagcggga acgccggttt ctgagcagaa cctgctagac | 3300 |
| aatcccggtt tcgagcgtga cacgagtcaa accaataact ggattgagtg gcatccaggc | 3360 |
| acgcaagctg ttgcttttgg cgttgatagc ggctcaacca ccaatccgcc ggaatccccg | 3420 |
| tggtcgggtg ataagcgtgc ctacttcttt gcagcaggtg cctatcaaca aagcatccat | 3480 |
| caaaccatta gtgttcctgt taataatgta aaatacaaat ttgaagcctg gtccgcatg | 3540 |
| aagaatacga cgccgacgac ggcaagagcc gaaattcaaa actatggcgg atcagccatt | 3600 |
| tatgcgaaca taagtaacag cggtgtttgg aaatatatca gcgtaagtga tattatggtg | 3660 |
| accaatggtc agatagatgt tggattttac gtggattcac ctggtggaac tacgcttcac | 3720 |
| attgatgatg tgcgcgtaac caaacaa | 3747 |

<210> SEQ ID NO 5
<211> LENGTH: 3753
<212> TYPE: DNA
<213> ORGANISM: Bacillus globisporus N75

<400> SEQUENCE: 5

| | |
|---|---|
| catgtgagcg cgctgggcaa cctgcttttcc tcggcggtga ccggggatac gctcacgctg | 60 |
| acgatcgata acggcgcgga accgaatgac gatattctag ttctgcaagc agtccagaac | 120 |
| ggtattctga aggtggacta ccggccgaac ggtgtagctc caagcgcgga tacgccgatg | 180 |
| ctggatccca ataaaacctg gccgtccata ggcgccgtta tcaatacagc ctctaatccg | 240 |
| atgacgatca caacgccggc gatgaagatt gagattgcca aaaatccggt gcgcctgacc | 300 |
| gtgaaaaaac cggacggcac cgctctgtta tgggaacccc cgaccggcgg cgtcttctcg | 360 |
| gacggcgtcc gtttcttgca cgggacgggc gacaatatgt acggcatccg cagcttcaat | 420 |
| gcttttgaca gcgcgcggga tctgctgcgc aacagctcca cccaagccgc ccgtgcaggc | 480 |
| gaccagggca actccggcgg cccgctgatc tggagcacag ccgggtacgg ggtgctcgtt | 540 |
| gacagcgacg gtgggtatcc gttcacggac gaggctaccg gcaagctgga gttctattac | 600 |
| ggcggcacgc ctccggaagg ccggcgctat acgaagcagg atgtggagta ctacatcatg | 660 |
| ctcggcacgc cgaaagagat catgtccggc gtcggggaaa ttacgggcaa accgccgatg | 720 |
| ctgcccaagt ggtccctggg ctttatgaac ttcgagtggg atctgaatga agctgagctc | 780 |
| aagaaccatg tggatacgta ccgggccaaa atattccga tcgacggcta tgcgatcgat | 840 |
| ttcgattgga gaagtacgg cgagaataat tacggcgaat tcgcttggaa tacggccaat | 900 |

```
ttcccttccg ccgccacgac ggcgctgaag tcgcagatgg acgccaaggg cattaaaatg    960
atcggcataa ccaagcctcg catcgcgacg aaggattttt cgaacaatcc taccgtgcag   1020
ggaacggacg cggcgagcgg cggttatttt tatccgggac atagcgaata caaggactac   1080
ttcatcccgg tctttgtgcg cagcatcgac ccttataacc ctgctgcacg ctcctggttc   1140
tggaaccact ccaaggatgc gttcgataaa ggcatcgtag gctggtggaa cgacgagacg   1200
gatgcggtat cgtcgggagg ggcctcctac tggttcggca atttttacga cggccatatg   1260
tcccaggcgc tttacgaggg acagcgggca tatacgtcga acgcccagcg cgtctggcag   1320
acagcgcgca cgttctatcc cggggcgcag cgttatgcga cgacgctctg gtcgggagac   1380
atcgggattc agtataccaa gggggaaaga atcaactggg ctgccggcat gcaggagcag   1440
cgggcggtga tgctttcttc gatcaacaac ggccaggtca atgggaat ggacacaggc    1500
ggcttcaacc agcaggacgg cacgacgaac aatccgaatc cggacctgta cgccagatgg   1560
atgcagttca gcgcgctgac tccggtgttc cgcgtgcatg caacaatca ccagcagcgc    1620
cagccttggt attatggctc gacagccgag gaggcatcca aggaagcgct ccagctccgt   1680
tactccctga ttccttatat gtatgcttac gaaagaagcg cctacgagaa cggtaacgga   1740
cttgtccggc cgctgatgca ggaataccct gccgatgcca acgccaaaaa ctatctcgat   1800
gcctggatgt tcggcgattg gctgctggcg gcgcctgtgg tcgagaagca gcagacctcc   1860
aaggaaatct atctccctgc aggcacttgg attgactaca accggggcac ggtgctcacc   1920
ggcggccaga agatcagcta cgccgtcaat cccgacacgc tgacggatat tccgctcttc   1980
attaagaagg gcgcgattat cccttcgcag aaggtgcagg actacgtggg ccaggctccc   2040
gtccaaacgt ggatgtgga tgtattcccg aatacgcac aatcgagctt tacctattat     2100
gacgatgacg gcagcagcta caattatgaa agcggagctt acttcaagca attgatgacg   2160
gctcaggaca acgatccgg tgcgctgagc tttacgctgg cgccaaaac cggcacgtac     2220
agccccgcac tgcaatccta tatcgtcaag cttcacgggg ccgcaggcgc gtcggtgaca   2280
agcaatgggg cggcgctggc ctcctatgcc agcctgcaag cgctgaaagc ctcagccagt   2340
gaaggctggg ccaagggcaa ggacatctac ggcgatgtca cgtatgtcaa gctatccgcg   2400
ggggcagcgg cggccaaggc gattgccgtc accggcaaca gcccggtcag cgtggcggat   2460
gtgcagtacg aagccgaaga agcttcgctg tccggcaata cgacagcaac caaggcgacc   2520
gtgaatacga accacgcagg ctacacgggc agcggcttcg tggatggact gagtaatccg   2580
ggagcggcgg ttacgttcta tccgaaggtg aaaacgggcg gagactacaa tgtctcgctg   2640
cgctacgcta attcgacggg agcggcaaag agcgtcagca tcttcgttaa cggcaagcgc   2700
gtcaaatcca cgtcgctggc gaacctgccg aactgggata cgtggggac gcaggctgag   2760
acactgccgc tgacgcggg gacgaacgtt gtcacctaca agttctactc ggatgccgga   2820
gatacgggct cggttaacct ggacaacatc acggtgccct tcgctccggc catcggcaaa   2880
tacgaggcgg agagcgccga gctgagcggc ggcagcacgg tcaaccagaa tcattggttc   2940
tacagcggca cggcatttgt agatggctta accgcaccgg gcgcccaagt caaatatacc   3000
gtgaacgccc cggccgcagg cagctaccag atcgcgcttc gctatgcgaa cggcacgggt   3060
gctgcgaaga cgctcagcac gtatgtgaac gggacgaagc tggggcaaac ggccttcgcc   3120
agccctggcg gcaactggaa cgtgtggcag acagcgtgc agaccgtcgc gctcgccgcc    3180
ggtacgaaca cgatcgcgtt caagtacgat gccggcgaca gcggcagcgg cagcgtcaat   3240
```

```
ctggaccgtc tgttgctctc tgccgcagcg ccaggcgtgc ccgtgtccga gcagaacctg    3300
ctcgataacg ggggctttga acgcgatccg tcgcagagca gcaactggac cgagtggcat    3360
ccggcttcgc aggcgattgc ttacggcatc gacagcggct ccgggatgaa tccgcctgaa    3420
tcgccatggg caggcgataa gcgcgcctat ttctatgcgg caggcccgta tcagcaaagc    3480
atccatcaaa cagtcagcgt gcctgtcaat aatgccaagt acaagttcga agcctgggta    3540
ttgctgaaga atacaacacc gacaacggcc cgggtggaga ttcaaaatta cggcggttcg    3600
ccgatcttca cgaacatcag taaagacggc gtctggaaat acatcagcgt cagcgatatt    3660
caggtcacga acgccaaat cgatattggc ttctatgtgg attcgcccgg aggcaccacg    3720
ctccacatcg acgatgtgcg ggtcaccaag caa                                 3753

<210> SEQ ID NO 6
<211> LENGTH: 2787
<212> TYPE: DNA
<213> ORGANISM: Arthrobacter globiformis A19

<400> SEQUENCE: 6
gctcccctgg gcgtgcaacg cgcgcagttc cagtcggggt cgagctacct cgtcgtcgag     60
gtgctcgatg acgacctcgt ccacttcgag ctggccgggg gcggcaccgc ccccggcacg    120
ggctccccgc tgttcacgac gcctcaggtc gcgaagcacg actacgcggg acccgacgtg    180
ttcacccaga ccgggtctgt tctgcagacc gcggcgatgc gcatcgaggt cgatcccgcg    240
gatctgtgcg tgacgccac cgacataccc cgcaccccga accttgtact gcacgaggcg    300
tgtcccgccg acctcggcca ggcgtggaag gggctgaaca tcacgaggtc ggcgatggag    360
aacgcctacg gtctcgggca gcagttcttc acgggcggca gcgcggacgg cgactgggtg    420
ggccgcaccc gcaccccggg tggcacctac ggcaacgcga tggtgttcga ccccgagaac    480
gggccggtcg gcaacacgca gatcccggtg ctcttcgcgg tcggcgatga caacgcgaac    540
tacgggctgt tcgtcgatca gctgtacaag caggaatgga acctcaccgg cgacccgtgg    600
acggtgcgca tgtggggcga ccaggtcgcg tggtacctca tgagcggcga cgacctgccc    660
gaccttcgcc acgactacat ggagctgacg ggcacccgc ccgtgccgcc gaagaaggcg    720
ttcgggctct gggtgtcgga gttcggctac gacaactgga gcgaggtcga caatacgatc    780
gcgggcctgc gctcggccga cttccggtc gatggcgcga tgctcgacgt acagtggttc    840
gggggcgtca ccgccgactc ggacgacacc cgcatgggca ccctcgattg ggacacgtcg    900
aggtttcccg accctgcggg aaagatcgcc gacctcgccg aggacggcgt cggcatcatc    960
ccgatcgagg agtcgtacgt cggtcgcaac ctgccggagc acgcccggat ggcggcggac   1020
ggttacctcg tgcgctccgg ctgcgctacg tgcccgccgg tgtacctgac ggggaaccc   1080 tggtgggggca agggcgggat gatcgactgg acgcagccgg aagccggcgc cgtctggcac   1140
gacgagcagc gccagcatct cgtcgacgag ggcgtactgg ccactggct cgatctcggc   1200 gaaccggaga tgtacgaccc gaacgactgg accgccggcg tcatccccgg caagcacgcg   1260
cacgccgact atcacaacgc gtacaacctg ctgtgggcgc agagcatcgc cgacgggtac   1320
gccgacaacg cgtgcagaa gcgtcccttc atgctgacgc gcgccgcggc cgccggcatc   1380
cagcgtcatg gcgcgggcat gtggtcagcc gacatcggt cgaccatgaa ggcgctcggg   1440
agccagcaga acgcgcagat gcacatgtcg atgtcgggga tcgactatta cggctccgac   1500
atcggcgggt tccggcggga gatggccgac ggcgacgtga acgagctcta cacccagtgg   1560
ttcgccgaca gcgcgtggtt cgacactccg ctccggccgc acaccgacaa tctctgcaac   1620
```

```
tgcctcgaga cgagccccga ctcgatcggc gacgtcgcga gcaaccgcga gaacctggtg   1680
cgccgctacg agctggctcc gtactactac tcgctcgcgc accgcgctca ccagttcggc   1740
gagccgctcg ctcccccgct cgtgtactac taccagaacg acgaccacgt tcgcgagatg   1800
gggcatcaga agatgctcgg cgcgacctg ctgatcgcga tcgtcgccgg agagggcgag   1860
cgggaacgcg acgtgtacct tccggcgggc gagtggatcg acatccacac gaacgagcgc   1920
atccagagca cgggtcagtg gatcgacaac gtgccgctgt ggcgtgacgg cgtcttcacc   1980
ctgccggcgt acgcccgggc gggggcgatc atcccgaagg ccttcgtcga cgcctccacg   2040
aaggacatca ccggcaagcg cgaggatgcc gcggtgcgca acgagctgat cgcaaccgtt   2100
tacgccgacg acgtcgcgag cgacttcacc ctgtacgagg atgacggcgc gacgaccgca   2160
tacgccgacg gggctgtcag gaccacgcag atcagccaat cgctcacgaa cggcgtggcc   2220
acggtgacgg tgggagcggc atctggaacc tactccggtg cgccctccac ccgtcccacg   2280
gtcgtcgagc ttgtcactga cggcacgcag gcctcgaccg tctccctcgg cagcgttccg   2340 ctgacgagc acgcgaacaa ggcggcgttc gacgcggcga gcagcggctg gtacaacgcc   2400 ggcgggggc tcgttgtggc caaggcggcg agcagttcgg tgaacaccgc caagaccttc   2460
tcgttcacgc tcggtgagga gtcggtctgg gcgacgttct cctgcgagaa cgccacgacg   2520
accttcggtc agtcagtgta cgtcgtcgga aatgttccgc agctcggcaa ctggtcgccg   2580
gcggatgccg tgaagctcga gccgagcgcc tacccacct ggaccggggt ggtgcggaac   2640
ctgccgccgt cgagcacggt cgaatggaag tgcatcaaac gtcaggaggc cggcctgccg   2700
aacacggcgg atgcgtggga gcccggcggg aacaacatcc tctcgacgcc accttccggc   2760
tcggcgggga taaccaccgg cgccttc                                        2787
```

<210> SEQ ID NO 7
<211> LENGTH: 9
<212> TYPE: PRT
<213> ORGANISM: Bacillus globisporus C11

<400> SEQUENCE: 7

Tyr Val Ser Ser Leu Gly Asn Leu Ile
1               5

<210> SEQ ID NO 8
<211> LENGTH: 10
<212> TYPE: PRT
<213> ORGANISM: Bacillus globisporus C11

<400> SEQUENCE: 8

Asp Ile Tyr Gly Asp Val Thr Tyr Val Lys
1               5                   10

<210> SEQ ID NO 9
<211> LENGTH: 14
<212> TYPE: PRT
<213> ORGANISM: Bacillus globisporus C11

<400> SEQUENCE: 9

Gln Pro Trp Tyr Phe Gly Ser Thr Ala Glu Glu Ala Ser Lys
1               5                   10

<210> SEQ ID NO 10
<211> LENGTH: 31
<212> TYPE: PRT
<213> ORGANISM: Bacillus globisporus C11

```
<400> SEQUENCE: 10

Ala Ser Ile Asn Thr Asn His Thr Gly Tyr Thr Gly Thr Gly Phe Val
1               5                   10                  15

Asp Gly Leu Gly Asn Asp Gly Ala Gly Val Thr Phe Tyr Pro Lys
            20                  25                  30

<210> SEQ ID NO 11
<211> LENGTH: 25
<212> TYPE: PRT
<213> ORGANISM: Bacillus globisporus C11

<400> SEQUENCE: 11

Leu Leu Leu Ser Thr Ser Ala Ala Gly Thr Pro Val Ser Glu Gln Asn
1               5                   10                  15

Leu Leu Asp Asn Pro Gly Phe Glu Arg
            20                  25

<210> SEQ ID NO 12
<211> LENGTH: 14
<212> TYPE: PRT
<213> ORGANISM: Bacillus globisporus C11

<400> SEQUENCE: 12

Asp Ile Tyr Leu Pro Ser Gly Ser Trp Ile Asp Tyr Ala Arg
1               5                   10

<210> SEQ ID NO 13
<211> LENGTH: 33
<212> TYPE: PRT
<213> ORGANISM: Bacillus globisporus C11

<400> SEQUENCE: 13

Asp Ala Ser Ala Asn Val Thr Thr Gln Gly Thr Asp Ala Thr Asn Gly
1               5                   10                  15

Gly Tyr Phe Tyr Pro Gly His Asn Glu Tyr Gln Asp Tyr Phe Ile Pro
            20                  25                  30

Val

<210> SEQ ID NO 14
<211> LENGTH: 24
<212> TYPE: PRT
<213> ORGANISM: Bacillus globisporus C11

<400> SEQUENCE: 14

Tyr Tyr Ser Asp Ala Gly Asp Thr Gly Asn Val Asn Ile Asp Asn Ile
1               5                   10                  15

Thr Val Pro Phe Ala Pro Ile Ile
            20

<210> SEQ ID NO 15
<211> LENGTH: 16
<212> TYPE: PRT
<213> ORGANISM: Bacillus globisporus C11

<400> SEQUENCE: 15

Ser Thr Ser Leu Ala Asn Leu Ala Asn Trp Asp Thr Trp Ser Thr Gln
1               5                   10                  15

<210> SEQ ID NO 16
<211> LENGTH: 17
<212> TYPE: PRT
```

-continued

<213> ORGANISM: Bacillus globisporus C11

<400> SEQUENCE: 16

Trp Ser Leu Gly Phe Met Asn Phe Glu Trp Asp Thr Asn Gln Thr Glu
1               5                   10                  15

Phe

<210> SEQ ID NO 17
<211> LENGTH: 20
<212> TYPE: PRT
<213> ORGANISM: Bacillus globisporus C11

<400> SEQUENCE: 17

Asn Tyr Thr Asp Ala Trp Met Phe Gly Asp Trp Leu Leu Ala Ala Pro
1               5                   10                  15

Val Val Asp Lys
            20

<210> SEQ ID NO 18
<211> LENGTH: 5180
<212> TYPE: DNA
<213> ORGANISM: Bacillus globisporus C11
<220> FEATURE:
<221> NAME/KEY: CDS
<222> LOCATION: (877)..(4728)

<400> SEQUENCE: 18

```
atctaccggt ttttgtgaag tttggcagta ttcttccgat gaatttgaac gcgcaatatc      60
aagtgggcgg gaccattggc aacagcttga cgagctacac gaatctcgcg ttccgcattt     120
atccgcttgg gacaacaacg tacgactgga atgatgatat tggcggttcg gtgaaaacca     180
taacttctac agagcaatat ggcttgaata agaaaccgt gactgttcca gcgattaatt      240
ctaccaagac attgcaagtg tttacgacta agccttcctc tgtaacggtg ggtggttctg     300
tgatgacaga gtacagtact ttaactgccc taacgggagc gtcgacaggc tggtactatg     360
atactgtaca gaaattcact tacgtcaagc ttggttcaag tgcatctgct caatccgttg     420
tgctaaatgg cgttaataag gtggaatatg aagcagaatt cggcgtgcaa agcggcgttt     480
caacgaacac gaaccatgca ggttatactg gtacaggatt tgtggacggc tttgagactc     540
ttggagacaa tgttgctttt gatgtttccg tcaaagccgc aggtacttat acgatgaagg     600
ttcggtattc atccggtgca ggcaatggct caagagccat ctatgtgaat aacaccaaag     660
tgacggacct tgccttgccg caaacaacaa gctgggatac atgggggact gctacgttta     720
gcgtctcgct gagtacaggt ctcaacacgt tgaaagtcag ctatgatggt accagttcac     780
ttggcattaa tttcgataac atcgcgattg tagagcaata aaaggtcggg agggcaagtc     840
cctcccttaa tttctaatcg aaagggagta tccttg atg cgt cca cca aac aaa     894
                                           Met Arg Pro Pro Asn Lys
                                             1                 5
gaa att cca cgt att ctt gct ttt ttt aca gcg ttt acg ttg ttt ggt       942
Glu Ile Pro Arg Ile Leu Ala Phe Phe Thr Ala Phe Thr Leu Phe Gly
           10                  15                  20
tca acc ctt gcc ttg ctt cct gct ccg cct gcg cat gcc tat gtc agc       990
Ser Thr Leu Ala Leu Leu Pro Ala Pro Pro Ala His Ala Tyr Val Ser
       25                  30                  35
agc cta gga aat ctc att tct tcg agt gtc acc gga gat acc ttg acg      1038
Ser Leu Gly Asn Leu Ile Ser Ser Ser Val Thr Gly Asp Thr Leu Thr
   40                  45                  50
cta act gtt gat aac ggt gcg gag ccg agt gat gac ctc ttg att gtt      1086
```

```
Leu Thr Val Asp Asn Gly Ala Glu Pro Ser Asp Asp Leu Leu Ile Val
 55                  60                  65                  70 caa gcg gtg caa aac ggt att ttg aag gtg gat tat cgt cca aat agc    1134
Gln Ala Val Gln Asn Gly Ile Leu Lys Val Asp Tyr Arg Pro Asn Ser
                 75                  80                  85 ata acg ccg agc gcg aag acg ccg atg ctg gat ccg aac aaa act tgg    1182
Ile Thr Pro Ser Ala Lys Thr Pro Met Leu Asp Pro Asn Lys Thr Trp
             90                  95                 100 tca gct gta gga gct acg att aat acg aca gcc aat cca atg acc atc    1230
Ser Ala Val Gly Ala Thr Ile Asn Thr Thr Ala Asn Pro Met Thr Ile
            105                 110                 115 acg act tcc aat atg aag att gag att acc aag aat cca gta cga atg    1278
Thr Thr Ser Asn Met Lys Ile Glu Ile Thr Lys Asn Pro Val Arg Met
        120                 125                 130 acg gtc aag aag gcg gac ggc act acg cta ttc tgg gaa cca tca ggc    1326
Thr Val Lys Lys Ala Asp Gly Thr Thr Leu Phe Trp Glu Pro Ser Gly
135                 140                 145                 150 gga ggg gta ttc tca gac ggt gtg cgc ttc ctt cat gcc aca ggg gat    1374
Gly Gly Val Phe Ser Asp Gly Val Arg Phe Leu His Ala Thr Gly Asp
                155                 160                 165 aat atg tat ggc atc cgg agc ttc aat gct ttt gat agc ggg ggt gac    1422
Asn Met Tyr Gly Ile Arg Ser Phe Asn Ala Phe Asp Ser Gly Gly Asp
            170                 175                 180 ctg ctg cgg aat tcg tcc aat cat gcc gcc cat gcg ggt gaa cag gga    1470
Leu Leu Arg Asn Ser Ser Asn His Ala Ala His Ala Gly Glu Gln Gly
        185                 190                 195 gat tcc ggt ggt ccg ctt att tgg agt acg gca gga tat gga cta tta    1518
Asp Ser Gly Gly Pro Leu Ile Trp Ser Thr Ala Gly Tyr Gly Leu Leu
200                 205                 210 gtc gat agc gat ggc ggc tac ccc tat aca gat agc aca acc ggt caa    1566
Val Asp Ser Asp Gly Gly Tyr Pro Tyr Thr Asp Ser Thr Thr Gly Gln
215                 220                 225                 230 atg gag ttt tat tat ggt ggg acc cct cct gag gga cgt cgt tat gcg    1614
Met Glu Phe Tyr Tyr Gly Gly Thr Pro Pro Glu Gly Arg Arg Tyr Ala
                235                 240                 245 aaa caa aac gtg gaa tat tat att atg ctc gga acc ccc aag gaa att    1662
Lys Gln Asn Val Glu Tyr Tyr Ile Met Leu Gly Thr Pro Lys Glu Ile
            250                 255                 260 atg acc gac gta ggg gaa atc aca ggg aaa ccg cct atg ctg cct aag    1710
Met Thr Asp Val Gly Glu Ile Thr Gly Lys Pro Pro Met Leu Pro Lys
        265                 270                 275 tgg tcg ctt gga ttc atg aac ttt gag tgg gat acg aat caa acg gag    1758
Trp Ser Leu Gly Phe Met Asn Phe Glu Trp Asp Thr Asn Gln Thr Glu
280                 285                 290 ttt acg aat aat gtg gat acg tat cgt gcc aaa aat atc ccc ata gat    1806
Phe Thr Asn Asn Val Asp Thr Tyr Arg Ala Lys Asn Ile Pro Ile Asp
295                 300                 305                 310 gct tac gcc ttc gac tat gac tgg aaa aag tac ggg gaa acc aac tat    1854
Ala Tyr Ala Phe Asp Tyr Asp Trp Lys Lys Tyr Gly Glu Thr Asn Tyr
                315                 320                 325 ggt gaa ttc gcg tgg aat acg act aat ttc cct tct gcg tca acg act    1902
Gly Glu Phe Ala Trp Asn Thr Thr Asn Phe Pro Ser Ala Ser Thr Thr
            330                 335                 340 tct tta aag tca aca atg gat gct aaa ggc atc aaa atg atc gga att    1950
Ser Leu Lys Ser Thr Met Asp Ala Lys Gly Ile Lys Met Ile Gly Ile
        345                 350                 355 aca aaa ccc cgc atc gtt acg aag gat gct tca gcg aat gtg acg acc    1998
Thr Lys Pro Arg Ile Val Thr Lys Asp Ala Ser Ala Asn Val Thr Thr
360                 365                 370
```

-continued

| | | |
|---|---|---|
| caa ggg acg gac gcg aca aat ggc ggt tat ttt tat cca ggc cat aac<br>Gln Gly Thr Asp Ala Thr Asn Gly Gly Tyr Phe Tyr Pro Gly His Asn<br>375                  380                  385                  390 | 2046 |
| gag tat cag gat tat ttc att ccc gta act gtg cgt agt atc gat cct<br>Glu Tyr Gln Asp Tyr Phe Ile Pro Val Thr Val Arg Ser Ile Asp Pro<br>               395                 400                  405 | 2094 |
| tac aat gct aac gaa cgt gct tgg ttc tgg aat cat tcc aca gat gcg<br>Tyr Asn Ala Asn Glu Arg Ala Trp Phe Trp Asn His Ser Thr Asp Ala<br>          410                       415                 420 | 2142 |
| ctt aat aaa ggg atc gta ggt tgg aat gac gag acg gat aaa gta<br>Leu Asn Lys Gly Ile Val Gly Trp Trp Asn Asp Glu Thr Asp Lys Val<br>               425                   430                 435 | 2190 |
| tct tcg ggt gga gcg tta tat tgg ttt ggc aat ttc aca aca ggc cac<br>Ser Ser Gly Gly Ala Leu Tyr Trp Phe Gly Asn Phe Thr Thr Gly His<br>440                  445                  450 | 2238 |
| atg tct cag acg atg tac gaa ggg ggg cgg gct tac acg agt gga gcg<br>Met Ser Gln Thr Met Tyr Glu Gly Gly Arg Ala Tyr Thr Ser Gly Ala<br>455                  460                  465                  470 | 2286 |
| cag cgt gtt tgg caa acg gct aga acc ttc tac cca ggt gcc cag cgg<br>Gln Arg Val Trp Gln Thr Ala Arg Thr Phe Tyr Pro Gly Ala Gln Arg<br>                     475                 480                 485 | 2334 |
| tat gcg act acg ctt tgg tct ggc gat att ggc att caa tac aat aaa<br>Tyr Ala Thr Thr Leu Trp Ser Gly Asp Ile Gly Ile Gln Tyr Asn Lys<br>          490                       495                 500 | 2382 |
| ggc gaa cgg atc aat tgg gct gcc ggg atg cag gag caa agg gca gtt<br>Gly Glu Arg Ile Asn Trp Ala Ala Gly Met Gln Glu Gln Arg Ala Val<br>               505                   510                 515 | 2430 |
| atg cta tcc tcc gtg aac aat ggc cag gtg aaa tgg ggc atg gat acc<br>Met Leu Ser Ser Val Asn Asn Gly Gln Val Lys Trp Gly Met Asp Thr<br>520                  525                  530 | 2478 |
| ggc gga ttc aat cag cag gat ggc acg acg aac aat ccg aat ccc gat<br>Gly Gly Phe Asn Gln Gln Asp Gly Thr Thr Asn Asn Pro Asn Pro Asp<br>535                  540                  545                  550 | 2526 |
| tta tac gct cgg tgg atg cag ttc agt gcc cta acg cct gtt ttc cga<br>Leu Tyr Ala Arg Trp Met Gln Phe Ser Ala Leu Thr Pro Val Phe Arg<br>               555                   560                 565 | 2574 |
| gtg cat ggg aac aac cat cag cag cgc cag cca tgg tac ttc gga tcg<br>Val His Gly Asn Asn His Gln Gln Arg Gln Pro Trp Tyr Phe Gly Ser<br>          570                       575                 580 | 2622 |
| act gcg gag gag gcc tcc aaa gag gca att cag ctg cgg tac tcc ctg<br>Thr Ala Glu Glu Ala Ser Lys Glu Ala Ile Gln Leu Arg Tyr Ser Leu<br>585                  590                  595 | 2670 |
| atc cct tat atg tat gcc tat gag aga agt gct tac gag aat ggg aat<br>Ile Pro Tyr Met Tyr Ala Tyr Glu Arg Ser Ala Tyr Glu Asn Gly Asn<br>600                  605                  610 | 2718 |
| ggg ctc gtt cgg cca ttg atg caa gcc tat cca aca gat gcg gcc gtc<br>Gly Leu Val Arg Pro Leu Met Gln Ala Tyr Pro Thr Asp Ala Ala Val<br>615                  620                  625                  630 | 2766 |
| aaa aat tac acg gat gct tgg atg ttt ggt gac tgg ctg ctg gct gca<br>Lys Asn Tyr Thr Asp Ala Trp Met Phe Gly Asp Trp Leu Leu Ala Ala<br>               635                   640                 645 | 2814 |
| cct gtg gta gat aaa cag cag acg agt aag gat atc tat tta ccg tct<br>Pro Val Val Asp Lys Gln Gln Thr Ser Lys Asp Ile Tyr Leu Pro Ser<br>          650                       655                 660 | 2862 |
| ggg tca tgg att gac tat gcg cga ggc aat gca ata act ggc ggt caa<br>Gly Ser Trp Ile Asp Tyr Ala Arg Gly Asn Ala Ile Thr Gly Gly Gln<br>               665                   670                 675 | 2910 |
| acc atc cga tat tcg gtt aat ccg gac acg ttg aca gac atg cct ctc<br>Thr Ile Arg Tyr Ser Val Asn Pro Asp Thr Leu Thr Asp Met Pro Leu<br>680                  685                  690 | 2958 |

-continued

| | |
|---|---|
| ttt att aaa aaa ggt gcc att att cca aca cag aaa gtg cag gat tac<br>Phe Ile Lys Lys Gly Ala Ile Ile Pro Thr Gln Lys Val Gln Asp Tyr<br>695                700                705              710 | 3006 |
| gta ggg cag gct tcc gtc act tcc gtt gat gtg gat gtg ttt ccg gat<br>Val Gly Gln Ala Ser Val Thr Ser Val Asp Val Asp Val Phe Pro Asp<br>               715                720                725 | 3054 |
| acg acg cag tcg agt ttc acg tac tac gat gat gat ggc gcc agt tat<br>Thr Thr Gln Ser Ser Phe Thr Tyr Tyr Asp Asp Asp Gly Ala Ser Tyr<br>730                735                740 | 3102 |
| aac tat gag agc ggc act tat ttt aag caa aat atg act gct cag gat<br>Asn Tyr Glu Ser Gly Thr Tyr Phe Lys Gln Asn Met Thr Ala Gln Asp<br>     745               750                755 | 3150 |
| aat ggg tca ggc tcg tta agt ttt act tta gga gca aag agt ggc agt<br>Asn Gly Ser Gly Ser Leu Ser Phe Thr Leu Gly Ala Lys Ser Gly Ser<br>760                765                770 | 3198 |
| tac acg ccg gct ctc caa tcc tat atc gtt aag ctg cac ggt tct gct<br>Tyr Thr Pro Ala Leu Gln Ser Tyr Ile Val Lys Leu His Gly Ser Ala<br>775                780                785              790 | 3246 |
| gga act tct gtt acg aat aac agc gca gct atg aca tct tat gca agc<br>Gly Thr Ser Val Thr Asn Asn Ser Ala Ala Met Thr Ser Tyr Ala Ser<br>               795                800              805 | 3294 |
| ttg gaa gca tta aaa gct gct gct ggg gaa ggc tgg gcg act ggg aag<br>Leu Glu Ala Leu Lys Ala Ala Ala Gly Glu Gly Trp Ala Thr Gly Lys<br>          810                815                820 | 3342 |
| gac att tat ggg gat gtc acc tat gtg aaa gtg acg gca ggt aca gct<br>Asp Ile Tyr Gly Asp Val Thr Tyr Val Lys Val Thr Ala Gly Thr Ala<br>825                830                835 | 3390 |
| tct tct aaa tct att gct gtt aca ggt gtt gct gcc gtg agc gca act<br>Ser Ser Lys Ser Ile Ala Val Thr Gly Val Ala Ala Val Ser Ala Thr<br>840                845                850 | 3438 |
| act tcg caa tac gaa gct gag gat gca tcg ctt tct ggc aat tcg gtt<br>Thr Ser Gln Tyr Glu Ala Glu Asp Ala Ser Leu Ser Gly Asn Ser Val<br>855                860                865              870 | 3486 |
| gct gca aag gcg tcc ata aac acg aat cat acc gga tat acg gga act<br>Ala Ala Lys Ala Ser Ile Asn Thr Asn His Thr Gly Tyr Thr Gly Thr<br>               875                880              885 | 3534 |
| gga ttt gta gat ggt ttg ggg aat gat ggc gct ggt gtc acc ttc tat<br>Gly Phe Val Asp Gly Leu Gly Asn Asp Gly Ala Gly Val Thr Phe Tyr<br>          890                895                900 | 3582 |
| cca aag gtg aaa act ggc ggt gac tac aat gtc tcc ttg cgt tat gcg<br>Pro Lys Val Lys Thr Gly Gly Asp Tyr Asn Val Ser Leu Arg Tyr Ala<br>905                910                915 | 3630 |
| aat gct tca ggc acg gct aag tca gtc agt att ttt gtt aat gga aaa<br>Asn Ala Ser Gly Thr Ala Lys Ser Val Ser Ile Phe Val Asn Gly Lys<br>920                925                930 | 3678 |
| aga gtg aag tcc acc tcg ctc gct aat ctc gca aat tgg gac act tgg<br>Arg Val Lys Ser Thr Ser Leu Ala Asn Leu Ala Asn Trp Asp Thr Trp<br>935                940                945              950 | 3726 |
| tct aca caa tct gag aca ctg ccg ttg acg gca ggt gtg aat gtt gtg<br>Ser Thr Gln Ser Glu Thr Leu Pro Leu Thr Ala Gly Val Asn Val Val<br>               955                960              965 | 3774 |
| acc tat aaa tat tac tcc gat gcg gga gat aca ggc aat gtt aac atc<br>Thr Tyr Lys Tyr Tyr Ser Asp Ala Gly Asp Thr Gly Asn Val Asn Ile<br>970                975                980 | 3822 |
| gac aac atc acg gta cct ttt gcg cca att atc ggt aag tat gaa gca<br>Asp Asn Ile Thr Val Pro Phe Ala Pro Ile Ile Gly Lys Tyr Glu Ala<br>985                990                995 | 3870 |
| gag agt  gct gag ctt tct ggt  ggc agc tca ttg aac  acg aac cat<br>Glu Ser  Ala Glu Leu Ser Gly  Gly Ser Ser Leu Asn  Thr Asn His | 3915 |

```
              1000                1005                1010
tgg tac tac agt ggt acg gct ttt gta gac ggt ttg agt gct gta            3960
Trp Tyr Tyr Ser Gly Thr Ala Phe Val Asp Gly Leu Ser Ala Val
    1015                1020                1025 ggc gcg cag gtg aaa tac aac gtg aat gtc cct agc gca gga agt            4005
Gly Ala Gln Val Lys Tyr Asn Val Asn Val Pro Ser Ala Gly Ser
    1030                1035                1040 tat cag gta gcg ctg cga tat gcg aat ggc agt gca gcg acg aaa            4050
Tyr Gln Val Ala Leu Arg Tyr Ala Asn Gly Ser Ala Ala Thr Lys
    1045                1050                1055 acg ttg agt act tat atc aat gga gcc aag ctg ggg caa acc agt            4095
Thr Leu Ser Thr Tyr Ile Asn Gly Ala Lys Leu Gly Gln Thr Ser
    1060                1065                1070 ttt acg agt cct ggt acg aat tgg aat gtt tgg cag gat aat gtg            4140
Phe Thr Ser Pro Gly Thr Asn Trp Asn Val Trp Gln Asp Asn Val
    1075                1080                1085 caa acg gtg acg tta aat gca ggg gca aac acg att gcg ttt aaa            4185
Gln Thr Val Thr Leu Asn Ala Gly Ala Asn Thr Ile Ala Phe Lys
    1090                1095                1100 tac gac gcc gct gac agc ggg aac atc aac gta gat cgt ctg ctt            4230
Tyr Asp Ala Ala Asp Ser Gly Asn Ile Asn Val Asp Arg Leu Leu
    1105                1110                1115 ctt tca act tcg gca gcg gga acg ccg gtt tct gag cag aac ctg            4275
Leu Ser Thr Ser Ala Ala Gly Thr Pro Val Ser Glu Gln Asn Leu
    1120                1125                1130 cta gac aat ccc ggt ttc gag cgt gac acg agt caa acc aat aac            4320
Leu Asp Asn Pro Gly Phe Glu Arg Asp Thr Ser Gln Thr Asn Asn
    1135                1140                1145 tgg att gag tgg cat cca ggc acg caa gct gtt gct ttt ggc gtt            4365
Trp Ile Glu Trp His Pro Gly Thr Gln Ala Val Ala Phe Gly Val
    1150                1155                1160 gat agc ggc tca acc acc aat ccg ccg gaa tcc ccg tgg tcg ggt            4410
Asp Ser Gly Ser Thr Thr Asn Pro Pro Glu Ser Pro Trp Ser Gly
    1165                1170                1175 gat aag cgt gcc tac ttc ttt gca gca ggt gcc tat caa caa agc            4455
Asp Lys Arg Ala Tyr Phe Phe Ala Ala Gly Ala Tyr Gln Gln Ser
    1180                1185                1190 atc cat caa acc att agt gtt cct gtt aat aat gta aaa tac aaa            4500
Ile His Gln Thr Ile Ser Val Pro Val Asn Asn Val Lys Tyr Lys
    1195                1200                1205 ttt gaa gcc tgg gtc cgc atg aag aat acg acg ccg acg acg gca            4545
Phe Glu Ala Trp Val Arg Met Lys Asn Thr Thr Pro Thr Thr Ala
    1210                1215                1220 aga gcc gaa att caa aac tat ggc gga tca gcc att tat gcg aac            4590
Arg Ala Glu Ile Gln Asn Tyr Gly Gly Ser Ala Ile Tyr Ala Asn
    1225                1230                1235 ata agt aac agc ggt gtt tgg aaa tat atc agc gta agt gat att            4635
Ile Ser Asn Ser Gly Val Trp Lys Tyr Ile Ser Val Ser Asp Ile
    1240                1245                1250 atg gtg acc aat ggt cag ata gat gtt gga ttt tac gtg gat tca            4680
Met Val Thr Asn Gly Gln Ile Asp Val Gly Phe Tyr Val Asp Ser
    1255                1260                1265 cct ggt gga act acg ctt cac att gat gat gtg cgc gta acc aaa            4725
Pro Gly Gly Thr Thr Leu His Ile Asp Asp Val Arg Val Thr Lys
    1270                1275                1280 caa taaacaaaca accagctctc ccgttaatgg gagggctggt tgtttgttat             4778
Gln gataatccat ctatttagag tggattaaac gttttgaagt gcttgctgaa cttcttgcac     4838
```

-continued

```
aatggataac gccgcggtgc gggcacttga gaaagcacgt tctgcaagct ctcccttacc    4898
tgtacagccg tctccgcaga agtagaaagg aacgttttcc acgcgtatcg gcagcagatt    4958
attggaagca atgttttcca cgctggaaac catcgctttc ttggaaaccc gtttcacggc    5018
tgtgacatcg cgccagcctg ataatgttt atcaaataag gcttccattt ggaggttctt    5078
ctcttccagg tacgctttgc gctgctcctc gttatcaaag cggtcgctta agtatgcgat    5138
accttgcagc agctgcccgc cttctggtac tagtgtgtga tc                       5180
```

<210> SEQ ID NO 19
<211> LENGTH: 8
<212> TYPE: PRT
<213> ORGANISM: Bacillus globisporus N75

<400> SEQUENCE: 19

```
His Val Ser Ala Leu Gly Asn Leu
1               5
```

<210> SEQ ID NO 20
<211> LENGTH: 19
<212> TYPE: PRT
<213> ORGANISM: Bacillus globisporus N75

<400> SEQUENCE: 20

```
Thr Gly Gly Asp Tyr Asn Val Ser Leu Arg Tyr Ala Asn Ser Thr Gly
1               5                   10                  15

Ala Ala Lys
```

<210> SEQ ID NO 21
<211> LENGTH: 20
<212> TYPE: PRT
<213> ORGANISM: Bacillus globisporus N75

<400> SEQUENCE: 21

```
Asp Phe Ser Asn Asn Pro Thr Val Gln Gly Thr Asp Ala Ala Ser Gly
1               5                   10                  15

Gly Tyr Phe Tyr
            20
```

<210> SEQ ID NO 22
<211> LENGTH: 25
<212> TYPE: PRT
<213> ORGANISM: Bacillus globisporus N75

<400> SEQUENCE: 22

```
Tyr Thr Val Asn Ala Pro Ala Ala Gly Ser Tyr Gln Ile Ala Leu Arg
1               5                   10                  15

Trp Ala Asn Gly Thr Gly Ala Ala Lys
            20                  25
```

<210> SEQ ID NO 23
<211> LENGTH: 25
<212> TYPE: PRT
<213> ORGANISM: Bacillus globisporus N75

<400> SEQUENCE: 23

```
Tyr Glu Ala Glu Ser Ala Glu Leu Ser Gly Gly Ser Thr Val Asn Gln
1               5                   10                  15

Asn His Trp Phe Tyr Ser

```
<210> SEQ ID NO 24
<211> LENGTH: 11
<212> TYPE: PRT
<213> ORGANISM: Bacillus globisporus N75

<400> SEQUENCE: 24

Asn Tyr Leu Asp Ala Trp Met Phe Gly Asp Trp
1               5                   10

<210> SEQ ID NO 25
<211> LENGTH: 4991
<212> TYPE: DNA
<213> ORGANISM: Bacillus globisporus N75
<220> FEATURE:
<221> NAME/KEY: CDS
<222> LOCATION: (466)..(4326)

<400> SEQUENCE: 25
ggtaccggct tgtcgacgg  cttcgatgcg gcaggcgatg cagtgacctt cgacgtatcc      60
gtcaaagcgg ccggcacgta tgcgctcaag gtccggtacg cttccgctgg tgcaacgct     120 tcacgcgcta tctatgtcaa caacgccaag gtgaccgatc tggcgcttcc ggcaacggcc    180
aactgggaca cctgggggac ggcaaccgtc aacgtagcct taaacgccgg ctacaactcg    240
atcaaggtca gctacgacaa caccaatacg ctcggcatta atctcgataa cattgcgatc    300
gtggagcatt gacagcagga atcttcgcga ggaatgagtt agcgaagagt tcatgcaggc    360 agagggggtta cccataattg taaagcccgg cgcagccagg caccaagtat gcccgggagg    420
gccgccggcc ctccctttat ttcaatgatg aaaggcggca tcgat atg ggt cta tgg    477
                                                  Met Gly Leu Trp
                                                  1 aac aaa cga gtc act cgc atc ctc tcc gta ctc gca gca agc gcg ctg      525
Asn Lys Arg Val Thr Arg Ile Leu Ser Val Leu Ala Ala Ser Ala Leu
5                   10                  15                  20 atc ggc tct acc gta cct tct cta gcg cca cct ccc gct caa gcc cat      573
Ile Gly Ser Thr Val Pro Ser Leu Ala Pro Pro Pro Ala Gln Ala His
                25                  30                  35 gtg agc gcg ctg ggc aac ctg ctt tcc tcg gcg gtg acc ggg gat acg      621
Val Ser Ala Leu Gly Asn Leu Leu Ser Ser Ala Val Thr Gly Asp Thr
            40                  45                  50 ctc acg ctg acg atc gat aac ggc gcg gaa ccg aat gac gat att cta      669
Leu Thr Leu Thr Ile Asp Asn Gly Ala Glu Pro Asn Asp Asp Ile Leu
        55                  60                  65 gtt ctg caa gca gtc cag aac ggt att ctg aag gtg gac tac cgg ccg      717
Val Leu Gln Ala Val Gln Asn Gly Ile Leu Lys Val Asp Tyr Arg Pro
    70                  75                  80 aac ggt gta gct cca agc gcg gat acg ccg atg ctg gat ccc aat aaa      765
Asn Gly Val Ala Pro Ser Ala Asp Thr Pro Met Leu Asp Pro Asn Lys
85                  90                  95                 100 acc tgg ccg tcc ata ggc gcc gtt atc aat aca gcc tct aat ccg atg      813
Thr Trp Pro Ser Ile Gly Ala Val Ile Asn Thr Ala Ser Asn Pro Met
                105                 110                 115 acg atc aca acg ccg gcg atg aag att gag att gcc aaa aat ccg gtg      861
Thr Ile Thr Thr Pro Ala Met Lys Ile Glu Ile Ala Lys Asn Pro Val
            120                 125                 130 cgc ctg acc gtg aaa aaa ccg gac ggc acc gct ctg tta tgg gaa ccc      909
Arg Leu Thr Val Lys Lys Pro Asp Gly Thr Ala Leu Leu Trp Glu Pro
        135                 140                 145 ccg acc ggc ggc gtc ttc tcg gac ggc gtc cgt ttc ttg cac ggg acg      957
Pro Thr Gly Gly Val Phe Ser Asp Gly Val Arg Phe Leu His Gly Thr
    150                 155                 160
```

| | | |
|---|---|---|
| ggc gac aat atg tac ggc atc cgc agc ttc aat gct ttt gac agc ggc<br>Gly Asp Asn Met Tyr Gly Ile Arg Ser Phe Asn Ala Phe Asp Ser Gly<br>165                        170                      175                     180 | 1005 |
| ggg gat ctg ctg cgc aac agc tcc acc caa gcc gcc cgt gca ggc gac<br>Gly Asp Leu Leu Arg Asn Ser Ser Thr Gln Ala Ala Arg Ala Gly Asp<br>                    185                      190                      195 | 1053 |
| cag ggc aac tcc ggc ggc ccg ctg atc tgg agc aca gcc ggg tac ggg<br>Gln Gly Asn Ser Gly Gly Pro Leu Ile Trp Ser Thr Ala Gly Tyr Gly<br>                200                      205                      210 | 1101 |
| gtg ctc gtt gac agc gac ggt ggg tat ccg ttc acg gac gag gct acc<br>Val Leu Val Asp Ser Asp Gly Gly Tyr Pro Phe Thr Asp Glu Ala Thr<br>                215                      220                      225 | 1149 |
| ggc aag ctg gag ttc tat tac ggc ggc acg cct ccg gaa ggc cgg cgc<br>Gly Lys Leu Glu Phe Tyr Tyr Gly Gly Thr Pro Pro Glu Gly Arg Arg<br>230                        235                      240 | 1197 |
| tat acg aag cag gat gtg gag tac tac atc atg ctc ggc acg ccg aaa<br>Tyr Thr Lys Gln Asp Val Glu Tyr Tyr Ile Met Leu Gly Thr Pro Lys<br>245                        250                      255                      260 | 1245 |
| gag atc atg tcc ggc gtc ggg gaa att acg ggc aaa ccg ccg atg ctg<br>Glu Ile Met Ser Gly Val Gly Glu Ile Thr Gly Lys Pro Pro Met Leu<br>                    265                      270                      275 | 1293 |
| ccc aag tgg tcc ctg ggc ttt atg aac ttc gag tgg gat ctg aat gaa<br>Pro Lys Trp Ser Leu Gly Phe Met Asn Phe Glu Trp Asp Leu Asn Glu<br>                280                      285                      290 | 1341 |
| gct gag ctc aag aac cat gtg gat acg tac cgg gcc aaa aat att ccg<br>Ala Glu Leu Lys Asn His Val Asp Thr Tyr Arg Ala Lys Asn Ile Pro<br>295                        300                      305 | 1389 |
| atc gac ggc tat gcg atc gat ttc gat tgg aag aag tac ggc gag aat<br>Ile Asp Gly Tyr Ala Ile Asp Phe Asp Trp Lys Lys Tyr Gly Glu Asn<br>310                        315                      320 | 1437 |
| aat tac ggc gaa ttc gct tgg aat acg gcc aat ttc cct tcc gcc gcc<br>Asn Tyr Gly Glu Phe Ala Trp Asn Thr Ala Asn Phe Pro Ser Ala Ala<br>325                        330                      335                      340 | 1485 |
| acg acg gcg ctg aag tcg cag atg gac gcc aag ggc att aaa atg atc<br>Thr Thr Ala Leu Lys Ser Gln Met Asp Ala Lys Gly Ile Lys Met Ile<br>                    345                      350                      355 | 1533 |
| ggc ata acc aag cct cgc atc gcg acg aag gat ttt tcg aac aat cct<br>Gly Ile Thr Lys Pro Arg Ile Ala Thr Lys Asp Phe Ser Asn Asn Pro<br>                    360                      365                      370 | 1581 |
| acc gtg cag gga acg gac gcg gcg agc ggc ggt tat ttt tat ccg gga<br>Thr Val Gln Gly Thr Asp Ala Ala Ser Gly Gly Tyr Phe Tyr Pro Gly<br>                375                      380                      385 | 1629 |
| cat agc gaa tac aag gac tac ttc atc ccg gtc ttt gtg cgc agc atc<br>His Ser Glu Tyr Lys Asp Tyr Phe Ile Pro Val Phe Val Arg Ser Ile<br>390                        395                      400 | 1677 |
| gac cct tat aac cct gct gca cgc tcc tgg ttc tgg aac cac tcc aag<br>Asp Pro Tyr Asn Pro Ala Ala Arg Ser Trp Phe Trp Asn His Ser Lys<br>405                        410                      415                      420 | 1725 |
| gat gcg ttc gat aaa ggc atc gta ggc tgg tgg aac gac gag acg gat<br>Asp Ala Phe Asp Lys Gly Ile Val Gly Trp Trp Asn Asp Glu Thr Asp<br>                    425                      430                      435 | 1773 |
| gcg gta tcg tcg gga ggg gcc tcc tac tgg ttc ggc aat ttt acg acc<br>Ala Val Ser Ser Gly Gly Ala Ser Tyr Trp Phe Gly Asn Phe Thr Thr<br>                    440                      445                      450 | 1821 |
| ggc cat atg tcc cag gcg ctt tac gag gga cag cgg gca tat acg tcg<br>Gly His Met Ser Gln Ala Leu Tyr Glu Gly Gln Arg Ala Tyr Thr Ser<br>                455                      460                      465 | 1869 |
| aac gcc cag cgc gtc tgg cag aca gcg cgc acg ttc tat ccc ggg gcg<br>Asn Ala Gln Arg Val Trp Gln Thr Ala Arg Thr Phe Tyr Pro Gly Ala<br>470                        475                      480 | 1917 |

```
cag cgt tat gcg acg acg ctc tgg tcg gga gac atc ggg att cag tat    1965
Gln Arg Tyr Ala Thr Thr Leu Trp Ser Gly Asp Ile Gly Ile Gln Tyr
485                 490                 495                 500 acc aag ggg gaa aga atc aac tgg gct gcc ggc atg cag gag cag cgg    2013
Thr Lys Gly Glu Arg Ile Asn Trp Ala Ala Gly Met Gln Glu Gln Arg
                505                 510                 515 gcg gtg atg ctt tct tcg atc aac aac ggc cag gtc aaa tgg gga atg    2061
Ala Val Met Leu Ser Ser Ile Asn Asn Gly Gln Val Lys Trp Gly Met
        520                 525                 530 gac aca ggc ggc ttc aac cag cag gac ggc acg acg aac aat ccg aat    2109
Asp Thr Gly Gly Phe Asn Gln Gln Asp Gly Thr Thr Asn Asn Pro Asn
                535                 540                 545 ccg gac ctg tac gcc aga tgg atg cag ttc agc gcg ctg act ccg gtg    2157
Pro Asp Leu Tyr Ala Arg Trp Met Gln Phe Ser Ala Leu Thr Pro Val
550                 555                 560 ttc cgc gtg cat ggc aac aat cac cag cag cgc cag cct tgg tat tat    2205
Phe Arg Val His Gly Asn Asn His Gln Gln Arg Gln Pro Trp Tyr Tyr
565                 570                 575                 580 ggc tcg aca gcc gag gag gca tcc aag gaa gcg ctc cag ctc cgt tac    2253
Gly Ser Thr Ala Glu Glu Ala Ser Lys Glu Ala Leu Gln Leu Arg Tyr
                585                 590                 595 tcc ctg att cct tat atg tat gct tac gaa aga agc gcc tac gag aac    2301
Ser Leu Ile Pro Tyr Met Tyr Ala Tyr Glu Arg Ser Ala Tyr Glu Asn
                600                 605                 610 ggt aac gga ctt gtc cgg ccg ctg atg cag gaa tac cct gcc gat gcc    2349
Gly Asn Gly Leu Val Arg Pro Leu Met Gln Glu Tyr Pro Ala Asp Ala
            615                 620                 625 aac gcc aaa aac tat ctc gat gcc tgg atg ttc ggc gat tgg ctg ctg    2397
Asn Ala Lys Asn Tyr Leu Asp Ala Trp Met Phe Gly Asp Trp Leu Leu
630                 635                 640 gcg gcg cct gtg gtc gag aag cag cag acc tcc aag gaa atc tat ctc    2445
Ala Ala Pro Val Val Glu Lys Gln Gln Thr Ser Lys Glu Ile Tyr Leu
645                 650                 655                 660 cct gca ggc act tgg att gac tac aac cgg ggc acg gtg ctc acc ggc    2493
Pro Ala Gly Thr Trp Ile Asp Tyr Asn Arg Gly Thr Val Leu Thr Gly
                665                 670                 675 ggc cag aag atc agc tac gcc gtc aat ccc gac acg ctg acg gat att    2541
Gly Gln Lys Ile Ser Tyr Ala Val Asn Pro Asp Thr Leu Thr Asp Ile
                680                 685                 690 ccg ctc ttc att aag aag ggc gcg att atc cct tcg cag aag gtg cag    2589
Pro Leu Phe Ile Lys Lys Gly Ala Ile Ile Pro Ser Gln Lys Val Gln
        695                 700                 705 gac tac gtg ggc cag gct ccc gtc caa acg gtg gat gtg gat gta ttc    2637
Asp Tyr Val Gly Gln Ala Pro Val Gln Thr Val Asp Val Asp Val Phe
710                 715                 720 ccg aat acg gca caa tcg agc ttt acc tat tat gac gat gac ggc agc    2685
Pro Asn Thr Ala Gln Ser Ser Phe Thr Tyr Tyr Asp Asp Asp Gly Ser
725                 730                 735                 740 agc tac aat tat gaa agc gga gct tac ttc aag caa ttg atg acg gct    2733
Ser Tyr Asn Tyr Glu Ser Gly Ala Tyr Phe Lys Gln Leu Met Thr Ala
                745                 750                 755 cag gac aac gga tcc ggt gcg ctg agc ttt acg ctg ggc gcc aaa acc    2781
Gln Asp Asn Gly Ser Gly Ala Leu Ser Phe Thr Leu Gly Ala Lys Thr
                760                 765                 770 ggc acg tac agc ccc gca ctg caa tcc tat atc gtc aag ctt cac ggg    2829
Gly Thr Tyr Ser Pro Ala Leu Gln Ser Tyr Ile Val Lys Leu His Gly
            775                 780                 785 gcc gca ggc gcg tcg gtg aca agc aat ggg gcg gcg ctg gcc tcc tat    2877
Ala Ala Gly Ala Ser Val Thr Ser Asn Gly Ala Ala Leu Ala Ser Tyr
```

```
              790                 795                 800
gcc agc ctg caa gcg ctg aaa gcc tca gcc agt gaa ggc tgg gcc aag   2925
Ala Ser Leu Gln Ala Leu Lys Ala Ser Ala Ser Glu Gly Trp Ala Lys
805                 810                 815                 820 ggc aag gac atc tac ggc gat gtc acg tat gtc aag cta tcc gcg ggg   2973
Gly Lys Asp Ile Tyr Gly Asp Val Thr Tyr Val Lys Leu Ser Ala Gly
                825                 830                 835 gca gcg gcg gcc aag gcg att gcc gtc acc ggc aac agc ccg gtc agc   3021
Ala Ala Ala Ala Lys Ala Ile Ala Val Thr Gly Asn Ser Pro Val Ser
            840                 845                 850 gtg gcg gat gtg cag tac gaa gcc gaa gaa gct tcg ctg tcc ggc aat   3069
Val Ala Asp Val Gln Tyr Glu Ala Glu Glu Ala Ser Leu Ser Gly Asn
        855                 860                 865 acg aca gca acc aag gcg acc gtg aat acg aac cac gca ggc tac acg   3117
Thr Thr Ala Thr Lys Ala Thr Val Asn Thr Asn His Ala Gly Tyr Thr
    870                 875                 880 ggc agc ggc ttc gtg gat gga ctg agt aat ccg gga gcg gcg gtt acg   3165
Gly Ser Gly Phe Val Asp Gly Leu Ser Asn Pro Gly Ala Ala Val Thr
885                 890                 895                 900 ttc tat ccg aag gtg aaa acg ggc gga gac tac aat gtc tcg ctg cgc   3213
Phe Tyr Pro Lys Val Lys Thr Gly Gly Asp Tyr Asn Val Ser Leu Arg
                905                 910                 915 tac gct aat tcg acg gga gcg gca aag agc gtc agc atc ttc gtt aac   3261
Tyr Ala Asn Ser Thr Gly Ala Ala Lys Ser Val Ser Ile Phe Val Asn
            920                 925                 930 ggc aag cgc gtc aaa tcc acg tcg ctg gcg aac ctg ccg aac tgg gat   3309
Gly Lys Arg Val Lys Ser Thr Ser Leu Ala Asn Leu Pro Asn Trp Asp
        935                 940                 945 acg tgg ggg acg cag gct gag aca ctg ccg ctg acg gcg ggg acg aac   3357
Thr Trp Gly Thr Gln Ala Glu Thr Leu Pro Leu Thr Ala Gly Thr Asn
    950                 955                 960 gtt gtc acc tac aag ttc tac tcg gat gcc gga gat acg ggc tcg gtt   3405
Val Val Thr Tyr Lys Phe Tyr Ser Asp Ala Gly Asp Thr Gly Ser Val
965                 970                 975                 980 aac ctg gac aac atc acg gtg ccc ttc gct ccg gcc atc ggc aaa tac   3453
Asn Leu Asp Asn Ile Thr Val Pro Phe Ala Pro Ala Ile Gly Lys Tyr
                985                 990                 995 gag gcg gag agc  gcc gag ctg agc ggc  ggc agc acg gtc aac cag     3498
Glu Ala Glu Ser  Ala Glu Leu Ser Gly  Gly Ser Thr Val Asn Gln
            1000                 1005                1010 aat cat tgg ttc  tac agc ggc acg gca  ttt gta gat ggc tta acc     3543
Asn His Trp Phe  Tyr Ser Gly Thr Ala  Phe Val Asp Gly Leu Thr
        1015                 1020                1025 gca ccg ggc gcc  caa gtc aaa tat acc  gtg aac gcc ccg gcc gca     3588
Ala Pro Gly Ala  Gln Val Lys Tyr Thr  Val Asn Ala Pro Ala Ala
    1030                 1035                1040 ggc agc tac cag  atc gcg ctt cgc tat  gcg aac ggc acg ggt gct     3633
Gly Ser Tyr Gln  Ile Ala Leu Arg Tyr  Ala Asn Gly Thr Gly Ala
1045                 1050                1055 gcg aag acg ctc  agc acg tat gtg aac  ggg acg aag ctg ggg caa     3678
Ala Lys Thr Leu  Ser Thr Tyr Val Asn  Gly Thr Lys Leu Gly Gln
    1060                 1065                1070 acg gcc ttc gcc  agc cct ggc ggc aac  tgg aac gtg tgg cag gac     3723
Thr Ala Phe Ala  Ser Pro Gly Gly Asn  Trp Asn Val Trp Gln Asp
1075                 1080                1085 agc gtg cag acc  gtc gcg ctc gcc gcc  ggt acg aac acg atc gcg     3768
Ser Val Gln Thr  Val Ala Leu Ala Ala  Gly Thr Asn Thr Ile Ala
    1090                 1095                1100 ttc aag tac gat  gcc ggc gac agc ggc  agc ggc agc gtc aat ctg     3813
```

```
                Phe Lys Tyr Asp Ala Gly Asp Ser Gly Ser Gly Ser Val Asn Leu
                            1105                1110                1115 gac cgt ctg ttg ctc tct gcc gca gcg cca ggc gtg ccc gtg tcc         3858
Asp Arg Leu Leu Leu Ser Ala Ala Ala Pro Gly Val Pro Val Ser
            1120                1125                1130 gag cag aac ctg ctc gat aac ggg ggc ttt gaa cgc gat ccg tcg         3903
Glu Gln Asn Leu Leu Asp Asn Gly Gly Phe Glu Arg Asp Pro Ser
            1135                1140                1145 cag agc agc aac tgg acc gag tgg cat ccg gct tcg cag gcg att         3948
Gln Ser Ser Asn Trp Thr Glu Trp His Pro Ala Ser Gln Ala Ile
            1150                1155                1160 gct tac ggc atc gac agc ggc tcc ggg atg aat ccg cct gaa tcg         3993
Ala Tyr Gly Ile Asp Ser Gly Ser Gly Met Asn Pro Pro Glu Ser
            1165                1170                1175 cca tgg gca ggc gat aag cgc gcc tat ttc tat gcg gca ggc ccg         4038
Pro Trp Ala Gly Asp Lys Arg Ala Tyr Phe Tyr Ala Ala Gly Pro
            1180                1185                1190 tat cag caa agc atc cat caa aca gtc agc gtg cct gtc aat aat         4083
Tyr Gln Gln Ser Ile His Gln Thr Val Ser Val Pro Val Asn Asn
            1195                1200                1205 gcc aag tac aag ttc gaa gcc tgg gta ttg ctg aag aat aca aca         4128
Ala Lys Tyr Lys Phe Glu Ala Trp Val Leu Leu Lys Asn Thr Thr
            1210                1215                1220 ccg aca acg gcc cgg gtg gag att caa aat tac ggc ggt tcg ccg         4173
Pro Thr Thr Ala Arg Val Glu Ile Gln Asn Tyr Gly Gly Ser Pro
            1225                1230                1235 atc ttc acg aac atc agt aaa gac ggc gtc tgg aaa tac atc agc         4218
Ile Phe Thr Asn Ile Ser Lys Asp Gly Val Trp Lys Tyr Ile Ser
            1240                1245                1250 gtc agc gat att cag gtc acg aac ggc caa atc gat att ggc ttc         4263
Val Ser Asp Ile Gln Val Thr Asn Gly Gln Ile Asp Ile Gly Phe
            1255                1260                1265 tat gtg gat tcg ccc gga ggc acg acg ctc cac atc gac gat gtg         4308
Tyr Val Asp Ser Pro Gly Gly Thr Thr Leu His Ile Asp Asp Val
            1270                1275                1280 cgg gtc acc aag caa taa tccggtaaca ctagccctcc cccgccttgc            4356
Arg Val Thr Lys Gln
            1285 ggcaggaggg cttttttgctt ctgtaggttg tgaaggcgat accgagcgat gagaattcga   4416 ttctgaacag ctcgccctgt gtcctgctaa attcctctcc tccctggcag ggaagccgct   4476 tccacatgtc gaattgggga ggtactatga gaagttagta ctaccgtctg caacggcttt   4536 cgctacaatg gaaccaataa gacatcgcga aggtttggga ggattcggca tgcagagacg   4596 cgaggttaaa gtaataggca cgggcaaata tttgcccgcc catcgagtga ctgcgcagga   4656 gatggaccgg cggctaggag tgcccgacgg atgggtgctg aagaagtcgg atgtggccgt   4716 tcgttatttc gccggtacgg agaaggcctc ggagatgggg gcgagagcgg ctgaggcggc   4776 gctggcttcc gcaggcctgg ccttcacgga tatcgactgc ctgatgtgcg ccagcgggac   4836 gatggaacag ccgattccat gcacggcggc gctcattcag aaggcgatag gccaaggaca   4896 ctccggagtg ccggcactgg atttgaatac aacctgtctg agctttgtgg cggctctgga   4956 catggtttct tatatggtga cggcgggaag gtacc                              4991

<210> SEQ ID NO 26
<211> LENGTH: 13
<212> TYPE: PRT
<213> ORGANISM: Arthrobacter globiformis A19
```

```
<400> SEQUENCE: 26

Ala Pro Leu Gly Val Gln Arg Ala Gln Phe Gln Ser Gly
1               5                   10

<210> SEQ ID NO 27
<211> LENGTH: 13
<212> TYPE: PRT
<213> ORGANISM: Arthrobacter globiformis A19

<400> SEQUENCE: 27

Gln Glu Trp Asn Leu Thr Gly Asp Pro Trp Thr Val Arg
1               5                   10

<210> SEQ ID NO 28
<211> LENGTH: 30
<212> TYPE: PRT
<213> ORGANISM: Arthrobacter globiformis A19

<400> SEQUENCE: 28

Ile Ala Asp Leu Ala Glu Asp Gly Val Gly Ile Ile Pro Ile Glu Glu
1               5                   10                  15

Ser Tyr Val Gly Arg Asn Leu Pro Glu His Ala Arg Met Ala
            20                  25                  30

<210> SEQ ID NO 29
<211> LENGTH: 30
<212> TYPE: PRT
<213> ORGANISM: Arthrobacter globiformis A19

<400> SEQUENCE: 29

Gly Gly Met Ile Asp Trp Thr Gln Pro Glu Ala Gly Ala Val Trp His
1               5                   10                  15

Asp Glu Gln Arg Gln His Leu Val Asp Glu Gly Val Leu Gly
            20                  25                  30

<210> SEQ ID NO 30
<211> LENGTH: 27
<212> TYPE: PRT
<213> ORGANISM: Arthrobacter globiformis A19

<400> SEQUENCE: 30

His Asp Tyr Ala Gly Pro Asp Val Phe Thr Gln Thr Gly Ser Val Leu
1               5                   10                  15

Gln Thr Ala Ala Met Arg Ile Glu Val Asp Pro
            20                  25

<210> SEQ ID NO 31
<211> LENGTH: 27
<212> TYPE: PRT
<213> ORGANISM: Arthrobacter globiformis A19

<400> SEQUENCE: 31

Met Leu Gly Arg Asp Leu Leu Ile Ala Ile Val Ala Gly Glu Gly Glu
1               5                   10                  15

Arg Glu Arg Asp Val Tyr Leu Pro Ala Gly Glu
            20                  25

<210> SEQ ID NO 32
<211> LENGTH: 5811
<212> TYPE: DNA
<213> ORGANISM: Arthrobacter globiformis A19
<220> FEATURE:
<221> NAME/KEY: CDS
```

<222> LOCATION: (1655)..(4552)

<400> SEQUENCE: 32

```
ggtacctcgt cgaggagctc ggtgtcgacg gcttcaagac cgacgggagc gaggcgctct      60
tcgggcgtga cctgatcgtc agcgacgggc gccgcggtga cgagatgcac aacgcctacc     120
cgaacgagta cacctccgcc tacaacgact tcgtgcagga gacgacgggc gccgacggca     180
cgatcttcag ccgggcgggc acctccggcg gccagagcga atccatcttc tgggccgggg     240
accaggcgtc gacgttcggc gctttccagg aggccgtccg ggccgggcag agcgcgggcc     300
agtcgggagt gccgttctgg gcctgggacc tcggcggctt caccgggtcg ttcccaagcg     360
cggagctgta tctgcgctcg accgctcagg cggtgttctc gccgatcatg cagtaccact     420
cggagaaggc cgaccccagt ccgtccgagg cgcgcacgcc ctggaacgtg caggcgcgca     480
ccgggaacac cactgtcgtc cccaccttcg cccgttacgc gaacgtacgg atgaacctcg     540
tgccctatct gtacacggag gcggacgaca cgcgacgac gggtgtgccg atgatgcgcg     600
cgatgagcct cgcgttcccc gacgacccgg atgccgcgca gtacgaccag cagtacatgt     660
tcgggtctca gctgctggtc gcaccgatta cgaaccaggg ccagaccgtg aaagacgtct     720
acctgcccgc gggcgagtgg tacgacttct ggaacggcgg acgcgcgagc ggcgagggcg     780
tgaagatgta cgacgccgga cccgacggca tccccgtata cgctcgcgcc ggagcggtca     840
tcccgctcaa cctcaacgac gcgtatgagg tgggcggcac gatcggcaac gacgtggaga     900
gctacgacaa ccttgtgttc cgcgtttacc cctccggtga gagcagctac gagtacttcg     960
aagaccaagc gaacgcgcac cgccggatcg atgtctcggc cgaccgcgca gcgcgcacgg    1020
tcgaggtgtc tgctcccgcg ctcacgaccg cgagcacctt ccaggtgtcg ggcaccaagc    1080
ccgacaccgt gaccgtcgcg ggctcggcac tgcctgaggt caacagcgtg agcgcgctgg    1140
ccgcatccac cgaggcctgg tactgggatg cgaagcagca gctgacgtac gtgaaggtcg    1200
gtgcgagcac cggcgagcgc acgatcctcc tgctgggcgt cgacaaggcc gggtacgagg    1260
ccgagttcgc gggtcatacg gccgtctcga cgaacgccga ccaccggggc tacaccgggc    1320
tcggcttcgt cgacggcttc gcgaacgcag gagacgcggt ggagttcgac gtgtgggccg    1380
aggagaacgg cgcgcaccag ctccgcttcc gctacggaaa cggagcggcg accccgccca    1440
cccgcacgat ccgggtcgac ggagcgcctc tgggaacgct gtcgcttccg cccaccgggt    1500
cgtggagttc gtggggcacg gcctcgatcg acgtgaccct cccacccgga cgccacgccg    1560 tacgatcga gtacgccgga ggcgattccg gcggcgtcaa cctcgacaac ctcgtcctcg    1620
cgcgctgagc gcacacggga aagggagaag aacc atg cct gct ctt ccg tgg cgc   1675
                                    Met Pro Ala Leu Pro Trp Arg
                                      1               5 cgc acg acg gcg ctc gcg ctc acc acg gcg gtg acg gcc gcg acc ctg     1723
Arg Thr Thr Ala Leu Ala Leu Thr Thr Ala Val Thr Ala Ala Thr Leu
         10                  15                  20 gtc gcc gtc ggg gtg aac gac gcc ggt cag gcg gcg gct gct ccc ctg     1771
Val Ala Val Gly Val Asn Asp Ala Gly Gln Ala Ala Ala Ala Pro Leu
 25                  30                  35 ggc gtg caa cgc gcg cag ttc cag tcg ggg tcg agc tac ctc gtc gtc     1819
Gly Val Gln Arg Ala Gln Phe Gln Ser Gly Ser Ser Tyr Leu Val Val
40                  45                  50                  55 gag gtg ctc gat gac gac ctc gtc cac ttc gag ctg gcc ggg ggc ggc     1867
Glu Val Leu Asp Asp Asp Leu Val His Phe Glu Leu Ala Gly Gly Gly
                 60                  65                  70 acc gcc ccc ggc acg ggc tcc ccg ctg ttc acg acg cct cag gtc gcg     1915
```

-continued

```
                Thr Ala Pro Gly Thr Gly Ser Pro Leu Phe Thr Thr Pro Gln Val Ala
                         75                  80                  85 aag cac gac tac gcg gga ccc gac gtg ttc acc cag acc ggg tct gtt        1963
Lys His Asp Tyr Ala Gly Pro Asp Val Phe Thr Gln Thr Gly Ser Val
             90                  95                 100 ctg cag acc gcg gcg atg cgc atc gag gtc gat ccc gcg gat ctg tgc        2011
Leu Gln Thr Ala Ala Met Arg Ile Glu Val Asp Pro Ala Asp Leu Cys
    105                 110                 115 gtg acg gcc acc gac atc acc cgc acc ccg aac ctt gta ctg cac gag        2059
Val Thr Ala Thr Asp Ile Thr Arg Thr Pro Asn Leu Val Leu His Glu
120                 125                 130                 135 gcg tgt ccc gcc gac ctc ggc cag gcg tgg aag ggg ctg aac atc acg        2107
Ala Cys Pro Ala Asp Leu Gly Gln Ala Trp Lys Gly Leu Asn Ile Thr
                140                 145                 150 agg tcg gcg atg gag aac gcc tac ggt ctc ggg cag cag ttc ttc acg        2155
Arg Ser Ala Met Glu Asn Ala Tyr Gly Leu Gly Gln Gln Phe Phe Thr
            155                 160                 165 ggc ggc agc gcg gac ggc gac tgg gtg ggc cgc acc cgc acc ccg ggt        2203
Gly Gly Ser Ala Asp Gly Asp Trp Val Gly Arg Thr Arg Thr Pro Gly
        170                 175                 180 ggc acc tac ggc aac gcg atg gtg ttc gac ccc gag aac ggg ccg gtc        2251
Gly Thr Tyr Gly Asn Ala Met Val Phe Asp Pro Glu Asn Gly Pro Val
    185                 190                 195 ggc aac acg cag atc ccg gtg ctc ttc gcg gtc ggc gat gac aac gcg        2299
Gly Asn Thr Gln Ile Pro Val Leu Phe Ala Val Gly Asp Asp Asn Ala
200                 205                 210                 215 aac tac ggg ctg ttc gtc gat cag ctg tac aag cag gaa tgg aac ctc        2347
Asn Tyr Gly Leu Phe Val Asp Gln Leu Tyr Lys Gln Glu Trp Asn Leu
                220                 225                 230 acc ggc gac ccg tgg acg gtg cgc atg tgg ggc gac cag gtg cgc tgg        2395
Thr Gly Asp Pro Trp Thr Val Arg Met Trp Gly Asp Gln Val Arg Trp
            235                 240                 245 tac ctc atg agc ggc gac gac ctg ccc gac ctt cgc cac gac tac atg        2443
Tyr Leu Met Ser Gly Asp Asp Leu Pro Asp Leu Arg His Asp Tyr Met
        250                 255                 260 gag ctg acg ggc acc ccg ccc gtg ccg ccg aag aag gcg ttc ggg ctc        2491
Glu Leu Thr Gly Thr Pro Pro Val Pro Pro Lys Lys Ala Phe Gly Leu
    265                 270                 275 tgg gtg tcg gag ttc ggc tac gac aac tgg agc gag gtc gac aat acg        2539
Trp Val Ser Glu Phe Gly Tyr Asp Asn Trp Ser Glu Val Asp Asn Thr
280                 285                 290                 295 atc gcg ggc ctg cgc tcg gcc gac ttt ccg gtc gat ggc gcg atg ctc        2587
Ile Ala Gly Leu Arg Ser Ala Asp Phe Pro Val Asp Gly Ala Met Leu
                300                 305                 310 gac gta cag tgg ttc ggg ggc gtc acc gcc gac tcg gac gac acc cgc        2635
Asp Val Gln Trp Phe Gly Gly Val Thr Ala Asp Ser Asp Asp Thr Arg
            315                 320                 325 atg ggc acc ctc gat tgg gac acg tcg agg ttt ccc gac cct gcg gga        2683
Met Gly Thr Leu Asp Trp Asp Thr Ser Arg Phe Pro Asp Pro Ala Gly
        330                 335                 340 aag atc gcc gac ctc gcc gag gac ggc gtc ggc atc atc ccg atc gag        2731
Lys Ile Ala Asp Leu Ala Glu Asp Gly Val Gly Ile Ile Pro Ile Glu
    345                 350                 355 gag tcg tac gtc ggt cgc aac ctg ccg gag cac gcc cgg atg gcg gcg        2779
Glu Ser Tyr Val Gly Arg Asn Leu Pro Glu His Ala Arg Met Ala Ala
360                 365                 370                 375 gac ggt tac ctc gtg cgc tcc ggc tgc gct acg tgc ccg ccg gtg tac        2827
Asp Gly Tyr Leu Val Arg Ser Gly Cys Ala Thr Cys Pro Pro Val Tyr
                380                 385                 390
```

-continued

```
ctg acg ggg aac ccc tgg tgg ggc aag ggc ggg atg atc gac tgg acg         2875
Leu Thr Gly Asn Pro Trp Trp Gly Lys Gly Gly Met Ile Asp Trp Thr
            395                 400                 405 cag ccg gaa gcc ggc gcc gtc tgg cac gac gag cag cgc cag cat ctc         2923
Gln Pro Glu Ala Gly Ala Val Trp His Asp Glu Gln Arg Gln His Leu
        410                 415                 420 gtc gac gag ggc gta ctg ggc cac tgg ctc gat ctc ggc gaa ccg gag         2971
Val Asp Glu Gly Val Leu Gly His Trp Leu Asp Leu Gly Glu Pro Glu
    425                 430                 435 atg tac gac ccg aac gac tgg acc gcc ggc gtc atc ccc ggc aag cac         3019
Met Tyr Asp Pro Asn Asp Trp Thr Ala Gly Val Ile Pro Gly Lys His
440                 445                 450                 455 gcg cac gcc gac tat cac aac gcg tac aac ctg ctg tgg gcg cag agc         3067
Ala His Ala Asp Tyr His Asn Ala Tyr Asn Leu Leu Trp Ala Gln Ser
                460                 465                 470 atc gcc gac ggg tac gcc gac aac ggc gtg cag aag cgt ccc ttc atg         3115
Ile Ala Asp Gly Tyr Ala Asp Asn Gly Val Gln Lys Arg Pro Phe Met
            475                 480                 485 ctg acg cgc gcc gcg gcc gcc ggc atc cag cgt cat ggc gcg ggc atg         3163
Leu Thr Arg Ala Ala Ala Ala Gly Ile Gln Arg His Gly Ala Gly Met
        490                 495                 500 tgg tca gcc gac atc ggg tcg acc atg aag gcg ctc ggg agc cag cag         3211
Trp Ser Ala Asp Ile Gly Ser Thr Met Lys Ala Leu Gly Ser Gln Gln
    505                 510                 515 aac gcg cag atg cac atg tcg atg tcg ggg atc gac tat tac ggc tcc         3259
Asn Ala Gln Met His Met Ser Met Ser Gly Ile Asp Tyr Tyr Gly Ser
520                 525                 530                 535 gac atc ggc ggg ttc cgg cgg gag atg gcc gac ggc gac gtg aac gag         3307
Asp Ile Gly Gly Phe Arg Arg Glu Met Ala Asp Gly Asp Val Asn Glu
                540                 545                 550 ctc tac acc cag tgg ttc gcc gac agc gcg tgg ttc gac act ccg ctc         3355
Leu Tyr Thr Gln Trp Phe Ala Asp Ser Ala Trp Phe Asp Thr Pro Leu
            555                 560                 565 cgg ccg cac acc gac aat ctc tgc aac tgc ctc gag acg agc ccc gac         3403
Arg Pro His Thr Asp Asn Leu Cys Asn Cys Leu Glu Thr Ser Pro Asp
        570                 575                 580 tcg atc ggc gac gtc gcg agc aac cgc gag aac ctg gtg cgc cgc tac         3451
Ser Ile Gly Asp Val Ala Ser Asn Arg Glu Asn Leu Val Arg Arg Tyr
    585                 590                 595 gag ctg gct ccg tac tac tac tcg ctc gcg cac cgc gct cac cag ttc         3499
Glu Leu Ala Pro Tyr Tyr Tyr Ser Leu Ala His Arg Ala His Gln Phe
600                 605                 610                 615 ggc gag ccg ctc gct ccc ccg ctc gtg tac tac tac cag aac gac gac         3547
Gly Glu Pro Leu Ala Pro Pro Leu Val Tyr Tyr Tyr Gln Asn Asp Asp
                620                 625                 630 cac gtt cgc gag atg ggg cat cag aag atg ctc ggg cgc gac ctg ctg         3595
His Val Arg Glu Met Gly His Gln Lys Met Leu Gly Arg Asp Leu Leu
            635                 640                 645 atc gcg atc gtc gcc gga gag ggc gag cgg gaa cgc gac gtg tac ctt         3643
Ile Ala Ile Val Ala Gly Glu Gly Glu Arg Glu Arg Asp Val Tyr Leu
        650                 655                 660 ccg gcg ggc gag tgg atc gac atc cac acg aac gag cgc atc cag agc         3691
Pro Ala Gly Glu Trp Ile Asp Ile His Thr Asn Glu Arg Ile Gln Ser
    665                 670                 675 acg ggt cag tgg atc gac aac gtg ccg ctg tgg cgt gac ggc gtc ttc         3739
Thr Gly Gln Trp Ile Asp Asn Val Pro Leu Trp Arg Asp Gly Val Phe
680                 685                 690                 695 acc ctg ccg gcg tac gcc cgg gcg ggg gcg atc atc ccg aag gcc ttc         3787
Thr Leu Pro Ala Tyr Ala Arg Ala Gly Ala Ile Ile Pro Lys Ala Phe
                700                 705                 710
```

-continued

| | | |
|---|---|---|
| gtc gac gcc tcc acg aag gac atc acc ggc aag cgc gag gat gcc gcg<br>Val Asp Ala Ser Thr Lys Asp Ile Thr Gly Lys Arg Glu Asp Ala Ala<br>              715                    720                    725 | | 3835 |
| gtg cgc aac gag ctg atc gca acc gtt tac gcc gac gac gtc gcg agc<br>Val Arg Asn Glu Leu Ile Ala Thr Val Tyr Ala Asp Asp Val Ala Ser<br>730                    735                    740 | | 3883 |
| gac ttc acc ctg tac gag gat gac ggc gcg acg acc gca tac gcc gac<br>Asp Phe Thr Leu Tyr Glu Asp Asp Gly Ala Thr Thr Ala Tyr Ala Asp<br>745                    750                    755 | | 3931 |
| ggg gct gtc agg acc acg cag atc agc caa tcg ctc acg aac ggc gtg<br>Gly Ala Val Arg Thr Thr Gln Ile Ser Gln Ser Leu Thr Asn Gly Val<br>760                    765                    770                    775 | | 3979 |
| gcc acg gtg acg gtg gga gcg gca tct gga acc tac tcc ggt gcg ccc<br>Ala Thr Val Thr Val Gly Ala Ala Ser Gly Thr Tyr Ser Gly Ala Pro<br>                    780                    785                    790 | | 4027 |
| tcc acc cgt ccc acg gtc gtc gag ctt gtc act gac ggc acg cag gcc<br>Ser Thr Arg Pro Thr Val Val Glu Leu Val Thr Asp Gly Thr Gln Ala<br>              795                    800                    805 | | 4075 |
| tcg acc gtc tcc ctc ggc agc gtt ccg ctg acg gag cac gcg aac aag<br>Ser Thr Val Ser Leu Gly Ser Val Pro Leu Thr Glu His Ala Asn Lys<br>810                    815                    820 | | 4123 |
| gcg gcg ttc gac gcg gcg agc agc ggc tgg tac aac gcc ggc ggg ggg<br>Ala Ala Phe Asp Ala Ala Ser Ser Gly Trp Tyr Asn Ala Gly Gly Gly<br>825                    830                    835 | | 4171 |
| ctc gtt gtg gcc aag gcg gcg agc agt tcg gtg aac acc gcc aag acc<br>Leu Val Val Ala Lys Ala Ala Ser Ser Ser Val Asn Thr Ala Lys Thr<br>840                    845                    850                    855 | | 4219 |
| ttc tcg ttc acg ctc ggt gag gag tcg gtc tgg gcg acg ttc tcc tgc<br>Phe Ser Phe Thr Leu Gly Glu Glu Ser Val Trp Ala Thr Phe Ser Cys<br>                    860                    865                    870 | | 4267 |
| gag aac gcc acg acg acc ttc ggt cag tca gtg tac gtc gtc gga aat<br>Glu Asn Ala Thr Thr Thr Phe Gly Gln Ser Val Tyr Val Val Gly Asn<br>              875                    880                    885 | | 4315 |
| gtt ccg cag ctc ggc aac tgg tcg ccg gcg gat gcc gtg aag ctc gag<br>Val Pro Gln Leu Gly Asn Trp Ser Pro Ala Asp Ala Val Lys Leu Glu<br>890                    895                    900 | | 4363 |
| ccg agc gcc tac ccc acc tgg acc ggg gtg gtg cgg aac ctg ccg ccg<br>Pro Ser Ala Tyr Pro Thr Trp Thr Gly Val Val Arg Asn Leu Pro Pro<br>905                    910                    915 | | 4411 |
| tcg agc acg gtc gaa tgg aag tgc atc aaa cgt cag gag gcc ggc ctg<br>Ser Ser Thr Val Glu Trp Lys Cys Ile Lys Arg Gln Glu Ala Gly Leu<br>920                    925                    930                    935 | | 4459 |
| ccg aac acg gcg gat gcg tgg gag ccc ggc ggg aac aac atc ctc tcg<br>Pro Asn Thr Ala Asp Ala Trp Glu Pro Gly Gly Asn Asn Ile Leu Ser<br>                    940                    945                    950 | | 4507 |
| acg cca cct tcc ggc tcg gcg ggg ata acc acc ggc gcc ttc tga<br>Thr Pro Pro Ser Gly Ser Ala Gly Ile Thr Thr Gly Ala Phe<br>              955                    960                    965 | | 4552 |
| cccaggggg ctcgatcccg gtcgccagcg caagcgcggc gcccgggtc gacgcgtgtt | | 4612 |
| aggccagtac gcgaaggaac cagccctcta cgacaccggc ctcgaccccg ccgaaggact | | 4672 |
| ctggcaccgg tcaggctgga tcggacaaca ctgacacgcc ccgacgccat ccactctttt | | 4732 |
| tggcctacaa cccgttgtcg cacgtgcgcc tcttggcccg ggcacgacga aaccccgcg | | 4792 |
| atccagggat cggcgggggt tcggatggc ggtgacggtg ggatttgaac ccacggtagg | | 4852 |
| gggttaccct acacaacttt tcgagagttg caccttcggc cgctcggaca cgtcaccggg | | 4912 |
| gtcgagttta cgcgacgttc tcctggcgcg ccaatcggcg cgccccgcc cgcgagaatc | | 4972 |

-continued

```
caggcccgcg ccgagaatcc gcgggcgcct ggattctcag cacggggatg gattctcgcc    5032
gctcatccga gccccgcggc gagcgggctc agtgctcgtc ctccatgagc atgccgaccg    5092
aggtggcgca ggcgtcgccg cgccaggcct cgatgccctc gcgcacggcg aaggcggcga    5152
tgatgaggcc ggtgatcgcg tcggcccacc accagcccag gaggctgttg agcacgaggc    5212
ccgcgagcac ggccgccgac aggtaggtgc agatgagggt ctgcttcgag tcggccacgg    5272
cggtggccga tccgagctcg cggccggcgc ggcgctcggc gaacgacagg aacggcatga    5332
tcgccacgct gagcgccgtg atgacgatgc cgagcgtcga gtgctccacg tccgcgccgc    5392
cgacgagggc caggaccgac gtgacggtga cgtacgcggc gagcgcgaag aaggccacgg    5452
cgatgacgcg cagcgtgccg cgctcccagc gctccgggtc gcgccgcgtg aactgccacg    5512
cgacggcggc ggccgagagc acctcgatgg tcgagtccag gccgaacgcg acgagcgcgg    5572
ccgacgaggc cgcagctccc gcggcgatcg cgacgaccgc ctcgacgacg ttataggcga    5632
tggtcgcggc gacgatccag cggatgcgcc gctgcaggac ggatcgccga tcggcagacg    5692
cggtggcggt catgcgcagg tgcagctctc tccggcgcag cagccgggct cgacgtacag    5752
gacgacgcgc agcagctcgt cgagcgcggg cgcgaggtgg gcgtcggcca gccggtacc     5811
```

POLYPEPTIDE HAVING α-ISOMALTOSYLGLUCOSACCHARIDE SYNTHASE ACTIVITY

TECHNICAL FIELD

The present invention relates to a polypeptide which has an activity of forming α-isomaltosylglucosaccharides (which may be simply designated as "a polypeptide"), a process for preparing the polypeptide by gene recombinant technology, and uses thereof.

BACKGROUND ART

There have been known several carbohydrates which are composed of glucose molecules as constituents and produced from starches, amyloses, or partial starch hydrolyzates as amylaceous materials, for example, amylodextrins, maltodextrins, maltooligosaccharides, and isomaltooligosaccharides. These carbohydrates are also known to have usually both non-reducing and reducing groups at their molecular ends and the reducing group is responsible for reducibility. In general, reducing power of a partial starch hydrolyzate is represented with dextrose equivalent (DE), a scale for the reducing power, on a dry solid basis. Such a partial starch hydrolyzate with a high DE value has a low molecular weight, viscosity, strong sweetening power and reactivity: They easily react with amino group-containing substances such as amino acids and proteins through the amino carbonyl reaction which may lead to browning, undesirable smell, and deterioration. To overcome these disadvantages, heretofore long desired are methods which may lower or even eliminate the reducing power of partial starch hydrolyzates without converting glucose molecules as constituent saccharides. For example, it was reported in *Journal of the American Chemical Society*, Vol. 71, 353–358 (1949) that starches can be converted to α-, β- and γ-cyclodextrins which are composed of 6–8 glucose molecules linked covalently via the α-1,4 glucosidic linkage by allowing to contact with "macerans amylase". Nowadays, cyclodextrins are produced on an industrial scale and their inherent properties such as non-reducibility, tasteless, and clathrating abilities render them very useful in a variety of fields. While, for example, Japanese Patent Kokai Nos. 143,876/95 and 213,283/95, filed by the same applicant of the present invention discloses a method of producing trehalose, a disaccharide composed of two glucose molecules linked together via the α,α-linkage, where a non-reducing saccharide-forming enzyme and a trehalose-releasing enzyme are allowed to contact with partial starch hydrolyzates such as maltooligosaccharides. In these days, trehalose has been industrially produced from starches and applied to a variety of fields where its non-reducibility, mild- and high quality-sweetness are advantageously utilized. As described above, trehalose (DP of two) and α-, β- and γ-cyclodextrins (DP of 6–8) have been produced on an industrial scale and extensively used because of their advantageous properties; however, there is a limitation in the types of non- or low-reducing saccharides which are available in the art. Therefore, saccharides other than these saccharides are in great demand.

Recently, reported was a novel cyclic tetrasaccharide composed of glucose units: *European Journal of Biochemistry*, Vol.226, 641–648 (1994) reported that a cyclic tetrasaccharide with the structure of cyclo{→6)-α-D-glucopyranosyl-(1→3)-α-D-glucopyranosyl-(1→6)-α-D-glucopyranosyl-(1→3)-α-D-glucopyranosyl-(1→} (which may be simply designated as "cyclotetrasaccharide", hereinafter) is formed by allowing alternanase, a type of hydrolyzing enzyme, to contact with alternan, a polysaccharide where glucose molecules are linked via the alternating α-1,3 and α-1,6 bonds, followed by crystallization in the presence of methanol.

Cyclotetrasaccharide, a saccharide with a cyclic structure and no reducing power, is expected to be very useful because of its no amino-carbonyl reactivity, stabilizing effect for volatile organic compounds by its clathrating ability, and no apprehension of browning and deterioration.

However, alternan and alternanase, which are indispensable materials to produce cyclotetrasaccharide, are not easily obtainable, and microorganisms as alternanase source are not easily available.

Under these circumstances, the present inventors disclosed in WO 01/90338 A1 a successful process to produce cyclotetrasaccharide where a saccharide with a glucose polymerization degree of 3 or higher and bearing both the α-1,6 glucosidic linkage as a linkage at the non-reducing end and the α-1,4 glucosidic linkage other than the linkage at the non-reducing end (may be called "α-isomaltosylglucosaccharide" throughout the specification) as a material is allowed to contact with an α-isomaltosyl-transferring enzyme which specifically hydrolyzes the linkage between the α-isomaltosyl moiety and the resting glucosaccharide moiety, and then the enzyme transfers the released α-isomaltosyl moiety to another α-isomaltosylglucosaccharide to form cyclotetrasaccharide. The α-isomaltosyl-transferring enzyme forms cyclotetrasaccharide from α-isomaltosylglucosaccharide by α-isomaltosyl-transferring reaction. Particularly, α-isomaltosyl-transferring enzyme has the following physicochemical properties:

(1) Action

Forming cyclotetrasaccharide with the structure of cyclo{→6)-α-D-glucopyranosyl-(1→3)-α-D-glucopyranosyl-(1→6)-α-D-glucopyranosyl-(1 3)-α-D-glucopyranosyl-(1→} from a saccharide with a glucose polymerization degree of 3 or higher and bearing both the α-1,6 glucosidic linkage as a linkage at the non-reducing end and the α-1,4 glucosidic linkage other than the linkage at the non-reducing end by catalyzing α-isomaltosyl-transferring reaction;

(2) Molecular Weight

About 82,000 to 136,000 daltons when determined on sodium dodecyl sulfate polyacrylamide gel electrophoresis (SDS-PAGE);

(3) Isoelectric Point (pI)

About 3.7 to 8.3 when determined on isoelectrophoresis using ampholine;

(4) Optimum Temperature

About 45 to 50° C. when incubated at pH 6.0 for 30 minutes;

(5) Optimum pH

About 5.5 to 6.5 when incubated at 35° C. for 30 minutes;

(6) Thermal Stability

About 45° C. or lower when incubated at pH 6.0 for 60 minutes; and (7) pH Stability About 3.6 to 10.0 when incubated at 4° C. for 24 hours.

As regards to saccharides which are used as starting materials for cyclotetrasaccharide, it is desirable to prepare them from starches which are abundant and low-cost sources, however, since α-isomaltosyl-transferring enzyme dose not directly act on starches, the following procedures are actually employed: Starches are firstly converted into an α-isomaltosylglucosaccharide having the above specified structure, for example, relatively low-molecular weight isomaltooligosaccharide such as panose and isomaltosylmaltose, and then subjected to the action of α-isomaltosyl-transferring enzyme to form cyclotetrasaccharide. As regards to the yield of cyclotetrasaccharide from the materials, in the case of using panose as a material, the yield of cyclotetrasaccharide is about 44% based on the weight of the dry solid (d.s.b.). Similarly, in the case of using isomaltosylmaltose as a material, the yield of cyclotetrasaccharide is about 31%, d.s.b. While in the case of using starches as a material, it is necessary to contact starches previously with α-amylase, starch-debranching enzyme, β-amylase and α-glucosidase to form relatively low-molecular weight isomaltooligosaccharides including panose, and the yield of cyclotetrasaccharide is relatively low, about 15%, d.s.b. Although the production of cyclotetrasaccharide from starch is feasible even in such a low yield, the production cost may be increased. Therefore, it is desired to establish a novel method for producing cyclotetrasaccharide in a relatively high yield using starches as a material.

Under these circumstances, the present inventors extensively screened microorganisms capable of producing an α-isomaltosylglucosaccharide-forming enzyme which may significantly improve the yield of cyclotetrasaccharide when allowed to act on starches as a material. As a result, the present inventors found that α-isomaltosyl-transferring enzyme-producing microorganisms, strains C9, C11, N75 and A19 of the genera *Bacillus* and *Arthrobacter*, which are disclosed in WO 01/90338 A1, also produce another α-isomaltosylglucosaccharide-forming enzyme. They also found that the yield of cyclotetrasaccharide can be remarkably improved by allowing both α-isomaltosylglucosaccharide-forming enzyme and α-isomaltosyl-transferring enzyme to act on a glucosaccharide with a high-molecular weight such as partial starch hydrolyzates. The present inventors characterized the α-isomaltosylglucosaccharide-forming enzyme, and established a process for producing the enzyme. Further, they established methods for α-glucosyl-transferring reaction using the enzyme, a process for producing α-isomaltosylglucosaccharide, and a process for producing cyclotetrasaccharide and a saccharide composition containing the cyclotetrasaccharide by the combination use of the enzyme and α-isomaltosyl-transferring enzyme. Also, the present inventors established food products, cosmetics and pharmaceuticals, comprising cyclotetrasaccharide which are obtainable by the processes mentioned above or saccharide compositions containing cyclotetrasaccharide. However, since the producibility of α-isomaltosylglucosaccharide-forming enzyme in the microorganisms were found to be not enough, there has been still left a problem that large-scale cultivation of such microorganisms as enzyme sources are required for industrial scale production of α-isomaltosylglucosaccharide and cyclotetrasaccharide.

It is known that the entity of the enzyme is a polypeptide and the enzymatic activity is under the regulation of its amino acid sequence, which is encoded by a DNA. Therefore, if one successfully isolates a gene which encodes the polypeptide and determines the nucleotide sequence, it will be relatively easy to obtain the desired amount of the polypeptide by the steps of constructing a recombinant DNA which contains the DNA encoding the polypeptide, introducing the recombinant DNA into host-cells such as microorganisms, animals or plants, and culturing the obtained transformants in appropriate nutrient media. Under these, required are the isolation of a gene encoding the polypeptide as the entity of the enzyme described above, and the sequencing of the nucleotide sequence.

DISCLOSURE OF INVENTION

The first object of the present invention is to establish a polypeptide which has an α-isomaltosylglucosaccharide-forming enzyme activity of catalyzing the formation of a saccharide with a glucose polymerization degree of 3 or higher and bearing both the α-1,6 glucosidic linkage as a linkage at the non-reducing end and the α-1,4 glucosidic linkage other than the linkage at the non-reducing end, from a saccharide with a glucose polymerization degree of 2 or higher and bearing the α-1,4 glucosidic linkage as a linkage at the non-reducing end by α-glucosyl transferring reaction without substantially increasing the reducing power.

The second object of the present invention is to provide a DNA encoding the above polypeptide.

The third object of the present invention is to provide a replicable recombinant DNA comprising the above DNA.

The fourth object of the present invention is to provide a transformant transformed by the recombinant DNA.

The fifth object of the present invention is to provide a process for producing the polypeptide having α-isomaltosylglucosaccharide-forming enzyme activity by using the transformant.

The sixth object of the present invention is to provide uses of the polypeptide described above.

The present invention solves the first object described above by providing a polypeptide having α-isomaltosylglucosaccharide-forming activity and the following physicochemical properties:

(1) Forming a saccharide with a glucose polymerization degree of 3 or higher and bearing both the α-1,6 glucosidic linkage as a linkage at the non-reducing end and the α-1,4 glucosidic linkage other than the linkage at the non-reducing end from a saccharide with a glucose polymerization degree of 2 or higher and bearing the α-1,4 glucosidic linkage as a linkage at the non-reducing end by α-glucosyl transferring reaction without substantially increasing the reducing power;

(2) Molecular Weight

About 74,000 to 160,000 daltons when determined on sodium dodecyl sulfate polyacrylamide gel electrophoresis (SDS-PAGE);

(3) Optimum Temperature

About 40° C. to 50° C. when incubated at pH 6.0 for 60 minutes;

About 45° C. to 55° C. when incubated at pH 6.0 for 60 minutes in the presence of 1 mM $Ca^{2+}$;

About 60° C. when incubated at pH 8.4 for 60 minutes; or

About 65° C. when incubated at pH 8.4 for 60 minutes in the presence of 1 mM $Ca^{2+}$;

(4) Optimum pH

About 6.0 to 8.4 when incubated at 35° C. for 60 minutes;

(5) Thermal Stability

About 45° C. or lower when incubated at pH 6.0 for 60 minutes;

About 60° C. or lower when incubated at pH 6.0 for 60 minutes in the presence of 1 mM $Ca^{2+}$;

About 55° C. or lower when incubated at pH 8.0 for 60 minutes; or

About 60° C. or lower when incubated at pH 6.0 for 60 minutes in the presence of 1 mM $Ca^{2+}$; and (6) pH Stability About 5.0 to 10.0 when incubated at 4° C. for 24 hours.

The present invention solves the second object described above by providing a DNA encoding the polypeptide.

The present invention solves the third object described above by providing a replicable recombinant DNA which comprise a DNA encoding the polypeptide and an autonomously replicable vector.

The present invention solves the fourth object described above by providing a transformant constructed by introducing the recombinant DNA into an appropriate host.

The present invention solves the fifth object described above by providing a process for preparing the polypeptide, which comprises the steps of culturing a transformant constructed by introducing a replicable recombinant DNA, which contains a DNA encoding the polypeptide and an autonomously replicable vector, into an appropriate host; and collecting the polypeptide from the resultant culture.

The present invention solves the sixth object described above by establishing various uses of the polypeptide.

BEST MODE FOR CARRYING OUT THE INVENTION

Figure 1:
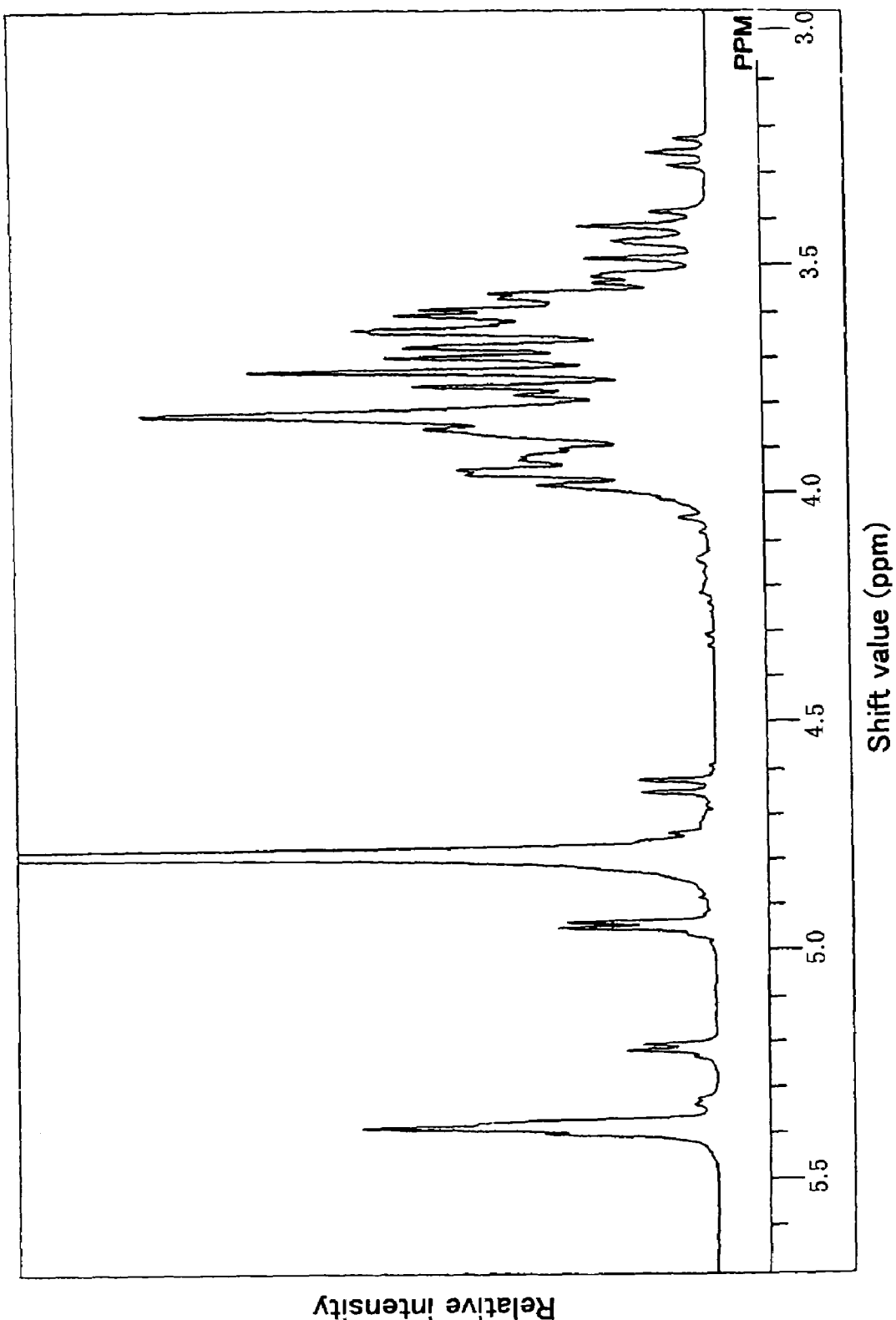
FIG. 1 shows a $^1$H-NMR spectrum of an enzymatic reaction product X which was obtained from maltotetraose using a polypeptide having α-isomaltosylglucosaccharide-forming enzyme activity.

The wording "polypeptide" as referred to as in the present invention means polypeptides in general which have an activity of forming a saccharide with a glucose polymerization degree of 3 or higher and bearing both the α-1,6 glucosidic linkage as a linkage at the non-reducing end and the α-1,4 glucosidic linkage other than the linkage at the non-reducing end from a saccharide with a glucose polymerization degree of 2 or higher and bearing α-1,4 glucosidic linkage as a linkage at the non-reducing end by α-glucosyl-transferring reaction without substantially increasing the reducing power.

The polypeptide of the present invention usually comprises a determined amino acid sequence, for example, an amino acid sequence of SEQ ID NO: 1 or mutants of SEQ ID NO: 1 having deletion, replacement with different amino acid(s), or addition of one or more of amino acids, i.e., at least one or two, for example, 1–50, 1–30, or 1–10 amino acids of SEQ ID NO: 1. Even-with the same DNA, the post-translational modification of a polypeptide by extra-/intra-cellular enzymes of host is affected by various conditions such as the kind of host, nutrients or composition of culture media, temperatures or pHs for the cultivation of a transformant having the above DNA. In such conditions, it is possible to arise some mutants having deletion or replacement with different amino acid of one or more, i.e., at least one or two, according to the situation, 1–30, 1–20, or 1–10 amino acids of the N-terminal region of SEQ ID NO: 1, further, or having addition of one or more, i.e., at least one or two, for example, 1–30, 1–20, or 1–10 amino acids to those N-termini. The -polypeptide of the present invention includes these mutants as far as their physicochemical properties have been revealed.

The polypeptide of the present invention can be obtained by the steps of introducing the DNA of the present invention into appropriate hosts, and collecting the polypeptide from the culture of the resultant transformants. The transformants usable in the present invention are those which contain a DNA comprising, for example, a nucleotide sequence, from the 5'-terminus, of SEQ ID NO: 4, SEQ ID NO: 5, or SEQ ID NO: 6; those having deletion, replacement or addition of one or more nucleotides in the above nucleotide sequence, those having anti-sense nucleotide sequences, or those having replacement of one or more nucleotides based on the degeneracy of genetic code without altering the amino acid sequence encoded by the above nucleotide sequence. The nucleotide sequence having replacement of one or more, i.e., at least one or two, optionally, 1–150, 1–90, 1–60, or 1–30 nucleotides based on gene-degeneracy without altering the amino acid sequence encoded by the above nucleotide sequence can be used as the nucleotide sequence.

The DNAs of the present invention include those of natural origin or those which can be synthesized in an artificial manner can be used as far as the DNAs encode the polypeptide of the present invention can be obtained. Microorganisms of the genus *Bacillus*, for example, *Bacillus globisporus* C9, deposited on Apr. 25, 2000, in the International Depositary Authority National Institute of Bioscience and Human-Technology, Agency of Industrial Science and Technology, 1–3, Higashi 1 chome Tsukuba-shi, Ibaraki-ken, Japan (International Patent Organism Depositary National Institute of Advanced Industrial Science and Technology Tsukuba Central 6, 1-1, Higashi 1-Chome Tsukuba-shi, Ibaraki-ken, 305-8566, Japan) under the accession number of FERM BP-7143; *Bacillus globisporus* C11, deposited on Apr. 25, 2000, in the International Patent Organism Depositary National Institute of Advanced Industrial Science and Technology Tsukuba Central 6, 1-1, Higashi 1-Chome Tsukuba-shi, Ibaraki-ken, 305-8566, Japan under the accession number of FERM BP-7144; and *Bacillus globisporus* N75, deposited on May 16, 2001, in the International Patent Organism Depositary National Institute of Advanced Industrial Science and Technology Tsukuba Central 6, 1-1, Higashi 1-Chome Tsukuba-shi, Ibaraki-ken, 305-8566, Japan under the accession number of FERMBP-7591; and other microorganisms belonging the genus *Arthrobacter* including *Arthrobacter globiformis* A19, deposited on May 16, 2001, in the International Patent Organism Depositary National Institute of Advanced Industrial Science and Technology Tsukuba Central 6, 1-1, Higashi 1-Chome Tsukuba-shi, Ibaraki-ken, 305-8566, Japan under the accession number of FERM BP-7590, are usable as the natural sources. A gene containing the DNA of the present invention can be obtained from the cells of the above microorganisms. Specifically, a gene containing the DNA can be released extracellularly by the steps of inoculating the microorganisms into a nutrient medium, culturing them about for one to three days under aerobic conditions, collecting the proliferated cells from the culture, and treating the cells with cell-lysis enzymes such as lysozyme and β-glucanase or with ultrasonication. In addition to the above methods, protein-hydrolyzing enzymes such as proteinases and freeze-thawing method in the presence of detergents such as sodium dodecyl sulfate can be used. The objective DNAs can be obtained from the disrupted cells using conventional methods in the art, for example, phenol-extraction, alcohol-precipitation, centrifugation, and ribonuclease-treatment. To synthesize the DNAs of the present invention artificially, chemical synthesis of the DNAs using the nucleotide sequence of SEQ ID NO: 4, SEQ ID NO: 5 or SEQ ID NO: 6 can be used. Also, PCR-method can be advantageously used to obtain the DNAs using a gene containing them as a template and appropriate chemically synthetic DNA as a primer.

The use of such DNAs enables the industrial production of the polypeptide of the present invention in a large amount and at a relatively low-cost: Such a production usually comprises the steps of inserting a specific DNA into an appropriate autonomously replicable vector to construct a recombinant DNA, introducing the resultant recombinant DNA into an appropriate host, culturing the resultant transformant in an appropriate nutrient medium for proliferation, collecting the cells from the culture, collecting the recombinant DNA from the cells, introducing the recombinant DNA into an appropriate host which can be easily proliferated for transformation, and culturing the resultant transformant in an appropriate nutrient medium. If one can obtain a DNA encoding the polypeptide of the present invention, the recombinant DNA described above can be relatively easily prepared by conventional recombinant DNA techniques. For example, plasmid vectors such as pBR322, pUC18, Bluescript II SK(+), pUB110, pTZ4, pC194, pHV14, TRp7, YEp7 and pBS7; or phage vectors such as λgt·λC, λgt·λB, ρ11, φ1 and φ105 can be used as the vectors. To express the DNA of the present invention in *E. coli*, pBR322, pUC18, Bluescript II SK(+), λgt·λC, and λgt·λB are preferable. To express the DNA of the present invention in *Bacillus subtilis*, pUB110, pTZ4, pC194, ρ11, φ1 and φ105 are preferable. Plasmids, pHV14, TRp7, YEp7 and pBS7 are useful in the case of replicating the recombinant DNA of the present invention in two or more hosts.

In order to insert the DNAs of the present invention into these vectors, conventional methods used in the art can be used. Specifically, a specific DNA is inserted into a vector by the steps of cleaving a gene containing the DNA and an autonomously replicable vector by restriction enzymes and/or ultrasonication and ligating the resulting DNA fragment and the resulting vector fragment. The ligation of the DNA fragment and the vector fragment can be easy by using restriction enzymes which specifically act on nucleotides, particularly, type II-restriction enzymes such as Sau 3AI, Eco RI, Hind III, Bam HI, Sal I, Xba I, Sac I and Pst I for cleaving gene and vector. After the annealing of the both, if necessary, the desired recombinant DNA can be obtained by ligating them in vivo or in vitro using a DNA ligase. The recombinant DNA thus obtained is unlimitedly replicable by the steps of introducing into appropriate hosts such as *Escherihia coli, Bacillus subtilis, Actinomyces*, and yeasts to construct transformants, and culturing the resultant transformants. On the cloning described above, the desired clones can be obtained from the transformants by applying the colony-hybridization method or screening by the steps of culturing in a nutrient medium containing saccharides with a glucose polymerization degree of 2 or higher and bearing the α-1,4 glucosidic linkage residue as a linkage at the non-reducing end and selecting a trabsformant which produces cyclotetrasaccharide from the saccharides.

The transformant, obtained by the cloning, produces the polypeptide extra- or intra-cellularly when cultured in a nutrient medium. Usually, conventional liquid media supplemented with carbon sources, nitrogen sources and minerals, and optionally trace-nutrients such as amino acids and vitamins are usually used as the nutrient media. Examples of the carbon sources usable in the present invention are saccharides including starch, starch hydrolyzate, glucose, fructose, sucrose, and trehalose. Examples of the nitrogen sources usable in the present invention are nitrogen-containing inorganic- or organic-substances including ammonia, ammonium salts, urea, nitrate, peptone, yeast extract, defatted soybean, corn-steep liquor and meat extract. Cultures containing the polypeptide can be obtained by the steps of inoculating the transformants into the nutrient media, culturing for about one to six days under aerobic conditions such as aeration and agitation conditions while keeping the temperature and pH, usually, at 20–40° C. and pH 2–10. Although the culture can be used intact as a crude polypeptide preparation comprising the polypeptide of the present invention, the polypeptide is usually separated from cells or cell debris and purified before use; it can be purified from the culture by removing cells or cell debris from the culture and applying conventional procedures used in the art for purifying polypeptides, for example, appropriately combining of one or more procedures such as concentration, salting out, dialysis, precipitation, gel filtration chromatography, ion-exchange chromatography, hydrophobic chromatography, affinity chromatography, gel electrophoresis and isoelectrophoresis.

The polypeptide of the present invention has an activity of forming a saccharides with a glucose polymerization degree of 3 or higher and bearing both the α-1,6-glucosidic linkage at the non-reducing end and the α-1,4 glucosidic linkage other than the linkage at the non-reducing end from a saccharide with a glucose polymerization degree of 2 or higher and bearing the α-1,4 glucosidic linkage as a linkage at the non-reducing end by α-glucosyl transferring reaction without substantially increasing the reducing power, and has the following physicochemical properties:

(1) Action
Forming a saccharide with a glucose polymerization degree of 3 or higher and bearing both the α-1,6 glucosidic linkage as a linkage at the non-reducing end and the α-1,4 glucosidic linkage other than the linkage at the non-reducing end from a saccharide with a glucose polymerization degree of 2 or higher and bearing the α-1,4 glucosidic linkage as a linkage at the non-reducing end by α-glucosyl transferring reaction without substantially increasing the reducing power;

(2) Molecular Weight
About 74,000 to 160,000 daltons when determined on sodium dodecyl sulfate polyacrylamide gel electrophoresis (SDS-PAGE);

(3) Optimum Temperature
About 40° C. to 50° C. when incubated at pH 6.0 for 60 minutes;
About 45° C. to 55° C. when incubated at pH 6.0 for 60 minutes in the presence of 1 mM $Ca^{2+}$;
About 60° C. when incubated at pH 8.4 for 60 minutes; or
About 65° C. when incubated at pH 8.4 for 60 minutes in the presence of 1 mM $Ca^{2+}$;

(4) Optimum pH
About 6.0 to 8.4 when incubated at 35° C. for 60 minutes;

(5) Thermal Stability
About 45° C. or lower when incubated at pH 6.0 for 60 minutes;
About 60° C. or lower when incubated at pH 6.0 for 60 minutes in the presence of 1 mM $Ca^{2+}$;
About 55° C. or lower when incubated at pH 8.0 for 60 minutes; or
About 60° C. or lower when incubated at pH 6.0 for 60 minutes in the presence of 1 mM $Ca^{2+}$; and (6) pH Stability
About 5.0 to 10.0 when incubated at 4° C. for 24 hours.

Polysaccharides comprising the α-1,4 glucosidic linkages such as starch, amylopectin, amylose, and glycogen, and their partial hydrolyzates such as amylodextrins, maltodextrins and maltooligosaccharides, which can be obtained by partially hydrolyzing them with amylases or acids, can be used as a substrate for the polypeptide of the present invention. Saccharides obtained by treating these glucosaccharides having the α-1,4 glucosidic linkage with branching enzymes (EC 2.4.1.18) can be optionally used as the substrate. The partial hydrolyzates obtained by hydrolyzing with amylases such as α-amylase (EC 3.2.1.1), β-amylase (EC 3.2.1.2), maltotriose-forming amylase (EC 3.2.1.116), maltotetraose-forming amylase (EC 3.2.1.60), maltopentaose-forming amylase, and maltohexaose-forming amylase (EC 3.2.1.98), which are described in Handbook of *Amylases and Related Enzymes*, Pergamon Press, Tokyo, Japan (1988), can be used as the substrate. Further, in the case of preparing the partial hydrolyzate, starch-debranching enzymes such as pullulanase (EC 3.2.1.41) and isoamylase (EC 3.2.1.68) can be arbitrarily used. Starches as the substrates include terrestrial starches from grains such as corn, wheat, and rice; and subterranean starches such as potato, sweet-potato, and tapioca. Preferably, these starches are gelatinized and/or liquefied into a liquid form in use. The lower the degree of partial hydrolysis, the higher the yield of cyclotetrasaccharide becomes, and therefore the DE is set to a level of about 20 or lower, preferably, about 12 or lower, more preferably, about five or lower. The concentration of the substrates is not specifically restricted, and the enzymatic reaction in the present invention proceeds even when used at a low concentration as low as 0.1%(w/w) (throughout the specification, "%(w/w)" is abbreviated as "%" hereinafter, unless specified otherwise). However, one percent or higher concentrations of the substrates are preferably used for industrial production. The substrate solutions may be those in a suspension form which contain incompletely-dissolved insoluble substrates. The substrate concentration is preferably 40% or lower, and more preferably 20% or lower. The reaction temperatures used in the present invention are those which proceed the enzymatic reaction, i.e., those up to 65° C., preferably, 30 to 50° C. The pHs for the enzymatic reaction are usually set to 4.5–8, preferably, about 5.5 to about 7. The time for the enzymatic reaction can be appropriately selected depending on the enzymatic reaction efficiency.

By contacting α-isomaltosyl-transferring enzyme with α-isomaltosylglucosaccharide formed by acting the polypeptide of the present invention on its substrate, cyclotetrasaccharide, which is useful in the art, can be easily produced in a large amount. The α-isomaltosyl-transferring enzyme can be allowed to act on its substrate after the action and then the inactivation of the polypeptide of the present invention. However, the combinational use of the polypeptide of the present invention and α-isomaltosyl-transferring enzyme is preferable. Specifically, by using the polypeptide of the present invention together with α-isomaltosyl-transferring enzyme, cyclotetrasaccharide can be obtained in a yield of about 30%, d.s.b., or higher from starches or partial hydrolyzates thereof, and about 80%, d.s.b., or higher from glycogen. The formation mechanism of cyclotetrasaccharide by the above combinational use can be estimated as follows based on the reaction properties of the two enzymes:

(1) The polypeptide of the present invention acts on the α-1,4 glucosyl residue at the non-reducing end of a saccharide, which has a glucose polymerization degree of 2 or higher and has the α-1,4 glucosidic linkage as a linkage at the non-reducing end, such as starch, glycogen, and the partial hydrolyzates thereof, to release a glucose residue; and then intermolecularly transfers the released glucose residue to the hydroxyl group at C-6 position of the glucose residue at the non-reducing end of other saccharide and forms a saccharide having an α-isomaltosyl residue at the non-reducing end;

(2) The α-isomaltosyl-transferring enzyme acts on the saccharide having an α-isomaltosyl residue at the non-reducing end, and then intermolecularly transfers the residue to the hydroxyl group at C-3 position of a glucose residue of other saccharide having an α-isomaltosyl residue at the non-reducing end and forms a saccharide having an α-isomaltosyl-1,3-isomaltosyl residue at the non-reducing end;

(3) The α-isomaltosyl-transferring enzyme acts on a saccharide having an α-isomaltosyl-1,3-isomaltosyl residue at the non-reducing end to release the α-isomaltosyl-1,3-isomaltosyl residue from the saccharide, and intramolecularly cyclizes the residue into cyclotetrasaccharide; and (4) Through the steps (1) to (3), cyclotetrasaccharide is formed from a remaining saccharide which is formed by releasing the α-isomaltosyl-1,3-isomaltosyl residue in the step (3), and the yield of cyclotetrasaccharide is highly increased by sequencially repeating the steps (1) to (3).

As explained above, it can be estimated that, when used in combination, the polypeptide of the present invention and α-isomaltosyl-transferring enzyme act on their substrates repeatedly to increase the yield of cyclotetrasaccharide.

During the cyclotetrasaccharide-forming reaction, optionally, other sacchride-transferring enzyme(s) can be advantageously used in combination to improve the yield of cyclotetrasaccharide; when two types of enzymes, i.e., the polypeptide of the present invention and α-isomaltosyl-transferring enzyme are allowed to act, for example, on an about 15% solution of partial starch hydrolyzate, cyclotetrasaccharide is produced in a yield of about 55%, while the use of three types of enzymes, i.e., the polypeptide of the present invention, α-isomaltosyl-transferring enzyme, and cyclomaltodextrin glucanotransferase, under the same condition described above, increases the maximum yield of cyclotetrasaccharide by about 5–10% to an improved yield of about 60–65%.

The saccharide solutions obtained by the above reaction can be used intact as solutions comprising cyclotetrasaccharide or saccharide compositions of the same. In general, however, they can be purified before use by appropriate purification procedures. Conventional procedures can be appropriately selected as the purification procedures. For example, one or more of the following purification procedures can be used alone or in combination: Decoloration or purification with activated charcoal, desalting by ion-exchange resins in a H- or OH-form, chromatographies such as thin-layer chromatography, high-performance liquid chromatography, ion-exchange column chromatography, activated charcoal column chromatography, and silica gel column chromatography, separation using organic solvents such as alcohols and acetone, membrane separation using adequate separability, hydrolysis of remaining saccharides using amylases including α-amylase, β-amylase, glucoamylase (EC 3.2.1.3), and α-glucosidase (EC 3.2.1.20), and hydrolysis and removal of the remaining saccharides by fermentation with yeast or by alkaline treatment. Particularly, ion-exchange column chromatography is preferably used as an industrial scale production method; column chromatography using strong-acid cation exchange resin as disclosed, for example, in Japanese Patent Kokai Nos. 23,799/83 and 72,598/83. Using the column chromatography, the contaminating saccharides can be removed to advantageously produce cyclotetrasaccharide with an improved content of the objective saccharide or saccharide compositions comprising the same. In this case, any one of fixed-bed, moving bed, and semi-moving bed methods can be appropriately used.

The resulting cyclotetrasaccharide or saccharide compositions comprising the same can be concentrated into syrup products, and optionally they can be further dried into amorphous powdery products.

To produce cyclotetrasaccharide crystals, for example, high cyclotetrasaccharide content solutions, having a concentration of about 30–90% and a purity of about 50% or higher of cyclotetrasaccharide, are placed into a crystallizer optionally in the presence of an organic solvent, and then gradually cooled while stirring in the presence of 0.1–20%, d.s.b., of a seed crystal to the cyclotetrasaccharide at a temperature of 95° C. or lower, preferably, 10–90° C., to obtain massecuites. The methods to produce cyclotetrasaccharide crystals and saccharide comprising the same from the massecuites include, for example, conventional methods such as block pulverization, fluidized granulation, and spray drying methods. Separation can be optionally selected as the method to produce cyclotetrasaccharide crystals with molasses.

The resulting cyclotetrasaccharide is a stable, high-quality, low sweetness, non-reducing white powder or syrup, and is almost free of browning, smelling, and deterioration of materials even when mixed or processed therewith: The materials are particularly, for example, amino acid-containing substances such as amino acids, oligopeptides, and proteins. Since cyclotetrasaccharide has a clathrating ability, it effectively inhibits the dispersion and quality deterioration of flavorful components and effective ingredients, and stably retains them. For such a purpose, if necessary, the combinational use of cyclotetrasaccharide and other cyclic saccharide(s) such as cyclodextrins, branched-cyclodextrins, cyclodexrans, and cyclofructans can be advantageously used to improve the level of the clathrating ability of cyclotetrasaccharide. The above cyclic saccharides such as cyclodextrins should not be restricted to those with a high purity, and cyclic saccharides with a relatively-low purity such as partial starch hydrolyzates containing a large amount of maltodextrins and various cyclodextrins can be advantageously used.

Since cyclotetrasaccharide, which is obtainable by using the polypeptide of the present invention, is not substantially hydrolyzed by amylases and α-glucosidases, it is free of assimilation by the body when orally administrated. Also, the saccharide is not substantially assimilated by intestinal bacteria, and therefore it can be used as an extremely-low caloric water-soluble dietary fiber. Cyclotetrasaccharide can be also used as a sweetener substantially free from causing dental caries because it is scarcely assimilated by dental caries-inducing bacteria. The saccharide prevents the adhesion and solidification. Cyclotetrasaccharide per se is a nontoxic, harmless, safe and stable natural sweetener. In the case of crystalline cyclotetrasaccharide, it can be advantageously used for tablets and sugar-coated tablets in combination with binders such as pullulan, hydroxyethyl-starch, and polyvinylpyrrolidone. Furthermore, cyclotetrasaccharide has useful properties of osmosis-controlling ability, filler-imparting ability, gloss-imparting ability, moisture-retaining ability, viscosity, crystallization-preventing ability for other saccharides, insubstantial fermentability, etc.

Thus, cyclotetrasaccharide and the saccharide compositions comprising the same of the present invention can be arbitrarily used as a sweetener, taste-improving agent, quality-improving agent, stabilizer, preventive of discoloration, filler, etc., in a variety of compositions such as food products, tobaccos, cigarettes, feeds, pet foods, cosmetics, and pharmaceuticals.

Cyclotetrasaccharide and the saccharide compositions comprising the same of the present invention can be used intact as sweeteners. If necessary, they can be advantageously used in combination with other sweeteners, for example, powdery syrup, glucose, fructose, lactose, isomerized sugar, sucrose, maltose, trehalose (α,α-trehalose, α,β-trehalose, and β,β-trehalose), honey, maple sugar, sorbitol, maltitol, dihydrochalcone, stevioside, α-glycosyl stevioside, sweetener of *Momordica grosvenori*, glycyrrhizin, thaumatin, L-aspartyl L-phenylalanine methyl ester, saccharine, acesulfame K, sucralose, glycine and alanine; and fillers such as dextrin, starch, and lactose. Particularly, cyclotetrasaccharide and the saccharide compositions comprising the same can be suitably used as a low caloric sweetener, dietary sweetener, or the like in combination with one or more low-caloric sweeteners such as erythritol, xylitol, and maltitol; and/or one or more sweeteners with a relatively-high sweetening power such as α-glycosyl stevioside, thaumatin, L-aspartyl L-phenylalanine methyl ester, saccharine, acesulfame K, and sucralose.

Cyclotetrasaccharide and the saccharide compositions comprising the same of the present invention can be arbitrarily used intact or, if necessary, after mixing with fillers, excipients, binders, etc., and them formed into products with different shapes such as granules, spheres, sticks, plates, cubes, and tablets.

Cyclotetrasaccharide and the saccharide compositions comprising the same of the present invention well harmonize with other tastable materials having sour-, salty-, bitter-, astringent-, delicious-, and bitter-taste; and have a high acid- and heat-tolerance. Thus, they can be favorably used to sweeten and/or improve the taste, and quality of food products in general, for example, a soy sauce, powdered soy sauce, miso, "funmatsu-miso" (a powdered miso), "moromi" (a refined sake), "hishio" (a refined soy sauce), "furikake" (a seasoned fishmeal), mayonnaise, dressing, vinegar, "sanbai-zu" (a sauce of sugar, soy sauce and vinegar), "funmatsu-sushi-zu" (powdered vinegar for sushi), "chuka-no-moto" (an instant mix for Chinese dish), "tentsuyu" (a sauce for Japanese deep fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar. Also, cyclotetrasaccharide and the saccharide compositions comprising the same can be arbitrarily used to sweeten and improve the taste, flavor, and quality of "wagashi" (Japanese cakes) such as "senbei" (a rice cracker), "arare" (a rice cake cube), "okoshi" (a millet and rice cake), "gyuhi" (a starch paste), "mochi" (a rise paste) and the like, "manju" (a bun with a bean-jam), "uiro" (a sweet rice jelly), "an" (a bean-jam) and the like, "yokan" (a sweet jelly of beans), "mizu-yokan" (a soft azuki-bean jelly), "kingyoku" (a kind of yokan), jelly, pao de Castella, and "amedama" (a Japanese toffee); Western confectioneries such as a bun, biscuit, cracker, cookie, pie, pudding, butter cream, custardcream, cream puff, waffle, sponge cake, doughnut, chocolate, chewing gum, caramel, nougat, and candy; frozen desserts such as an ice cream and sherbet; syrups such as a "kajitsu-no-syrup-zuke" (a preserved fruit) and "korimitsu" (a sugar syrup for shaved ice); pastes such as a flour paste, peanut paste, and fruit paste; processed fruits and vegetables such as a jam, marmalade, "syrup-zuke" (fruit pickles), and "toka" (conserves); pickles and pickled products such as a "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); premix for pickles and pickled products such as a "takuan-zuke-no-moto" (a premix for pickled radish), and "hakusai-zuke-no-moto" (a premix for fresh white rape pickles); meat products such as a ham and sausage; products of fish meat such as a fish ham, fish sausage, "kamaboko" (a steamed fish paste), "chikuwa" (a kind of fish paste), and "tenpura" (a Japanease deep-fat fried fish paste); "chinmi" (relish) such as a "uni-no-shiokara" (salted guts of urchin), "ika-no-shiokara" (salted guts of squid), "su-konbu" (processed tangle), "saki-surume" (dried squid strips), "fugu-no-mirin-boshi" (a dried mirin-seasoned swellfish), seasoned fish flour such as of Pacific cod, sea bream, shrimp, etc.; "tsukudani" (foods boiled down in soy sauce) such as those of laver, ediblewildplants, dried squid, small fish, and shellfish; daily dishes such as a "nimame" (cooked beans), potato salad, and "konbu-maki" (a tangle roll); milk products; canned and bottled products such as those of meat, fish meat, fruit, and vegetable; alcoholic beverages such as a synthetic sake, fermented liquor, fruit liquor, and sake; soft drinks such as a coffee, cocoa, juice, carbonated beverage, sour milk beverage, and beverage containing a lactic acid bacterium; instant food products such as instant pudding mix, instant hot cake mix, instant juice, instant coffee, "sokuseki-shiruko" (an instant mix of azuki-bean soup with rice cake), and instant soup mix; and other foods and beverages such as solid foods for babies, foods for therapy, drinks, beverage containing amino acids, peptide foods, and frozen foods.

Cyclotetrasaccharide and the saccharide compositions comprising the same can be arbitrarily used to improve the taste preference of feeds and pet foods for animals and pets such as domestic animals, poultry, honey bees, silk worms, and fishes; and also they can be arbitrarily used as a sweetener and taste-improving agent, taste-curing agent, quality-improving agent, and stabilizer in other products in a paste or liquid form such as tobacco, cigarette, tooth paste, lipstick, rouge, lip cream, internal liquid medicine, tablet, troche, cod-liver oil in the form of drop, oral refrigerant, cachou, gargle, cosmetic and pharmaceutical. When used as a quality-improving agent or stabilizer, cyclotetrasaccharide and the saccharide compositions comprising the same can be arbitrarily used in biologically active substances susceptible to lose their effective ingredients and activities, as well as in health foods, cosmetics, and pharmaceuticals containing the biologically active substances. Example of such biologically active substances are liquid preparations containing cytokines such as α-, β-, and γ-interferons, tumor necrosis factor-α(TNF-α), tumor necrosis factor-β(TNF-β), macropharge migration inhibitory factor, colony-stimulating factor, transfer factor, and interleukin 2; liquid preparations containing hormones such as insulin, growth hormone, prolactin, erythropoietin, and follicle-stimulating hormone; biological preparations such as BCG vaccine, Japanese encephalitis vaccine, measles vaccine, live polio vaccine, small pox vaccine, tetanus toxoid, Trimeresurus antitoxin, and human immunoglobulin; antibiotics such as penicillin, erythromycin, chloramphenicol, tetracycline, streptomycin, and kanamycin sulfate; vitamins such as thiamin, ribofravin, L-ascorbic acid, cod liver oil, carotenoide, ergosterol, tocopherol; solution of enzymes such as lipase, esterase, urokinase, protease, β-amylase, isoamylase, glucanase, and lactase; extracts such as ginseng extract, turtle extract, chlorella extract, aloe extract, and propolis extract; and royal jelly. By using cyclotetrasaccharide and the saccharide compositions comprising the same, the above biologically active substances and other paste of living microorganisms such as virus, lactic acid bacteria, and yeast can be arbitrarily prepared into health foods and pharmaceuticals in a liquid, paste, or solid form, which have a satisfactorily-high stability and quality with less fear of losing or inactivating their effective ingredients and activities.

The methods for incorporating cyclotetrasaccharide or the saccharide composition comprising the same into the aforesaid compositions are those which can incorporate cyclotetrasaccharide and the saccharide compositions into a variety of compositions before completion of their processing, and which can be appropriately selected among the following conventional methods; mixing, kneading, dissolving, melting, soaking, penetrating, dispersing, applying, coating, spraying, injecting, crystallizing, and solidifying. The amount of the cyclotetrasaccharide or the saccharide compositions comprising the same to be preferably incorporated into the final compositions is usually in an amount of 0.1% or higher, desirably, 1% or higher.

The following experiments explain the physicochemical properties of the polypeptides having an α-isomaltosylglucosaccharide-forming enzyme activity from *Bacillus globisporus* C11, *Bacillus globisporus* N75, and *Arthrobacter globiformis* A19, DNAs encoding the polypeptide having an α-isomaltosylglucosaccharide-forming enzyme activity, and the preparation methods of recombinant polypeptides having an α-isomaltosylglucosaccharide-forming enzyme activity.

EXPERIMENT 1

Preparation of a Polypeptide having an α-Isomaltosylglucosaccharide-forming Enzyme Activity from *Bacillus globisporus* C11

Experiment 1-1

Preparation of α-Isomaltosylglucosaccharide-forming Enzyme

A liquid culture medium consisting 4% (w/v) of "PINE-DEX #4", a partial starch hydrolyzate, 1.8% (w/v) of "ASA-HIMEAST", a yeast extract, 0.1% (w/v) of dipotassium phosphate, 0.06% (w/v) of sodium phosphate dodeca-hydrate, 0.05% (w/v) of magnesium sulfate hepta-hydrate, and water was placed in 500-ml Erlenmeyer flasks in a respective amount of 100 ml, sterilized by autoclaving at 121° C. for 20 minutes, cooled and seeded with *Bacillus globisporus* C11 strain, followed by culturing under rotary-shaking conditions at 27° C. and 230 rpm for 48 hours for a seed culture. About 20 L of a fresh preparation of the same liquid culture medium as used in the above seed culture were placed in a 30 L fermentor, sterilized by heating, and then cooled to 27° C. and inoculated with 1% (v/v) of the seed culture, followed by culturing at 27° C. and pH. 6.0 to 8.0 for 48 hours under aeration-agitation conditions. After the completion of the culture, about 0.55 unit/ml of α-isomaltosylglucosaccharide-forming enzyme and about 1.8 units/ml of α-isomaltosyl-transferring enzyme were detected in the resulting culture by measuring enzyme activities. About 18 L of supernatant obtained by centrifugation (10,000 rpm, 30 minutes) had about 0.51 units/ml of α-isomaltosylglucosaccharide-forming enzyme activity, i.e., a total activity of about 9,180 units; and about 1.7 units/ml of α-isomaltosyl-transferring enzyme activity, i.e., a total enzymatic activity of about 30,400 units. Since both enzyme activities were detected mainly in culture supernatant, it was revealed that these enzymes were secretion enzymes secreted in the culture.

The two types of enzymatic activities described above were measured as following. The activity of α-isomaltosyl-glucosaccharide-forming enzyme was measured by the following assay: A substrate solution was prepared by dissolving maltotriose in 100 mM acetate buffer (pH 6.0) to give a concentration of 2% (w/v). A reaction mixture was prepared by mixing 0.5 ml of the substrate solution and 0.5 ml of an enzyme solution, and incubated at 35° C. for 60 minutes. After stopping the reaction by boiling for 10 minutes, the amount of maltose formed in the reaction mixture was determined by high-performance liquid chromatography (HPLC). One unit of α-isomaltosylglucosaccharide-forming activity was defined as the amount of the enzyme that forms one μmole of maltose per minute under the above conditions. HPLC was carried out using "SHODEX KS-801 column", Showa Denko K. K., Tokyo, Japan, at a column temperature of 60° C. and a flow rate of 0.5 ml/minutes of water, and using "RI-8012", a differential refractometer commercialized by Tosoh Corporation, Tokyo, Japan.

The activity of α-isomaltosyl-transferring enzyme was measured by the following assay: A substrate solution was prepared by dissolving panose in 100 mM acetate buffer (pH 6.0) to give a concentration of 2% (w/v). A reaction mixture was prepared by mixing 0.5 ml of the substrate solution and 0.5 ml of an enzyme solution, and incubated at 35° C. for 30 minutes. After stopping the reaction by boiling for 10 minutes, the amount of glucose formed in the reaction mixture was determined by the glucose oxidase-peroxidase method. One unit of α-isomaltosyl-transferring activity was defined as the amount of the enzyme that forms one μmole of glucose per minute under the above conditions.

Experiment 1-2

Preparation of Partially Purified Enzymes

About 18 L of the culture supernatant obtained in Experiment 1-1 were salted out with 80% saturated ammonium sulfate solution and allowed to stand at 4° C. for 24 hours, and the formed precipitates were collected by centrifugation (10,000 rpm, 30 minutes), dissolved in 10 mM sodium phosphate buffer (pH 7.5), and dialyzed against the same buffer to obtain about 416 ml of a crude enzyme solution. The crude enzyme solution had about 8,440 units of α-isomaltosylglucosaccharide-forming enzyme and about 28,000 units of α-isomaltosyl-transferring enzyme. The crude enzyme solution was subjected to ion-exchange column chromatography using "SEPABEADS FP-DA13" gel, an ion-exchange resin commercialized by Mitsubishi Chemical Industries, Ltd., Tokyo, Japan. Both α-isomaltosylglucosaccharide-forming enzyme and α-isomaltosyl-transferring enzyme were eluted as non-adsorbed fractions without adsorbing on "SEPABEADS FP-DA13" gel. The non-adsorbed fraction was collected and dialyzed against 10 mM sodium phosphate buffer (pH 7.0) with 1 M ammonium sulfate. The dialyzed solution was centrifuged to remove impurities, and subjected to affinity column chromatography using 500 ml of "SEPHACRYL HR S-200" gel, a gel commercialized by Amersham Biosciences K. K., Tokyo, Japan (old name, Amersham Pharmacia Biotech). Enzymatically active components adsorbed on "SEPHACRY HR S-200" gel and, when sequentially eluted with a linear gradient decreasing from 1 M to 0 M of ammonium sulfate and a linear gradient increasing from 0 mM to 100 mM of maltotetraose, the α-isomaltosyl-transferring enzyme and the α-isomaltosylglucosaccharide-forming enzyme were separately eluted, i.e., the former was eluted with a linear gradient of ammonium sulfate at about 0.3 M and the latter was eluted with a linear gradient of maltotetraose at about 30 mM. Thus, fractions with the α-isomaltosylglucosaccharide-forming enzyme activity and those with the α-isomaltosyl-transferring enzyme activity were separately collected as partially purified preparations of α-isomaltosylglucosaccharide-forming enzyme and α-isomaltosyl-transferring enzyme. Further, these enzyme preparations were purified separately.

Experiment 1-3

Purification of a Polypeptide having an α-Isomaltosylglucosaccharide-forming Enzyme Activity The partially purified enzyme preparation having α-isomaltosylglucosaccharide-forming enzyme activity, obtained in Experiment 1-2, was dialyzed against 10 mM sodium phosphate buffer (pH 7.0) with 1 M ammonium sulfate. The dialyzed solution was centrifuged to remove impurities, and subjected to hydrophobic column chromatography using 350 ml of "BUTYL-TOYOPEARL 650M" gel, a hydrophobic gel commercialized by Tosoh Corporation, Tokyo, Japan. The enzyme was adsorbed on "BUTYL-TOYOPEARL 650M" gel and, when eluted with a linear gradient decreasing from 1 M to 0M of ammonium sulfate, the enzymatic activity was eluted with a linear gradient of ammonium sulfate at about 0.3 M, and fractions with the enzyme activity was collected. The collected solution was dialyzed against 10 mM sodium phosphate buffer (pH 7.0) with 1 M ammonium sulfate, and the dialyzed solution was centrifuged to remove impurities, and purified by affinity chromatography using "SEPHACRYL HR S-200" gel. The amount of enzyme activity, specific activity and yield of the α-isomaltosylglucosaccharide-forming enzyme in each purification step are shown in Table 1.

TABLE 1

| Purification step | Enzyme* activity (unit) | Specific activity of enzyme* (unit/mg protein) | Yield (%) |
|---|---|---|---|
| Culture supernatant | 9,180 | 0.14 | 100 |
| Dialyzed solution after salting out with ammonium sulfate | 8,440 | 0.60 | 91.9 |
| Elute from ion-exchange column chromatography | 6,620 | 1.08 | 72.1 |
| Elute from affinity column chromatography | 4,130 | 8.83 | 45.0 |
| Elute from hydrophobic column chromatography | 3,310 | 11.0 | 36.1 |
| Elute from affinity column chromatography | 2,000 | 13.4 | 21.8 |

Note:
The symbol "*" means the α-isomaltosylglucosaccharide-forming enzyme of the present invention.

The finally purified α-isomaltosylglucosaccharide-forming enzyme polypeptide specimen was assayed for purity on gel electrophoresis using a 7.5% (w/v) polyacrylamide gel and detected on the gel as a single protein band, i.e., a high purity specimen.

Experiment 1-4

Purification of a Polypeptide having an α-Isomaltosyl-transferring Enzyme Activity The partially purified enzyme preparation having α-isomaltosyl-transferring enzyme activity, obtained in Experiment 1-2, was dialyzed against 10 mM sodium phosphate buffer (pH 7.0) with 1 M ammonium sulfate. The dialyzed solution was centrifuged to remove impurities, and subjected to hydrophobic column chromatography using 350 ml of "BUTYL-TOYOPEARL 650M" gel, a hydrophobic gel commercialized by Tosoh Corporation, Tokyo, Japan. The enzyme adsorbed on "BUTYL-TOYOPEARL 650M" gel and, when eluted with a linear gradient decreasing from 1 M to 0M of ammonium sulfate, the enzymatically active fractions were eluted with a linear gradient of ammonium sulfate at about 0.3 M, and fractions with the enzyme activity was collected. The collected solution was dialyzed against 10 mM sodium phosphate buffer (pH 7.0) with 1 M ammonium sulfate, and the dialyzed solution was centrifuged to remove impurities, and purified by affinity chromatography using "SEPHACRYL HR S-200" gel. The amount of enzyme activity, specific activity and yield of the α-isomaltosyl-transferring enzyme in each purification step are in Table 2.

| Purification step | Enzyme* activity (unit) | Specific activity of enzyme* (unit/mg protein) | Yield (%) |
|---|---|---|---|
| Culture supernatant | 30,400 | 0.45 | 100 |
| Dialyzed solution after salting out with ammonium sulfate | 28,000 | 1.98 | 92.1 |
| Elute from ion-exchange column chromatography | 21,800 | 3.56 | 71.7 |
| Elute from affinity column chromatography | 13,700 | 21.9 | 45.1 |
| Elute from hydrophobic column chromatography | 10,300 | 23.4 | 33.9 |
| Elute from affinity column chromatography | 5,510 | 29.6 | 18.1 |

Note:
The symbol "*" means the α-isomaltosyl-transferring enzyme.

The finally purified α-isomaltosyl-transferring enzyme specimen was assayed for purify on gel electrophoresis using a 7.5% (w/v) polyacrylamide gel and detected on the gel as a single protein band, i.e., a high purity polypeptide.

EXPERIMENT 2

Preparation of a Polypeptide having an α-Isomaltosylglucosaccharide-forming Enzyme Activity from *Bacillus globisporus* N75

Experiment 2-1

Preparation of α-Isomaltosylglucosaccharide-forming Enzyme

A liquid culture medium consisting 4% (w/v) of "PINE-DEX #4", a partial starch hydrolyzate, 1.8% (w/v) of "ASA-HIMEAST", a yeast extract, 0.1% (w/v) of dipotassium phosphate, 0.06% (w/v) of sodium phosphate dodeca-hydrate, 0.05% (w/v) of magnesium sulfate hepta-hydrate, and water was placed in 500-ml Erlenmeyer flasks in a respective amount of 100 ml, sterilized by autoclaving at 121° C. for 20 minutes, cooled and seeded with *Bacillus globisporus* N75, followed by culturing under rotary-shaking conditions at 27° C. and 230 rpm for 48 hours for a seed culture. About 20 L of a fresh preparation of the same liquid culture medium as used in the above seed culture were placed in a 30 L fermentor, sterilized by heating, and then cooled to 27° C. and inoculated with 1% (v/v) of the seed culture, followed by culturing at 27° C. and pH 6.0 to 8.0 for 48 hours under aeration-agitation conditions. After the completion of the culture, about 0.34 unit/ml of α-isomaltosylglucosaccharide-forming enzyme and about 1.1 units/ml of α-isomaltosyl-transferring enzyme were detected in the resulting culture by measuring enzyme activities. About 18 L of supernatant obtained by centrifugation (10,000 rpm, 30 minutes) had about 0.33 units/ml of α-isomaltosylglucosaccharide-forming enzyme activity, i.e., a total activity of about 5,940 units; and about 1.1 units/ml of α-isomaltosyl-transferring enzyme activity, i.e., a total enzymatic activity of about 19,800 units. Since both enzyme activities were detected mainly in culture supernatant, it was revealed that these enzymes were secretion enzymes secreted in the culture.

Experiment 2-2

Preparation of Partially Purified Enzymes

About 18 L of the culture supernatant obtained in Experiment 2-1 was salted out with 80% saturated ammonium sulfate solution and allowed to stand at 4° C. for 24 hours, and the formed precipitates were collected by centrifugation (10,000 rpm, 30 minutes), dissolved in 10 mM Tris-HCl buffer (pH 8.3), and dialyzed against the same buffer to obtain about 450 ml of crude enzyme solution. The crude enzyme solution had about 4,710 units of α-isomaltosylglucosaccharide-forming enzyme activity and about 15,700 units of α-isomaltosyl-transferring enzyme activity. The crude enzyme solution was subjected to ion-exchange column chromatography using "SEPABEADS FP-DA13" gel, disclosed in Experiment 1-1. α-Isomaltosylglucosaccharide-forming enzyme was adsorbed on "SEPABEADS FP-DA13" gel, and α-isomaltosyl-transferring enzyme was eluted as non-adsorbed fraction without adsorbing on "SEPABEADS FP-DA13" gel. Subsequently, α-isomaltosylglucosaccharide-forming enzyme was eluted with a linear gradient of increasing from 0 M to 1 M of sodium chloride, where the enzyme was eluted with the linear gradient of sodium chloride at a concentration of about 0.25 M. Therefore, fractions with α-isomaltosylglucosaccharide-forming enzyme and with α-isomaltosyl-transferring enzyme were separately collected as partially purified enzyme preparation having α-isomaltosylglucosaccharide-forming enzyme activity and that having α-isomaltosyl-transferring enzyme activity, respectively. Further, these enzyme preparations were separately purified.

Experiment 2-3

Purification of a Polypeptide having α-Isomaltosylglucosaccharide-forming Enzyme Activity The partially purified enzyme preparation having α-isomaltosylglucosaccharide-forming enzyme activity, obtained in Experiment 2-2, was dialyzed against 10 mM sodium phosphate buffer (pH 7.0) with 1 M ammonium sulfate. The dialyzed solution was centrifuged to remove impurities, and subjected to affinity column chromatography using 500 ml of "SEPHACRYL HR S-200" gel, a gel commercialized by Amersham Biosciences K. K., Tokyo, Japan (old name, Amersham Pharmacia Biotech). The enzyme was adsorbed on "SEPHACRYL HR S-200" gel and, when sequentially eluted with a linear gradient decreasing from 1 M to 0 M of ammonium sulfate and a linear gradient increasing from 0 mN to 100 mM of maltotetraose, the enzymatic activity was eluted with a linear gradient of maltotetraose at about 30 mM, and fractions with the enzyme activity was collected. The collected solution was dialyzed against 10 mM sodium phosphate buffer (pH 7.0) with 1 M ammonium sulfate, and the dialyzed solution was centrifuged to remove impurities, and purified by hydrophobic column chromatography using 350 ml of "BUTYL-TOYOPEARL 650M" gel, a hydrophobic gel commercialized by Tosoh Corporation, Tokyo, Japan. The enzyme was adsorbed on "BUTYL-TOYOPEARL 650M" gel and, when eluted with a linear gradient decreasing from 1 M to 0 M of ammonium sulfate, the enzymatic activity was eluted with a linear gradient of ammonium sulfate at about 0.3 M, and fractions with the enzyme activity was collected. The collected solution was dialyzed against 10 mM sodium phosphate buffer (pH 7.0) with 1 M ammonium sulfate, and the dialyzed solution was centrifuged to remove impurities, and purified by affinity chromatography using "SEPHACRLY HR S-200" gel. The amount of enzyme activity, specific activity and yield of the α-isomaltosylglucosaccharide-forming enzyme in each purification step are shown in Table 3.

| Purification step | Enzyme* activity (unit) | Specific activity of enzyme* (unit/mg protein) | Yield (%) |
|---|---|---|---|
| Culture supernatant | 5,940 | 0.10 | 100 |
| Dialyzed solution after salting out with ammonium sulfate | 4,710 | 0.19 | 79.3 |
| Elute from ion-exchange column chromatography | 3,200 | 2.12 | 53.9 |
| Elute from affinity column chromatography | 2,210 | 7.55 | 37.2 |
| Elute from hydrophobic column chromatography | 1,720 | 10.1 | 29.0 |
| Elute from affinity column chromatography | 1,320 | 12.5 | 22.2 |

Note:
The symbol "*" means the α-isomaltosylglucosaccharide-forming enzyme of the present invention.

The finally purified α-isomaltosylglucosaccharide-forming enzyme specimen was assayed for purify on gel electrophoresis using a 7.5% (w/v) polyacrylamide gel and detected on the gel as a single protein band, i.e., a high purity polypeptide.

Experiment 2-4

Purification of a Polypeptide having an α-Isomaltosyl-transferring Enzyme Activity The partially purified enzyme preparation having α-isomaltosyl-transferring activity, obtained in Experiment 2-2, was dialyzed against 10 mM sodium phosphate buffer (pH 7.0) with 1 M ammonium sulfate. The dialyzed solution was centrifuged to remove impurities, and subjected to affinity column chromatography using 500 ml of "SEPHACRYL HR S-200" gel, a gel commercialized by Amersham Biosciences K. K., Tokyo, Japan (old name, Amersham Pharmacia Biotech). The enzyme was adsorbed on "SEPHACRYL HR S-200" gel and, when eluted with a linear gradient decreasing from 1 M to 0M of ammonium sulfate, the enzymatic activity was eluted with a linear gradient of ammonium sulfate at about 0.3 M, and fractions with the enzyme activity was collected. The collected solution was dialyzed against 10 mM sodium phosphate buffer (pH 7.0) with 1 M ammonium sulfate, and the dialyzed solution was centrifuged to remove impurities, and purified by hydrophobic column chromatography using "BUTYL-TOYOPEARL 650M" gel, a hydrophobic gel commercialized by Tosoh Corporation, Tokyo, Japan. The polypeptide was adsorbed on "BUTYL-TOYOPEARL 650M" gel and, when eluted with a linear gradient decreasing from 1 M to 0M of ammonium sulfate, the enzymatic activity was eluted with a linear gradient of ammonium sulfate at about 0.3 M, and fractions with the enzyme activity was collected. The collected solution was dialyzed against 10 mM Tris-HCl buffer (pH 8.0), and the dialyzed solution was centrifuged to remove impurities, and purified by ion-exchange column chromatography using 380 ml of "SUPER Q-TOYOPEARL 650C" gel, an ion-exchange gel commercialized by Tosoh Corporation, Tokyo, Japan. The enzyme was eluted as non-adsorbed fraction without adsorbing on "SUPER Q-TOYOPEARL 650C" gel. The purified polypeptide specimen having α-isomaltosyl-transferring enzyme activity was obtained by collecting the fractions. The amount of enzyme activity, specific activity and yield of the α-isomaltosyl-transferring enzyme in each purification step are shown in Table 4.

TABLE 4

| Purification step | Enzyme* activity (unit) | Specific activity of enzyme* (unit/mg protein) | Yield (%) |
|---|---|---|---|
| Culture supernatant | 19,000 | 0.33 | 100 |
| Dialyzed solution after salting out with ammonium sulfate | 15,700 | 0.64 | 82.6 |
| Elute from ion-exchange column chromatography | 12,400 | 3.56 | 65.3 |
| Elute from affinity column chromatography | 8,320 | 11.7 | 43.8 |
| Elute from hydrophobic column chromatography | 4,830 | 15.2 | 25.4 |
| Elute from ion-exchange column chromatography | 3,850 | 22.6 | 20.3 |

Note:
The symbol "*" means the α-isomaltosyl-transferring enzyme.

The finally purified α-isomaltosyl-transferring enzyme specimen was assayed for purify on gel electrophoresis using a 7.5% (w/v) polyacrylamide gel and detected on the gel as a single protein band, i.e., a high purity polypeptide.

EXPERIMENT 3

Preparation of a Polypeptide having an α-Isomaltosylglucosaccharide-forming Enzyme Activity from *Arthrobacter globiformis* A19

Experiment 3-1

Preparation of α-Isomaltosylglucosaccharide-forming Enzyme

A liquid culture medium consisting 4% (w/v) of "PINE-DEX #4", a partial starch hydrolyzate, 1.8% (w/v) of "ASA-HIMEAST", a yeast extract, 0.1% (w/v) of dipotassium phosphate, 0.06% (w/v) of sodium phosphate dodeca-hydrate, 0.05% (w/v) of magnesium sulfate hepta-hydrate, and water was placed in 500-ml Erlenmeyer flasks in a respective amount of 100 ml, sterilized by autoclaving at 121° C. for 20 minutes, cooled and seeded with *Arthrobacter globiformis* A19, followed by culturing under rotary-shaking conditions at 27° C. and 230 rpm for 48 hours for a seed culture. About 20 L of a fresh preparation of the same liquid culture medium as used in the above seed culture were placed in a 30 L fermentor, sterilized by heating, and then cooled to 27° C. and inoculated with 1% (v/v) of the seed culture, followed by culturing at 27° C. and pH 6.0 to 9.0 for 48 hours under aeration-agitation conditions. After the completion of the culture, about 1.1 unit/ml of α-isomaltosylglucosaccharide-forming enzyme and about 1.7 units/ml of α-isomaltosyl-transferring enzyme were detected in the resulting culture by measuring enzyme activities. About 18 L of supernatant obtained by centrifugation (10,000 rpm, 30 minutes) had about 1.06 units/ml of α-isomaltosylglucosaccharide-forming enzyme activity, i.e., a total activity of about 19,100 units; and about 1.6 units/ml of α-isomaltosyl-transferring enzyme activity, i.e., a total enzymatic activity of about 28,800 units. Since both enzyme activities were detected mainly in culture supernatant, it was revealed that these enzymes were secretion enzymes secreted in the culture. Except for using 100 mM Glycine-NaOH buffer (pH 8.4) as the buffer to dissolve the substrate, the activity of α-isomaltosylglucosaccharide-forming enzyme from *Arthrobacter globiformis* A19 was measured according to the method described in Experiment 1

Experiment 3-2

Preparation of Partially Purified Enzymes

About 18 L of the culture supernatant obtained in Experiment 3-1 was salted out with 60% saturated ammonium sulfate solution and allowed to stand at 4° C. for 24 hours, and the formed precipitates were collected by centrifugation (10,000 rpm, 30 minutes), dissolved in 10 mM Tris-HCl buffer (pH 7.0), and dialyzed against the same buffer to obtain about 850 ml of crude enzyme solution. The crude enzyme solution had about 8,210 units of α-isomaltosylglucosaccharide-forming enzyme activity and about 15,700 units of α-isomaltosyl-transferring enzyme activity. The crude enzyme solution was subjected to ion-exchange column chromatography using 380 ml of "DEAE-TOYOPEARL 650S" gel, an ion-exchange gel commercialized by Tosoh Corporation, Tokyo, Japan. Both enzymes were adsorbed on "DEAE-TOYOPEARL 650S" gel and eluted with a linear gradient of increasing from 0 M to 1 M of sodium chloride, where α-isomaltosylglucosaccharide-forming enzyme and α-isomaltosyl-transferring enzyme were eluted with the linear gradient of sodium chloride at concentrations of about 0.2 M and about 0.3 M, respectively. Therefore, fractions with α-isomaltosylglucosaccharide-forming enzyme and with α-isomaltosyl-transferring enzyme were separately collected as partially purified enzyme preparation having α-isomaltosylglucosaccharide-forming enzyme activity and that having α-isomaltosyl-transferring enzyme activity, respectively. Further, these enzyme preparations were separately purified.

Experiment 3-3

Purification of a Polypeptide having α-Isomaltosylglucosaccharide-forming Enzyme Activity The partially purified enzyme preparation having α-isomaltosylglucosaccharide-forming enzyme activity, obtained in Experiment 3-2, was dialyzed against 10 mM sodium phosphate buffer (pH 7.0) with 1 M ammonium sulfate. The dialyzed solution was centrifuged to remove impurities, and subjected to affinity column chromatography using 500 ml of "SEPHACRYL HR S-200" gel, a gel commercialized by Amersham Biosciences K. K., Tokyo, Japan (old name, Amersham Pharmacia Biotech). The enzyme was adsorbed on "SEPHACRYL HR S-200" gel and, when eluted with a linear gradient decreasing from 1 M to 0 M of ammonium sulfate, the enzymatic activity was eluted with a linear gradient of ammonium sulfate at about 0.2 M, and fractions with the enzyme activity was collected as purified enzyme preparation. The amount of enzyme activity, specific activity and yield of the α-isomaltosylglucosaccharide-forming enzyme in each purification step are shown in Table 5.

TABLE 5

| Purification step | Enzyme* activity (unit) | Specific activity of enzyme* (unit/mg protein) | Yield (%) |
|---|---|---|---|
| Culture supernatant | 19,100 | 0.11 | 100 |
| Dialyzed solution after salting out with ammonium sulfate | 8,210 | 0.48 | 43.0 |
| Elute from ion-exchange column chromatography | 6,890 | 4.18 | 36.1 |
| Elute from affinity column chromatography | 5,220 | 35.1 | 27.3 |

Note:
The symbol "*" means the α-isomaltosylglucosaccharide-forming enzyme of the present invention.

The finally purified α-isomaltosylglucosaccharide-forming enzyme specimen was assayed for purity on gel electrophoresis using a 7.5% (w/v) polyacrylamide gel and detected on the gel as a single protein band, i.e., a high purity polypeptide.

Experiment 3-4

Partial Purification of a Polypeptide having an α-Isomaltosyl-transferring Enzyme Activity The partially purified enzyme preparation having α-isomaltosyl-transferring activity, obtained in Experiment 3-2, was dialyzed against 10 mM sodium phosphate buffer (pH 7.0) with 1 M ammonium sulfate. The dialyzed solution was centrifuged to remove impurities, and subjected to affinity column chromatography using 500 ml of "SEPHACRYL HR S-200" gel, a gel commercialized by Amersham Biosciences K. K., Tokyo, Japan (old name, Amersham Pharmacia Biotech). The enzyme was adsorbed on "SEPHACRYL HR S-200" gel and, when eluted with a linear gradient decreasing from 1 M to 0 M of ammonium sulfate, the enzymatic activity was eluted with a linear gradient of ammonium sulfate at about 0 M, and fractions with the enzyme activity was collected as partially purified enzyme preparation. The amount of enzyme activity, specific activity and yield of the α-isomaltosyl-transferring enzyme in each purification step are shown in Table 6.

TABLE 6

| Purification step | Enzyme* activity (unit) | Specific activity of enzyme* (unit/mg protein) | Yield (%) |
|---|---|---|---|
| Culture supernatant | 28,800 | 0.18 | 100 |
| Dialyzed solution after salting out with ammonium sulfate | 15,700 | 0.97 | 54.5 |

TABLE 6-continued

| Purification step | Enzyme* activity (unit) | Specific activity of enzyme* (unit/mg protein) | Yield (%) |
|---|---|---|---|
| Elute from ion-exchange column chromatography | 7,130 | 4.01 | 24.8 |
| Elute from affinity column chromatography | 1,800 | 11.9 | 6.3 |

Note:
The symbol "*" means the α-isomaltosyl-transferring enzyme.

The partially purified α-isomaltosyl-transferring enzyme specimen was assayed for purity on gel electrophoresis using a 7.5% (w/v) polyacrylamide gel and detected on the gel as one main and three minor protein bands.

Experiment 4-1

Action on Saccharides

It was tested whether saccharides can be used as substrates for the polypeptide of α-isomaltosylglucosaccharide-forming enzyme of the present invention. For the purpose, a solution of maltose, maltotriose, maltotetraose, maltopentaose, maltohexaose, maltoheptaose, isomaltose, isomaltotriose, panose, isopanose, trehalose, kojibiose, nigerose, neotrehalose, cellobiose, gentibiose, maltitol, maltotriitol, lactose, sucrose, erlose, selaginose, maltosyl glucoside, or isomaltosyl glucoside was prepared.

To each of the above solutions was added two units/g substrate of a purified polypeptide specimen of α-isomaltosylglucosaccharide-forming enzyme from either *Bacillus globisporus* C11 obtained by the method in Experiment 1-3, *Bacillus globisporus* N75 obtained by the method in Experiment 2-3, or *Arthrobacter globiformis* A19 obtained by the method in Experiment 3-3, and the resulting each solution was adjusted to give a substrate concentration of 2% (w/v) and incubated at 30° C. and pH 6.0, except for using pH 8.4 for the enzyme from *Arthrobacter globiformis* A19, for 24 hours. In order to analyze the saccharides in the reaction mixture before and after the enzymatic reaction, silica gel thin-layer chromatography (hereinafter, abbreviated as "TLC") was carried out. After two-times development using, as a developer, a mixture solution of n-butanol, pyridine, and water (=6:4:1), and, as a thin-layer plate, "KIESELGEL 60", an aluminum plate (20×20 cm) for TLC commercialized by Merck & Co., Inc., Rahway, USA, the saccharides in the reaction mixture were examined whether the enzyme acted or not by the coloration of sugars by the sulfuric acid-methanol method. The results are shown in Table 7.

TABLE 7

| | Enzyme action | | |
|---|---|---|---|
| Substrate | C11 enzyme | N75 enzyme | A19 enzyme |
| Maltose | + | + | + |
| Maltotriose | ++ | ++ | ++ |
| Maltotetraose | +++ | +++ | +++ |
| Maltopentaose | +++ | +++ | +++ |
| Maltohexaose | +++ | +++ | +++ |
| Maltoheptaose | +++ | +++ | +++ |
| Isomaltose | − | − | − |
| Isomaltotriose | − | − | − |
| Panose | − | − | − |
| Isopanose | ++ | ++ | ++ |

TABLE 7-continued

| Substrate | Enzyme action | | |
|---|---|---|---|
| | C11 enzyme | N75 enzyme | A19 enzyme |
| Trehalose | – | – | – |
| Kojibiose | + | + | + |
| Nigerose | + | + | + |
| Neotrehalose | + | + | + |
| Cellobiose | – | – | – |
| Gentibiose | – | – | – |
| Maltitol | – | – | – |
| Maltotriitol | + | + | + |
| Lactose | – | – | – |
| Sucrose | – | – | – |
| Erlose | + | + | + |
| Selaginose | – | – | – |
| Maltosyl glucoside | ++ | ++ | ++ |
| Isomaltosyl glucoside | – | – | – |

Note:
Before and after the enzymatic reaction, The symbols "–", "+", "++", and "+++" mean that it showed no change, it showed a slight reduction of the color spot of the substrate and the formation of other reaction product, it showed a high reduction of the color spot of the substrate and the formation of other reaction product, and it showed a substantial disappearance of the substrate spot and the formation of other reaction product, respectively.

As evident from the Table 7, it was revealed that the polypeptide having α-isomaltosylglucosaccharide-forming enzyme activity well acted on saccharide having a glucose polymerization degree of 3 or higher and bearing a maltose structure at their non-reducing ends, among the saccharides tested. It was also found that the polypeptide slightly acted on saccharides, having glucose polymerization degree of two, such as maltose, kojibiose, nigerose, neotrehalose, maltotriitol, and erlose.

Experiment 4-2

Reaction Product from Maltooligosaccharide

To an aqueous solution containing one percent (w/v) of maltose, maltotriose, maltotetraose, or maltopentaose as a substrate was added the polypeptide having α-isomaltosyl-glucosaccgaride-forming enzyme activity, obtained in Experiment 1-3, in an amount of two units/g-solid for maltose and maltotriose, 0.2 unit/g-solid for maltotetraose, and 0.1 unit/g-solid for maltopentaose, followed by incubation at 35° C. and pH 6.0 for 8 hours. After stopping the enzymatic reaction by a 10-minutes incubation, sugar compositions in the reaction mixture were measured by HPLC using "YMC Pack ODS-AQ303", a column commercialized by YMC Co., Ltd., Tokyo, Japan, at a column temperature of 40° C. and a flow rate of 0.5 ml/minutes of water, and using as a detector "RI-8012", a differential refractometer commercialized by Tosoh Corporation, Tokyo, Japan. The results are in Table 8.

TABLE 8

| Saccharide as Reaction product | Substrate | | | |
|---|---|---|---|---|
| | Mlatose | Maltotriose | Maltotetraose | Maltopentaose |
| Glucose | 8.5 | 0.1 | 0.0 | 0.0 |
| Maltose | 78.0 | 17.9 | 0.3 | 0.0 |
| Maltotriose | 0.8 | 45.3 | 22.7 | 1.9 |
| Maltotetraose | 0.0 | 1.8 | 35.1 | 19.2 |
| Maltopentaose | 0.0 | 0.0 | 3.5 | 34.4 |
| Maltohexaose | 0.0 | 0.0 | 0.0 | 4.6 |
| Isomaltose | 0.5 | 0.0 | 0.0 | 0.0 |
| Glucosyl-maltose | 8.2 | 1.2 | 0.0 | 0.0 |
| Glucosyl-maltotriose | 2.4 | 31.5 | 6.8 | 0.0 |
| X | 0.0 | 2.1 | 30.0 | 11.4 |
| Y | 0.0 | 0.0 | 1.4 | 26.8 |
| Z | 0.0 | 0.0 | 0.0 | 1.7 |
| Others | 0.6 | 0.1 | 0.2 | 0.0 |

Note:
In the table, glucosylmaltose means α-isomaltosylglucose alias $6^2$-O-α-glucosylmaltose or panose;
glucosylmaltotriose means α-isomaltosylmaltose alias $6^3$-O-α-glucosylmaltotriose;
X means the α-isomaltosylmaltotriose in the present Experiment, alias $6^4$-O-α-glucosylmaltotetraose;
Y means the α-isomaltosylmaltotetraose in the present Experiment, alias $6^5$-O-α-glucosylmaltopentaose; and
Z means an unidentified saccharide.

As evident from the results in Table 8, it was revealed that, after the action of the polypeptide having α-isomaltosylglucosaccharide-forming enzyme activity, glucose and α-isomaltosylglucose alias $6^2$-O-α-glucosylmaltose or panose were mainly formed from maltose as a substrate; and maltose and α-isomaltosylmaltose alias $6^3$-O-α-glucosylmaltotriose were mainly formed from malotriose as a substrate along with small amounts of glucose, maltotetraose, α-isomaltosylglucose alias $6^2$-O-α-glucosylmaltose, and the product X. Also, it was revealed that maltotriose and the product X were mainly formed from maltotetraose as a substrate along with small amounts of maltose, maltopentaose, α-isomaltosylmaltose alias $6^3$-O-α-glucosylmaltotriose, and the product Y; and maltotetraose and the product Y were mainly formed from maltopentaose as a substrate along with small amounts of maltotriose, maltohexaose, the product X, and the product Z.

The product X as a main product from maltotetraose as a substrate and the product Y as a main product from maltopentaose as a substrate were respectively purified and isolated. The products X and Y were respectively purified on HPLC using "YMC-Pack ODS-A R355-15S-15 12A", a preparative HPLC column commercialized by YMC Co., Ltd., Tokyo, Japan, to isolate a specimen of the product X having a purity of 99.9% or higher from the reaction product from maltotetraose in a yield of about 8.3%, d.s.b., and a specimen of the product Y having a purity of 99.9% or higher from the reaction product from maltopentaose in a yield of about 11.5%, d.s.b.

Figure 2:
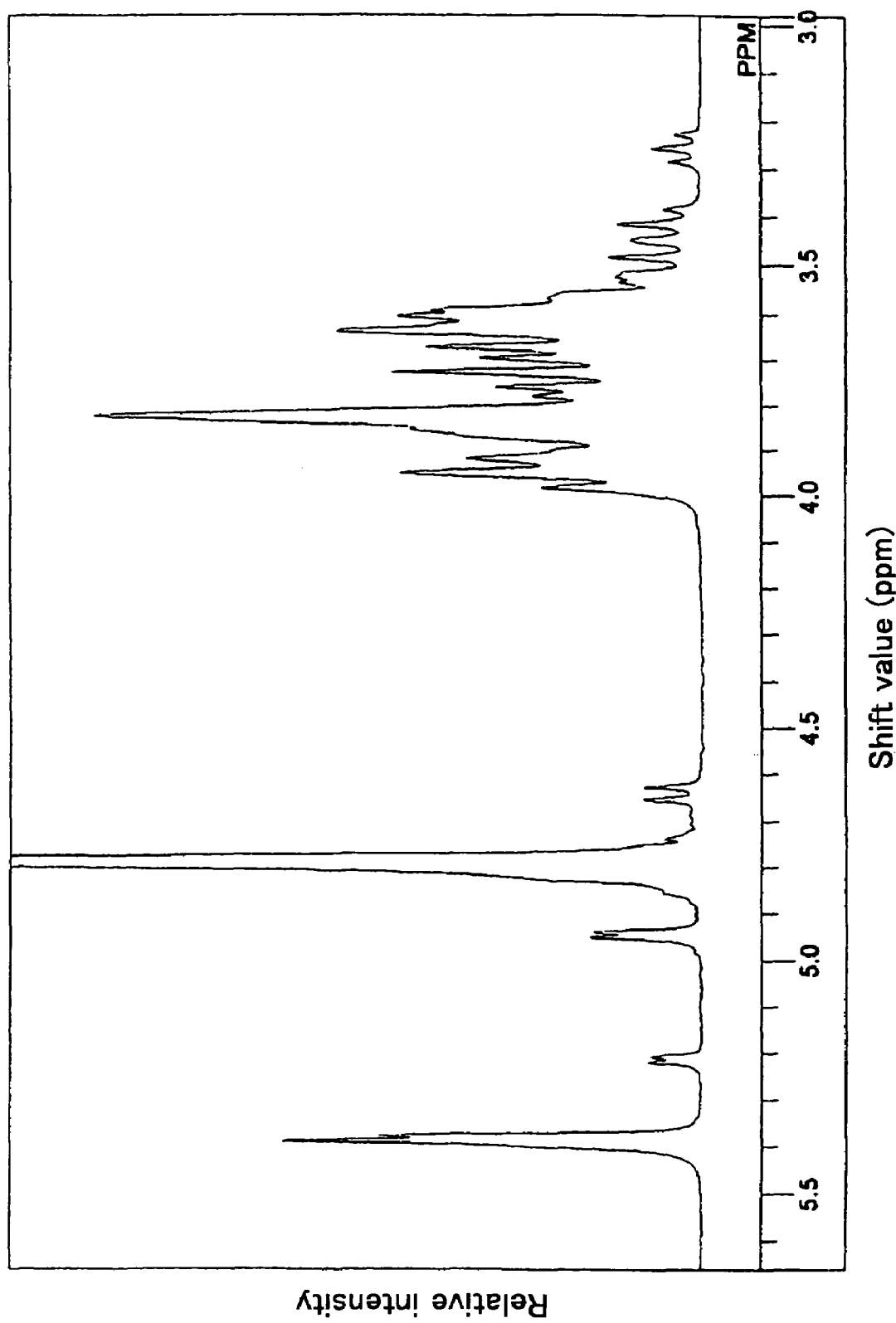
FIG. 2 shows a $^1$H-NMR spectrum of an enzymatic reaction product Y which was obtained from maltopentaose using a polypeptide having α-isomaltosylglucosaccharide-forming enzyme activity.
Figure 3:
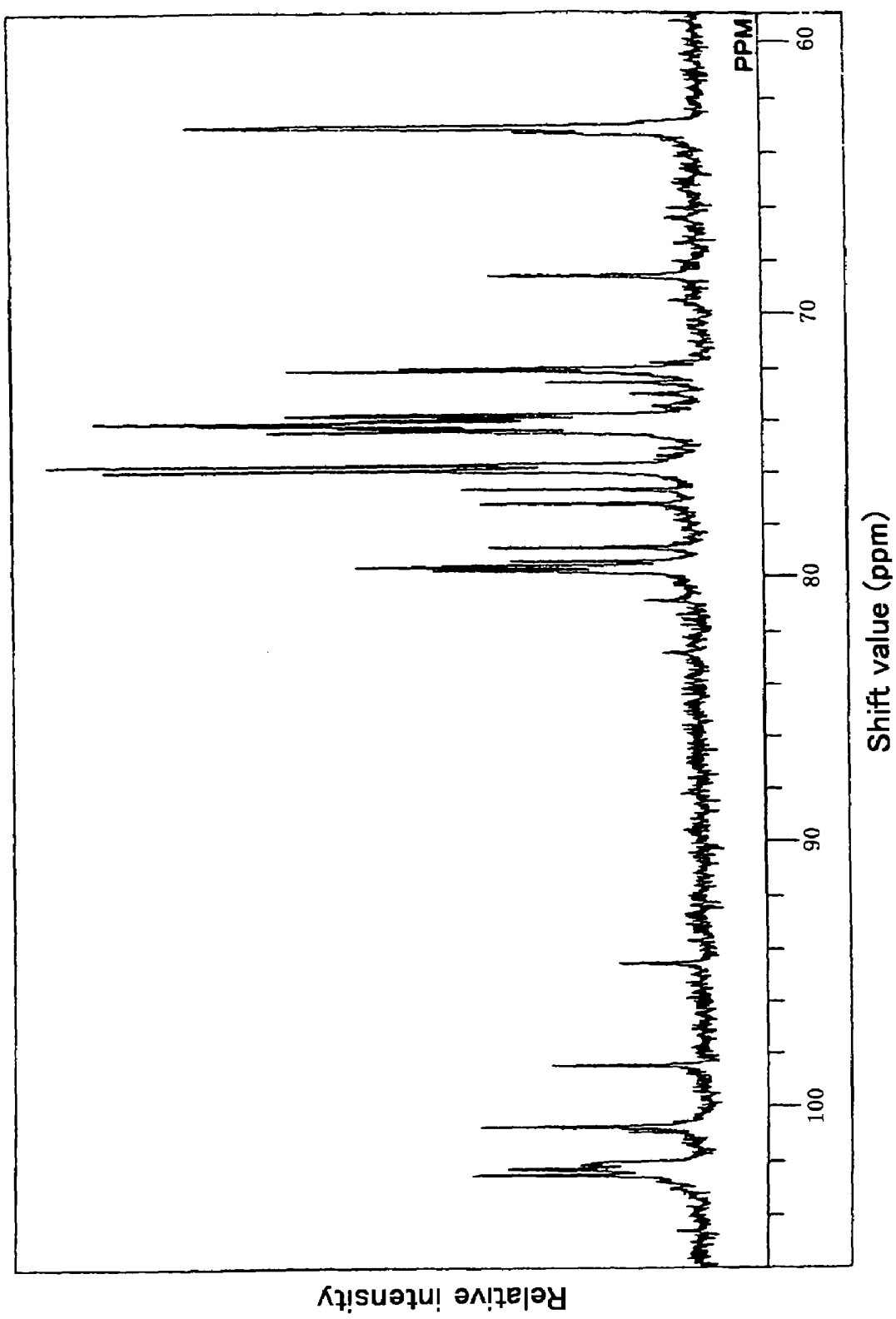
FIG. 3 shows a $^{13}$C-NMR spectrum of an enzymatic reaction product X which was obtained from maltotetraose using a polypeptide having α-isomaltosylglucosaccharide-forming enzyme activity.
Figure 4:
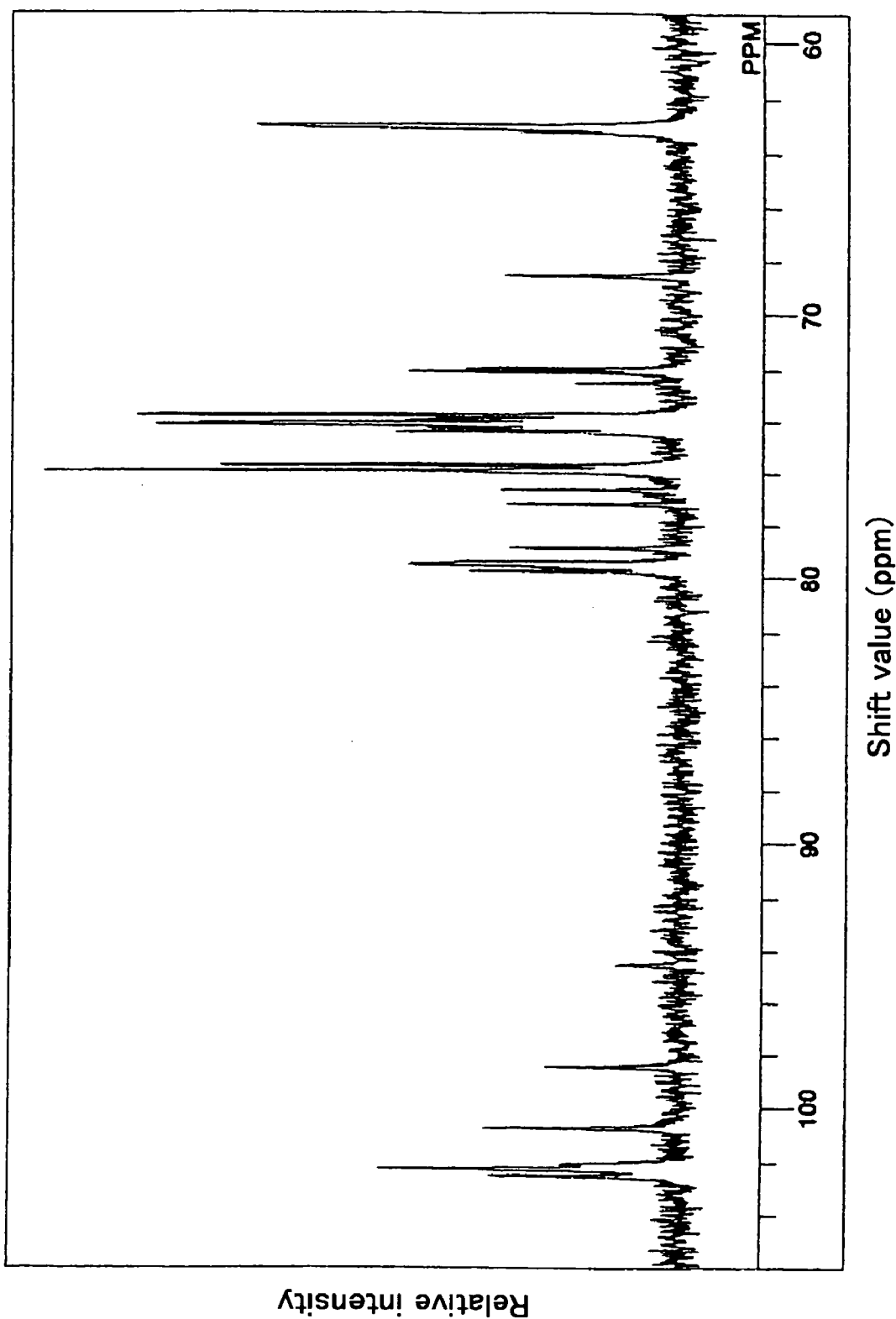
FIG. 4 shows a $^{13}$C-NMR spectrum of an enzymatic reaction product Y which was obtained from maltopentaose using a polypeptide having α-isomaltosylglucosaccharide-forming enzyme activity.

The products X and Y were subjected to methylation analysis and NMR analysis in a usual manner. The results on their methylation analysis are in Table 9. For the results on their NMR analyses, FIGS. 1 and 2 are $^1$H-NMR spectra for the products X and Y, respectively. The 13C-NMR spectra for the products X and Y are FIGS. 3 and 4, respectively. The assignment of the products X and Y are tabulated in Table 10.

TABLE 9

| Analyzed methyl compound | Ratio | |
|---|---|---|
| | Product X | Product Y |
| 2,3,4-trimethyl compound | 1.00 | 1.00 |
| 2,3,6-trimethyl compound | 3.05 | 3.98 |
| 2,3,4,6-tetramethyl compound | 0.82 | 0.85 |

Based on these results, the product X formed from maltotetraose via the action of the polypeptide having α-isomaltosylglucosaccharide-forming enzyme activity was revealed as a pentasaccharide, in which a glucose residue bound via α-linkage to C6-OH of glucose at the non-reducing end of maltotetraose, i.e., α-isomaltosylmaltotriose alias $6^4$-O-α-glucosylmaltotetraose, represented by Formula 1.

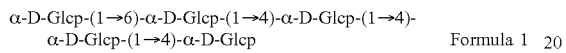

Formula 1

The product Y formed from maltopentaose was revealed as a hexasaccharide, in which a glucose residue bound via α-linkage to C6-OH of glucose at the non-reducing end of maltopentaose, i.e., α-isomaltosylmaltotetraose alias $6^5$-O-α-glucosylmaltopentaose, represented by Formula 2.

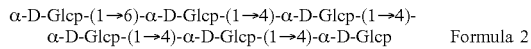

Formula 2

TABLE 10

| Glucose number | Carbon number | Chemical shift on NMR (ppm) | |
|---|---|---|---|
| | | Product X | Product Y |
| a | 1a | 100.8 | 100.8 |
| | 2a | 74.2 | 74.2 |
| | 3a | 75.8 | 75.7 |
| | 4a | 72.2 | 72.2 |
| | 5a | 74.5 | 74.5 |
| | 6a | 63.2 | 63.1 |
| b | 1b | 102.6 | 102.6 |
| | 2b | 74.2 | 74.2 |
| | 3b | 75.8 | 75.7 |
| | 4b | 72.1 | 72.1 |
| | 5b | 74.0 | 74.0 |
| | 6b | 68.6 | 68.6 |
| c | 1c | 102.3 | 102.3 |
| | 2c | 74.2 | 74.2 |
| | 3c | 76.0 | 76.0 |
| | 4c | 79.6 | 79.5 |
| | 5c | 73.9 | 73.9 |
| | 6c | 63.2 | 63.1 |
| d | 1d | 102.2 | 102.3 |
| | 2d | 74.0(α), 74.4(β) | 74.2 |
| | 3d | 76.0 | 76.0 |
| | 4d | 79.8 | 79.5 |
| | 5d | 73.9 | 73.9 |
| | 6d | 63.2 | 63.1 |
| e | 1e | 94.6(α), 98.5(β) | 102.1 |
| | 2e | 74.2(α), 76.7(β) | 74.0(α), 74.4(β) |
| | 3e | 75.9(α), 78.9(β) | 76.0 |
| | 4e | 79.6(α), 79.4(β) | 79.8 |
| | 5e | 72.6(α), 77.2(β) | 73.9 |
| | 6e | 63.4(α), 63.4(β) | 63.1 |
| f | 1f | | 94.6(α), 98.5(β) |
| | 2f | | 74.2(α), 76.7(β) |
| | 3f | | 76.0(α), 78.9(β) |
| | 4f | | 79.6(α), 79.5(β) |
| | 5f | | 72.6(α), 77.2(β) |
| | 6f | | 63.3(α), 63.3(β) |

Based on these results, it was concluded that the polypeptide having α-isomaltosylglucosaccharide-forming enzyme activity acts on maltooligosaccharides as shown below:

1) The polypeptide having α-isomaltosylglucosaccharide-forming enzyme activity acts on as a substrate saccharides with a glucose polymerization degree of two or higher and having α-1,4 glucosidic linkage as a linkage at the non-reducing end, and catalyzes the intermolecular 6-glucosyl-transferring reaction in such a manner of transferring a glucosyl residue at the non-reducing end of the saccharide molecule to C-6 position of the non-reducing end of other saccharide molecule to form both an α-isomaltosylglucosaccharide alias 6-O-α-glucosylmaltooligosaccharide, having a 6-O-α-glucosyl residue and a higher glucose polymerization degree by one as compared with the intact substrate, and a maltooligosaccharide with a reduced glucose polymerization degree by one as compared with the intact substrate; and 2) The polypeptide having α-isomaltosylglucosaccharide-forming enzyme activity slightly catalyzes the 4-glucosyl-transferring reaction and forms small amounts of both a maltooligosaccharide, having an increased glucose polymerization degree by one as compared with the intact substrate, and a maltooligosaccharide having a reduced glucose polymerization degree by one as compared with the intact substrate.

Experiment 4-3

Test on Reducing-power Formation

The following test was carried out to study whether the polypeptide having α-isomaltosylglucosaccharide-forming enzyme activity had the ability of forming reducing-power or not. To a 1% (w/v) aqueous solution of maltotetraose as a substrate was added 0.25 unit/g substrate, d.s.b., of either of purified polypeptide specimen of α-isomaltosylglucosaccharide-forming enzyme from *Bacillus globisporus* C11 obtained by the method in Experiment 1-3, *Bacillus globisporus* N75 obtained by the method in Experiment 2-3, or *Arthrobacter globiformis* A19 obtained by the method in Experiment 3-3, and incubated at 35° C. and at pH 6.0, except that pH 8.4 was used for the enzyme from *Arthrobacter globiformis* A19. During the reaction, a portion of each reaction mixture was sampled at prescribed time intervals and measured for reducing power after keeping at 100° C. for 10 minutes to stop the enzymatic reaction. Before and after the enzymatic reaction, the reducing sugar content and total sugar content were respectively quantified by the Somogyi-Nelson method and anthrone-sulfuric acid method. The percentage of forming reducing power was calculated by the following equation:

Percentage of forming reducing power (%)=$(AR/AT-BR/BT) \times 100$  Equation:

AR: Reducing sugar content after enzymatic reaction.
AT: Total sugar content after enzymatic reaction.
BR: Reducing sugar content before enzymatic reaction.
BT: Total sugar content before enzymatic reaction.

The results are in Table 11.

TABLE 11

| | Percentage of forming reducing power (%) | | |
|---|---|---|---|
| Reaction time (hour) | Enzyme of Strain C11 | Enzyme of Strain N75 | Enzyme of Strain A19 |
| 0 | 0.0 | 0.0 | 0.0 |
| 1 | 0.1 | 0.1 | 0.0 |
| 2 | 0.0 | 0.0 | 0.1 |

TABLE 11-continued

| | Percentage of forming reducing power (%) | | |
|---|---|---|---|
| Reaction time (hour) | Enzyme of Strain C11 | Enzyme of Strain N75 | Enzyme of Strain A19 |
| 4 | 0.1 | 0.0 | 0.0 |
| 8 | 0.0 | 0.1 | 0.1 |

As evident from the results in Table 11, it was revealed that the polypeptide having α-isomaltosylglucosaccharide-forming enzyme activity did not substantially increase the reducing power of the reaction product when acted on maltotetraose as a substrate; the polypeptide having α-isomaltosylglucosaccharide-forming enzyme activity did not have hydrolyzing activity or had only an undetectable level of such activity.

Experiment 4-4

Molecular Weight

Purified specimens of the polypeptide having α-isomaltosylglucosaccharide-forming enzyme activity from *Bacillus globisporus* C11 obtained by the method in Experiment 1-3, *Bacillus globisporus* N75 obtained by the method in Experiment 2-3, and *Arthrobacter globiformis* A19 obtained by the method in Experiment 3-3 were subjected to SDS-PAGE using 7.5% (w/v) of polyacrylamide gel and then determined for their molecular weights by comparing with the dynamics of standard molecular weight markers electrophoresed in parallel, commercialized by Bio-Rad Laboratories, Inc., Brussels, Belgium. It was revealed that the polypeptides from C11, N75, and A19 had molecular weights of about 137,000±20,000 daltons, about 136,000±20,000 daltons, and about 94,000±20,000 daltons, respectively.

Experiment 4-5

Isoelectric Point

Purified specimens of the polypeptide having α-isomaltosylglucosaccharide-forming enzyme activity from *Bacillus globisporus* C11 obtained by the method in Experiment 1-3, *Bacillus globisporus* N75 obtained by the method in Experiment 2–3, and *Arthrobacter globiformis* A19 obtained by the method in Experiment 3-3 were subjected to isoelectrophoresis using a gel containing 2% (w/v) ampholine commercialized by Amersham Biosciences K. K., Tokyo, Japan (old name, Amersham Pharmacia Biotech), and then measured pHs of protein bands and gel to determine their isoelectric points. It was revealed that the polypeptides from C11, N75, and A19 had isoelectric points of about 5.2±0.5, about 7.3±0.5, and about 4.3±0.5, respectively.

Experiment 4-6

Effect of Temperature and pH

Figure 5:
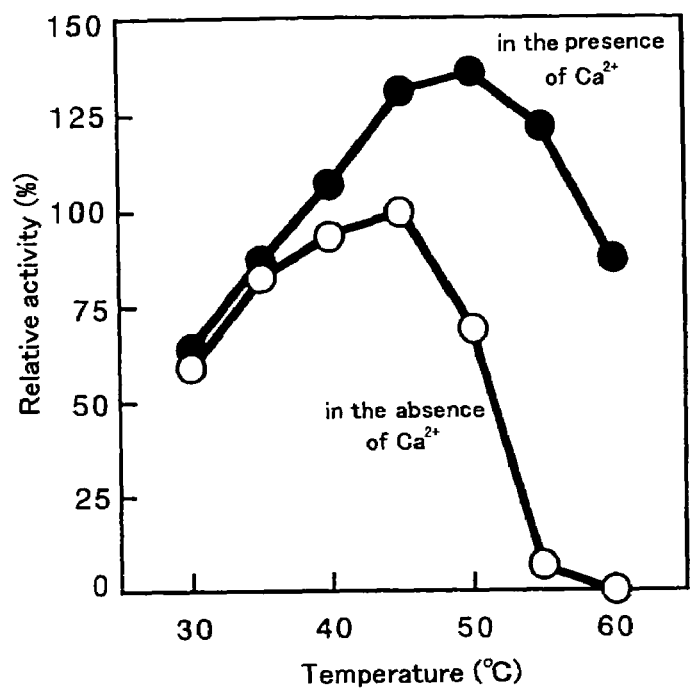
FIG. 5 shows the effect of temperature on α-isomaltosyl-glucosaccharide-forming enzyme activity from a microorganism of *Bacillus globisporus* C11.
Figure 6:
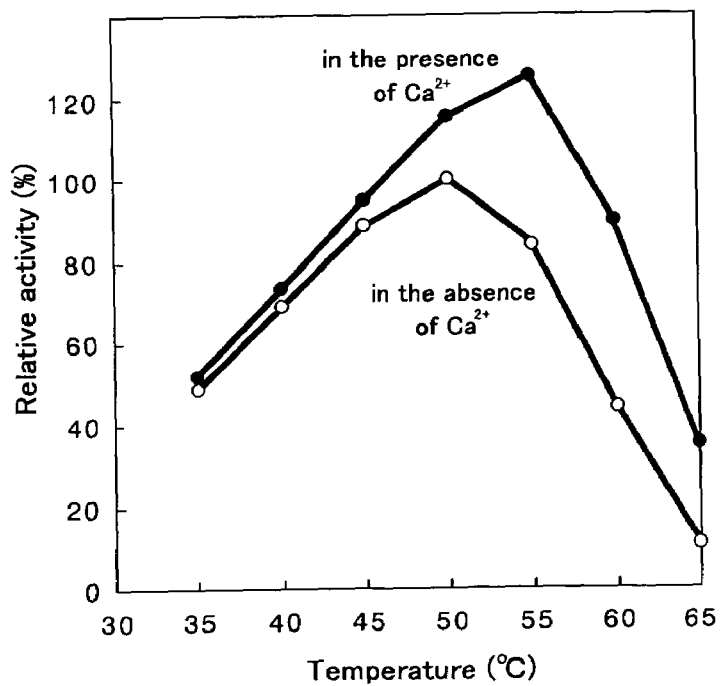
FIG. 6 shows the effect of temperature on α-isomaltosyl-glucosaccharide-forming enzyme activity from a microorganism of *Bacillus globisporus* N75.
Figure 7:
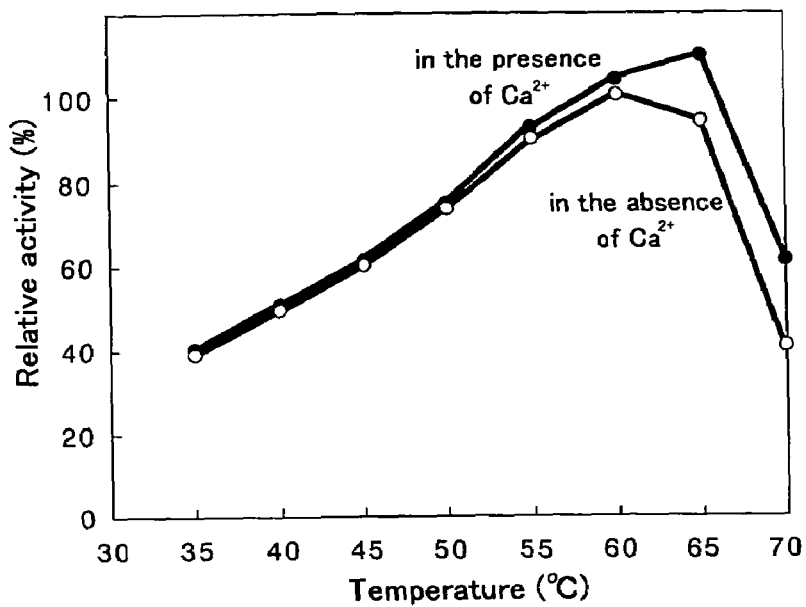
FIG. 7 shows the effect of temperature on α-isomaltosyl-glucosaccharide-forming enzyme activity from a microorganism of *Arthrobacter globiformis* A19.
Figure 8:
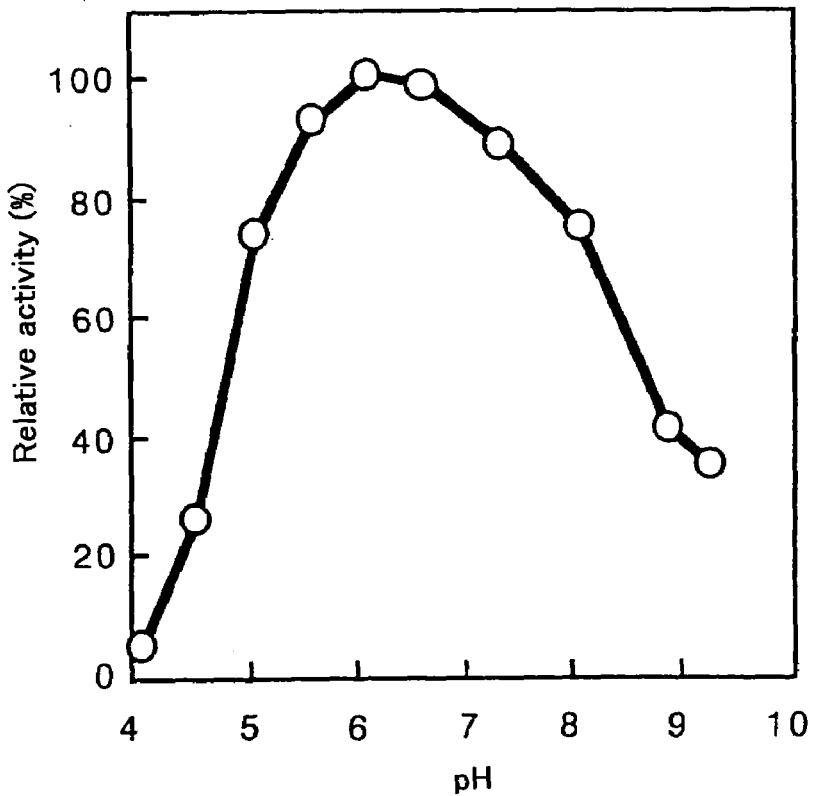
FIG. 8 shows the effect of pH on α-isomaltosylglucosaccharide-forming enzyme activity from a microorganism of *Bacillus globisporus* C11.
Figure 9:
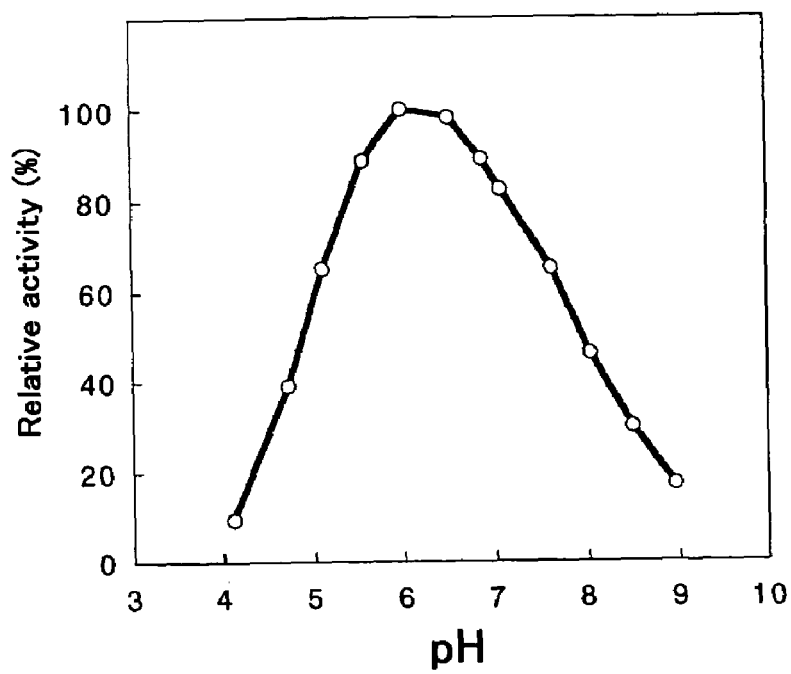
FIG. 9 shows the effect of pH on α-isomaltosylglucosaccharide-forming enzyme activity from a microorganism of *Bacillus globisporus* N75.
Figure 10:
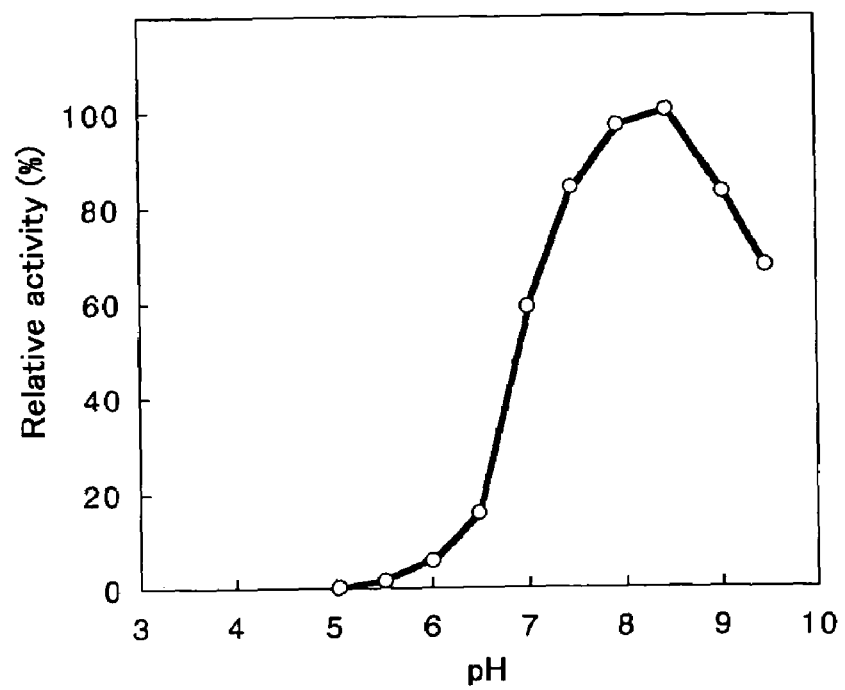
FIG. 10 shows the effect of pH on α-isomaltosylglucosaccharide-forming enzyme activity from a microorganism of *Arthrobacter globiformis* A19.

The effect of temperature and pH on the α-isomaltosylglucosaccharide-forming enzyme activity was examined in accordance with the assay for the α-isomaltosylglucosaccharide-forming enzyme activity under various temperature and pH conditions. The effect of temperature was conducted in the presence or absence of 1 mM $Ca^{2+}$. These results are shown in FIG. 5 (effect of temperature on the polypeptide from a strain C11), FIG. 6 (effect of temperature on the polypeptide from a strain N75), FIG. 7 (effect of temperature on the polypeptide from a strain A19), FIG. 8 (effect of pH on the polypeptide from a strain C11), FIG. 9 (effect of pH on the polypeptide from a strain N75), and FIG. 10 (effect of pH on the polypeptide from a strain A19). The optimum temperature of the polypeptide having α-isomaltosylglucosaccharide-forming enzyme activity from a strain C11 was about 45° C. (in the absence of $Ca^{2+}$) and about 50° C. (in the presence of $Ca^{2+}$) when incubated at pH 6.0 for 60 minutes, and the optimum pH was about 6.0 when incubated at 35° C. for 60 minutes. The optimum temperature of the polypeptide having α-isomaltosylglucosaccharide-forming enzyme activity from a strain N75 was about 50° C. (in the absence of $Ca^{2+}$) and about 55° C. (in the presence of $Ca^{2+}$) when incubated at pH 6.0 for 60 minutes, and the optimum pH was about 6.0 when incubated at 35° C. for 60 minutes. The optimum temperature of the polypeptide having α-isomaltosylglucosaccharide-forming enzyme activity from a strain A19 was about 60° C. (in the absence of $Ca^{2+}$) and about 65° C. (in the presence of $Ca^{2+}$) when incubated at pH 8.4 for 60 min, and the optimum pH was about 8.4 when incubated at 35° C. for 60 minutes.

Experiment 4-7

Stability

Figure 11:
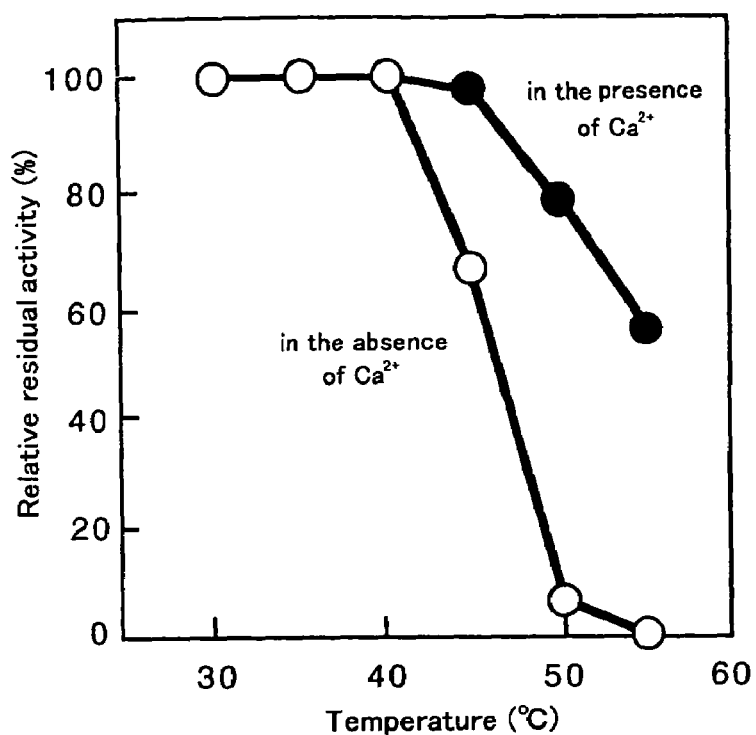
FIG. 11 shows the thermal stability of α-isomaltosylglucosaccharide-forming enzyme from a microorganism of *Bacillus globisporus* C11.
Figure 12:
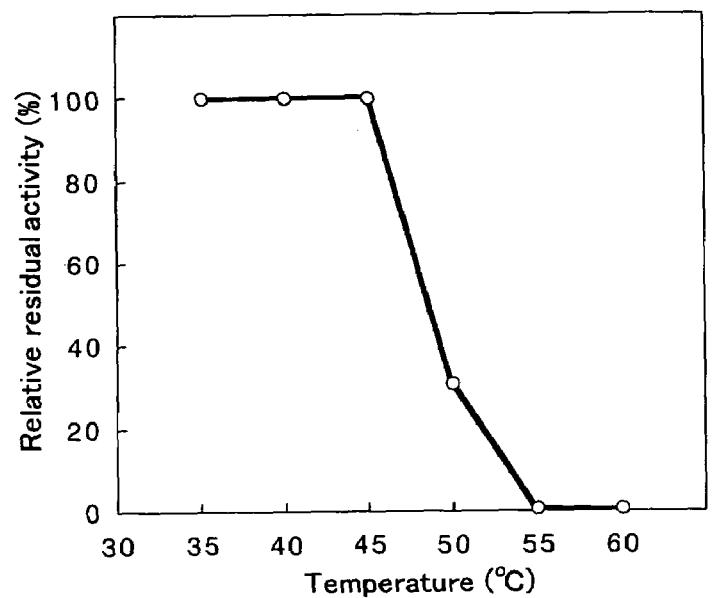
FIG. 12 shows the thermal stability of α-isomaltosylglucosaccharide-forming enzyme from a microorganism of *Bacillus globisporus* N75.
Figure 13:
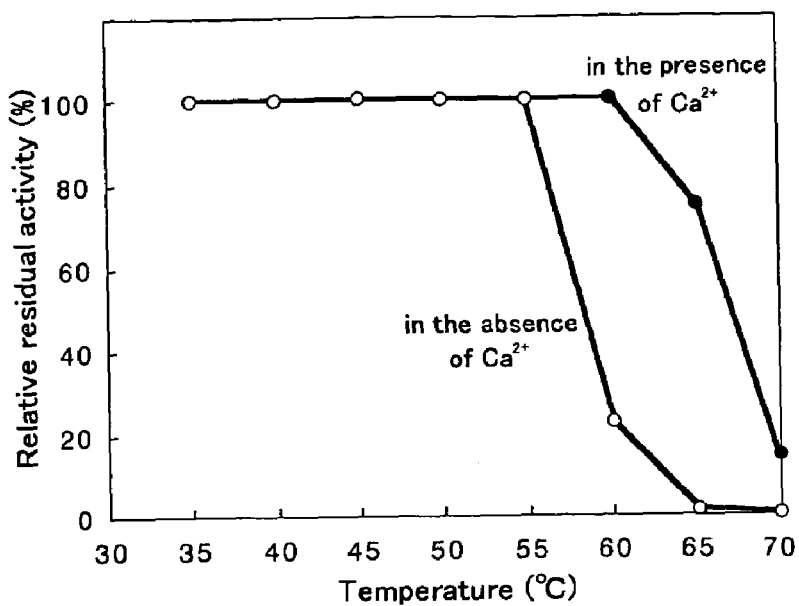
FIG. 13 shows the thermal stability of α-isomaltosylglucosaccharide-forming enzyme from a microorganism of *Arthrobacter globiformis* A19.
Figure 14:
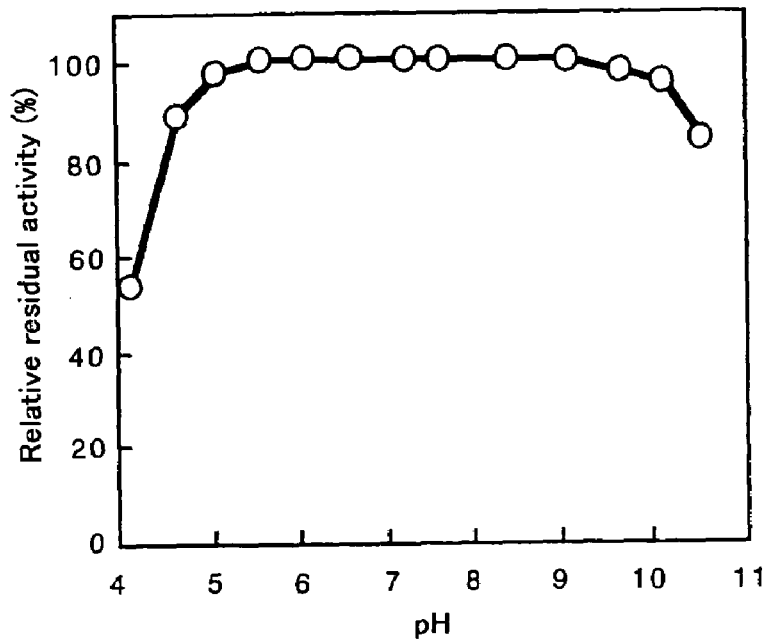
FIG. 14 shows the pH stability of α-isomaltosylglucosaccharide-forming enzyme from a microorganism of *Bacillus globisporus* C11.
Figure 15:
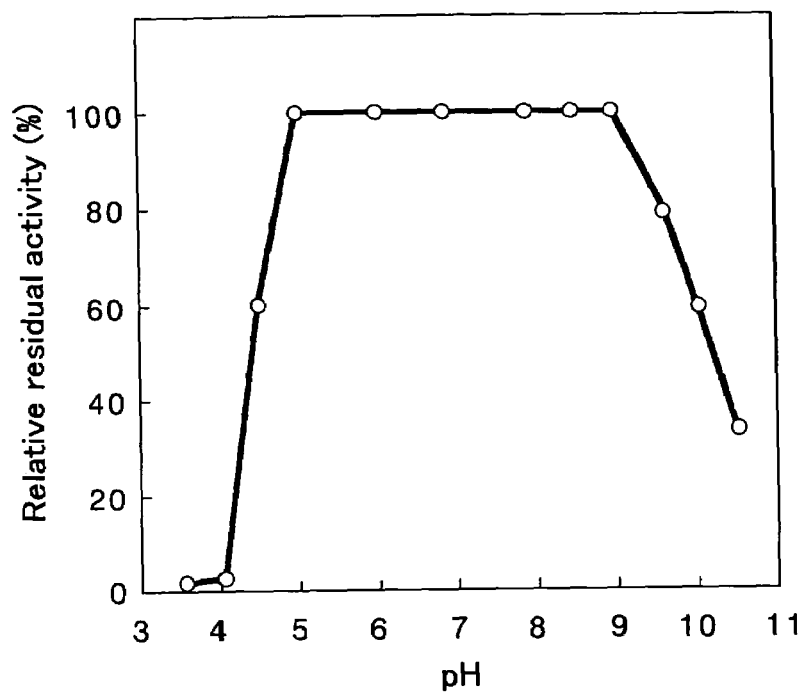
FIG. 15 shows the pH stability of α-isomaltosylglucosaccharide-forming enzyme from a microorganism of *Bacillus globisporus* N75.
Figure 16:
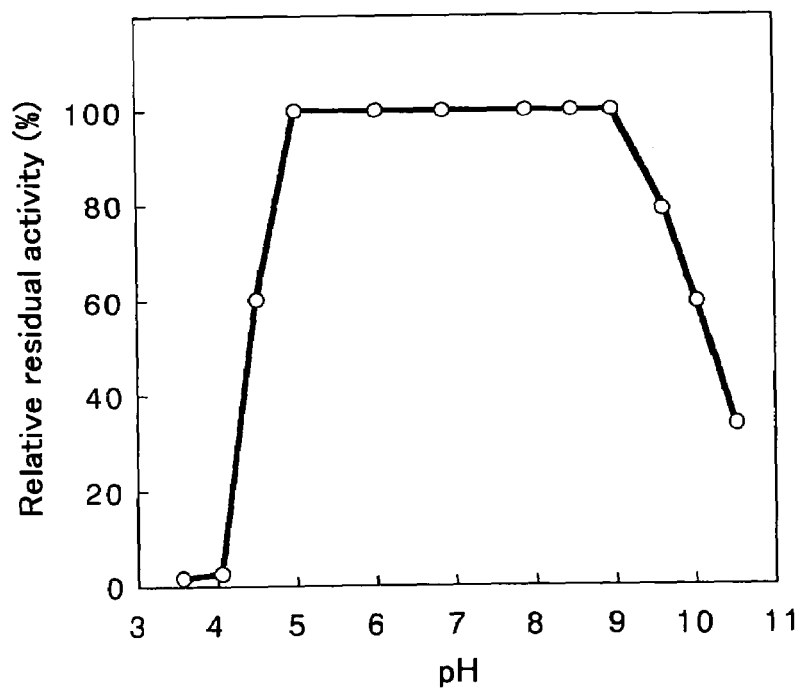
FIG. 16 shows the. pH stability of α-isomaltosylglucosaccharide-forming enzyme from a microorganism of *Arthrobacter globiformis* A19.

The thermal stability of the polypeptide having α-isomaltosylglucosaccharide-forming enzyme activity was determined by incubating the testing polypeptide solution in 20 mM acetate buffer, pH6.0 (in the case of the polypeptide from a strain A19, 20 m M Glycine-NaOH buffer, pH 8.0) at prescribed temperatures for 60 minutes in the presence or absence of 1 mM $Ca^{2+}$, cooling with water the resulting polypeptide solutions, and assaying the residual enzyme activity of each solution. The pH stability of the polypeptide having α-isomaltosylglucosaccharide-forming enzyme activity was determined by keeping the testing polypeptide solutions in 50 mM buffer having prescribed pHs at 4° C. for 24 hours, adjusting the pH of each solution to 6.0 (in the case of the polypeptide from a strain A19, pH 8.0), and assaying the residual enzyme activity of each solution. These results are shown in FIG. 11 (thermal stability of the polypeptide from a strain C11), FIG. 12 (thermal stability of the polypeptide from a strain N75), FIG. 13 (thermal stability of the polypeptide from a strain A19), FIG. 14 (pH stability of the polypeptide from a strain C11), FIG. 15 (pH stability of the polypeptide from a strain N75), and FIG. 16 (pH stability of the polypeptide from a strain A19). The thermal stability of the polypeptide having α-isomaltosylglucosaccharide-forming enzyme activity from a strain C11 was up to about 40° C. (in the absence of $Ca^{2+}$) and about 45° C. (in the presence of $Ca^{2+}$), and pH stability of about 5.0 to about 10.0. The thermal stability of the polypeptide having α-isomaltosylglucosaccharide-forming enzyme activity from a strain N75 was up to about 45° C. (in the absence of $Ca^{2+}$) and about 50° C. (in the presence of $Ca^{2+}$), and pH stability of about 5.0 to about 9.0. The thermal stability of the polypeptide having α-isomaltosylglucosaccharide-forming enzyme activity from a strain A19 was up to about 55° C. (in the absence of $Ca^{2+}$) and about 60° C. (in the presence of $Ca^{2+}$), and pH stability of about 5.0 to about 9.0.

EXPERIMENT 5

Partial Amino Acid Sequence

Experiment 5-1

N-Terminal Amino Acid Sequence

Purified specimens of the polypeptide having α-isomaltosylglucosaccharide-forming enzyme activity from *Bacillus globisporus* C11 obtained by the method in Experiment 1-3, *Bacillus globisporus* N75 obtained by the method in Experiment 2-3, and *Arthrobacter globiformis* A19 obtained by the method in Experiment 3-3 were subjected to N-terminal sequence analysis by using "gas-phase protein sequencer model 473A", an apparatus of Applied Biosystems, 850 Lincoln Centre Drive, Foster City, U.S.A. It was revealed that the polypeptides having α-isomaltosyl-transferring enzyme activity from strains C11, N75, and A19 had amino acid sequences of SEQ ID NOs: 7, 19, and 26, respectively.

Experiment 5-2

Internal Amino Acid Sequences of the Polypeptide from *Bacillus globisporus* C11

A part of a purified specimen of polypeptide having α-isomaltosylglucosaccharide-forming enzyme activity, obtained in Experiment 1-3, was dialyzed against 10 mM Tris-HCl buffer (pH 9.0), and the dialyzed solution was diluted with a fresh preparation of the same buffer to give a concentration of about one mg/ml. One milliliter of the diluted solution as a test sample was admixed with 10 μg of trypsin commercialized by Wako Pure Chemicals, Ltd., Tokyo, Japan, and incubated at 30° C. for 22 hours to form peptides. The resulting hydrolyzate was subjected to reverse-phase HPLC to separate the peptides using "μ-BONDAPAK C18 column", having a diameter of 2.1 mm and a length of 150 mm, a product of Waters Chromatography Div., MILLIPORE Corp., Milford, USA, pre-equilibrated with 0.1% (v/v) trifluoroacetate containing 8% (v/v) acetonitrile, at a flow rate of 0.9 ml/minutes and at ambient temperature, and using a linear gradient of acetonitrile increasing from 8% (v/v) to 40% (v/v) in 0.1% (v/v) trifluoroacetate over 120 minutes. Peptide fragments eluted from the column were detected by monitoring the absorbance at a wavelength of 210 nm. Ten peptide fragments, P8 (Retention time (Rt): about 8 minutes), P20 (Rt: about 20 minutes), P56 (Rt: about 56 minutes), P60 (Rt: about 60 minutes), P62 (Rt: about 62 minutes), P64 (Rt: about 64 minutes), P75 (Rt: about 75 minutes), P82 (Rt: about 82 minutes), P88 (Rt: about 88 minutes), P99 (Rt: about 99 minutes), which were separated well from other peptides, were separately collected and dried in vacuo and then dissolved in a 200 μl solution of 0.1% (v/v) trifluoroacetate and 50% (v/v) acetonitrile. Each peptide fragment had amino acid sequences of SEQ ID NOs: 8 to 17 when these amino acid sequences were analyzed by the protein sequencer used in Experiment 5-1.

Experiment 5-3

Internal Amino Acid Sequences of the Polypeptide from *Bacillus globisporus* N75

A part of a purified specimen of polypeptide having α-isomaltosylglucosaccharide-forming enzyme activity, obtained in Experiment 2-3, was dialyzed against 10 mM Tris-HCl buffer (pH 9.0), and the dialyzed solution was diluted with a fresh preparation of the same buffer to give a concentration of about one mg/ml. One milliliter of the diluted solution as a test sample was admixed with 20 μg of "Lysyl Endopeptidase" commercialized by Wako Pure Chemicals, Ltd., Tokyo, Japan, and incubated at 30° C. for 24 hours to form peptides. The resulting hydrolyzate was subjected to reverse-phase HPLC to separate the peptides using "μ-BONDASPHERE C18 column", having a diameter of 3.9 mm and a length of 150 mm, a product of Waters Chromatography Div., MILLIPORE Corp., Milford, USA, pre-equilibrated with 0.1% (v/v) trifluoroacetate containing 8% (v/v) acetonitrile, at a flow rate of 0.9 ml/minutes and at ambient temperature, and using a linear gradient of acetonitrile increasing from 8% (v/v) to 36% (v/v) in 0.1% (v/v) trifluoroacetate over 120 minutes. Peptide fragments eluted from the column were detected by monitoring the absorbance at a wavelength of 210 nm. Five peptide fragments, PN47 (Rt: about 47 minutes), PN59 (Rt: about 59 minutes), PN67 (Rt: about 67 minutes), PN87 (Rt: about 87 minutes), PN89 (Rt: about 89 minutes), which were separated well from other peptides, were separately collected and dried in vacuc and then dissolved in a 200 μl solution of 0.1% (v/v) trifluoroacetate and 50% (v/v) acetonitrile. Each peptide fragment had amino acid sequences of SEQ ID NOs: 20 to 24 when these amino acid sequences were analyzed by the protein seauencer used in Experiment 5-1.

Experiment 5-4

Internal Amino Acid Sequences of the Polypeptide from *Arthrobacter globiformis* A19

A part of a purified specimen of polypeptide having α-isomaltosylglucosaccharide-forming enzyme activity, obtained in Experiment 3-3, was dialyzed against 10 mM Tris-HCl buffer (pH 9.0), and the dialyzed solution was diluted with a fresh preparation of the same buffer to give a concentration of about one mg/ml. One milliliter of the diluted solution as a test sample was admixed with 20 μg of "Lysyl Endopeptidase" commercialized by Wako Pure Chemicals, Ltd., Tokyo, Japan, and incubated at 30° C. for 24 hours to form peptides. The resulting hydrolyzate was subjected to reverse-phase HPLC to separate the peptides using "μ-BONDASPHERE C18 column", having a diameter of 2.1 mm and a length of 150 mm, a product of Waters Chromatography Div., MILLIPORE Corp., Milford, USA, pre-equilibrated with 0.1% (v/v) trifluoroacetate containing 16% (v/v) acetonitrile, at a flow rate of 0.9 ml/minutes and at ambient temperature, and using a linear gradient of acetonitrile increasing from 16% (v/v) to 36% (v/v) in 0.1% (v/v) trifluoroacetate over 120 minutes. Peptide fragments eluted from the column were detected by monitoring the absorbance at a wavelength of 210 nm. Five peptide fragments, PA39 (Rt: about 39 minutes), PA81 (Rt: about 81 minutes), PA86 (Rt: about 86 minutes), PA92 (Rt: about 92 minutes), PA104 (Rt: about 104 minutes), which were separated well from other peptides, were separately collected and dried in vacuo and then dissolved in a 200 μl Lsolution of 0.1% (v/v) trifluoroacetate and 50% (v/v) acetonitrile. Each peptide fragment had amino acid sequences of SEQ ID NOs: 27to 31 when these amino acid sequences were analyzed by the protein sequencer used in Experiment 5-1.

EXPERIMENT 6

Preparation of a Recombinant DNA Containing a DNA Encoding Polypeptide from *Bacillus globisporus* C11 and a Transformant

Experiment 6-1

Preparation of Chromosomal DNA

A liquid culture medium consisting 2% (w/v) of "PINE-DEX #4", a partial starch hydrolyzate, 1.0% (w/v) of "ASA-HIMEAST", a yeast extract, 0.1% (w/v) of dipotassium phosphate, 0.06% (w/v) of sodium phosphate dodeca-hydrate, 0.05% (w/v) of magnesium sulfate hepta-hydrate, and water was placed in 500-ml Erlenmeyer flasks in a respective amount of 100 ml, sterilized by autoclaving at 121° C. for 20 minutes, cooled and inoculated with *Bacillus globisporus* C11, followed by culturing under rotary-shaking conditions at 27° C. and 230 rpm for 24 hours. The cells collected from the culture by centrifugation were suspended in TES buffer (pH 8.0), the suspended solution was admixed with lysozyrne to give a concentration of 0.05% (w/v), and incubated at 37° C. for 30 minutes. After freezing the lysate at BOG for one hour, the lysate was added with TES buffer (pH 9.0)and heated to 60° C. The solution was added with a mixture of TES buffer and phenol, and was vigorously shook for five minute in an ice bath, and the supernatant was collected by centrifugation. The supernatant was added twice volume of cold ethanol, and resulting crude precipitate was collected as a crude chromosomal DNA. The crude chromosomal DNA was dissolved in SSC buffer (pH 7.1), and admixed with 7.5 µg of ribonuclease and 125 µg of proteinase, and incubated 37° C. for one hour. The chromosomal DNA was extracted from the reactant by adding chloroform/isoamylalcohol mixture, then added cold ethanol, and the resulting precipitate containing chromosomal DNA was collected. The purified chromosomal DNA, obtained according to the method described above, was dissolved in SSC buffer (pH 7.1) to give a concentration of about one mg/ml and frozen at −80° C.

Experiment 6-2

Preparation of a Transformant. BGC2

One milliliter of purified chromosomal DNA solution, prepared by the method in Experiment 6-1, was admixed with about 35 units of a restriction enzyme, Sau 3AI, and incubated at 37° C. for 20 minutes for partial digestion of the chromosomal DNA. The resulting DNA fragments corresponding to about 2,000 to 6,000 base pairs were collected by sucrose density-gradient centrifugation. A plasmid vector, Bluescript II SK(+), commercialized by Stratagene Cloning System, was completely digested with a restriction enzyme, Barn HI by conventional method. A recombinant DNA was obtained by ligating 0.5 µg of the digested plasmid vector with about 5 µg of the DNA fragments prepared before by using a "DNA ligation kit", commercialized by Takara Shuzo Co., Ltd., according to the method described in a document attached with the kit. Then, a gene library was prepared by transforming 100 µl portion of the competent cell, "Epicurian Coli XL2-Blue", commercialized by Stratagene Cloning System, with the recombinant DNA by conventional competent cell method. The transformants thus obtained as gene library were inoculated into a fresh agar plate medium (pH 7.0) containing 10 g/L of tryptone, 5 g/L of yeast extract, 5 g/L of sodium chloride, 100 mg/L of ampicillin sodium salt, and 50 mg/L of 5-bromo-4-chloro-3-indolyl-β-galactoside, and incubated at 37° C. for 24 hours. About five thousand white colonies grown on the plate were transferred to and fixed on a nylon membrane, "Hybond-N+", commercialized by Amasham Bioscience K. K. An oligonucleotide having a nucleotide sequence of "5'-GGNTTYATGAAYTTYAGRTGGGA-3'" was chemically synthesized on the bases of an amino acid sequence of fourth to eleventh of SEQ ID NO: 16, disclosed by the method in Experiment 5-2. A synthetic DNA (probe 1) was obtained by labeling the oligonucleotide with radioisotope using [γ-$^{32}$P]ATP and T4 polynucleotide kinase according to the conventional method. Subsequently, two types of transformants showing remarkable hybridization with probe 1 were selected from the colonies fixed on the nylon membrane obtained before, using conventional colony hybridization. The recombinant DNAs were collected from these two types of transformants by conventional method. On the other hand, probe 2 having the nucleotide sequence of "5'-GAYGCNTGGATGTTYGGNGAYTGG-3'" was chemically synthesized based on a amino acid sequence of fourth to eleventh of SEQ ID NO: 17 and labeled with radioisotope in the same manner. The recombinant DNAs obtained and probe 2 were used for conventional southern-hybridization, and a recombinant DNA showing a remarkable hybridization with probe 2 was selected. A transformant thus selected was named "BGC2".

Experiment 6-3

Analysis of DNA Sequence

Figure 17:
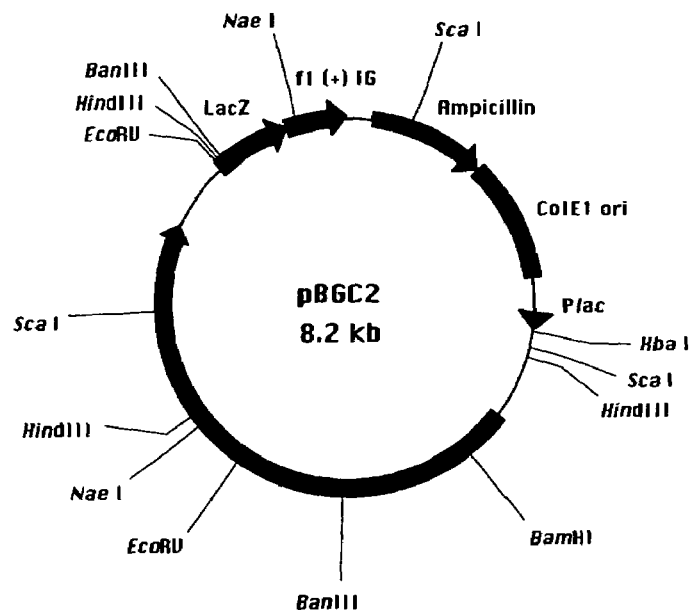
FIG. 17 shows a restriction enzyme map of a recombinant DNA, pBGC2, of the present invention. In the figure, a section indicated with a black bold line is a DNA encoding a polypeptide having α-isomaltosyl-transferring enzyme activity from a microorganism of *Bacillus globisporus* C11.

According to the conventional method, a transformant, BGC2, obtained by the method in Experiment 6-2, was inoculated into L-broth medium (pH 7.0) containing 100 µg/ml of ampicillin sodium salt, and cultured under rotary-shaking conditions at 37° C. for 24 hours. After the completion of the culture, cells were collected by centrifugation, and the recombinant DNA was extracted from the cells by conventional alkaline-SDS method. When the nucleotide sequence of the recombinant DNA was analyzed by conventional dideoxy method, it was revealed that the recombinant DNA contained a DNA having the nucleotide sequence of SEQ ID NO: 18, 5,294 base pairs, which originated from *Bacillus globisporus* C11. In the recombinant DNA, as shown in FIG. 17, the DNA was ligated at downstream of recognition site of a restriction enzyme, Xba I. The amino acid sequence deduced from the nucleotide sequence is as shown in parallel in SEQ ID NO: 18. The amino acid sequence was compared with amino acid sequences of polypeptide of the present invention, i.e., the N-terminal amino acid sequence of SEQ ID NO: 7 disclosed by the method in Experiment 5-1 and the internal partial amino acid sequences of SEQ ID NO: 8 to 17 disclose by the method in Experiment 5-2. An amino acid sequence of SEQ ID NO: 7 was completely identical with that of 36th to 44th of the amino acid sequence shown in parallel in SEQ ID NO: 18. Amino acid sequences of SEQ ID NOs:8, 9, 10, 11, 12,13, 14, 15, 16, and 17 were completely identical with those of 823rd to 832nd, 576th to 589th, 874th to 904th, 1117th to 1141st, 657th to 670th, 367th to 399th, 970th to 993rd, 938th to 953rd, 279th to 295th, and 632nd to 651st of the amino acid sequence shown in parallel in SEQ ID NO: 18, respectively. Since the nucleotide sequence of 4,783rd to 4785th of SEQ ID NO: 18 encodes a codon for terminating the translation (stop codon, 5'-TAA-3'), it is revealed that C-terminal amino acid of the polypeptide of the present invention is glutamic acid (1,284th amino acid of the amino acid sequence shown in parallel in SEQ ID NO: 18). These results indicate that the polypeptide of the present invention contains the amino acid sequence of SEQ ID NO: 1, and that the polypeptide is encoded by the DNA having the nucleotide sequence of SEQ ID NO: 4 in the case of *Bacillus globisporus* C11. An amino acid sequence of the first to 35th of that showing in parallel in SEQ ID NO: 18 was presumed to be a secretion signal sequence of the polypeptide. According to the results described above, it was revealed that the precursor peptide of the polypeptide before secretion had the amino acid sequence shown in parallel in SEQ ID NO: 18, and the amino acid sequence was encoded by the nucleotide sequence of SEQ ID NO: 18. The recombinant DNA prepared and confirmed the nucleotide sequence as described above was named "pBGC2".

EXPERIMENT 7

Preparation of a Recombinant DNA Containing a DNA Encoding Polypeptide from *Bacillus globisporus* N75 and a Transformant Experiment 7-1

Preparation of Chromosomal DNA

A liquid culture medium consisting 2% (w/v) of "PINE-DEX #4", a partial starch hydrolyzate, 1.0% (w/v) of "ASA-HIMEAST", a yeast extract, 0.1% (w/v) of dipotassium phosphate, 0.06% (w/v) of sodium phosphate dodeca-hydrate, 0.05% (w/v) of magnesium sulfate hepta-hydrate, and water was placed in 500-ml Erlenmeyer flasks in a respective amount of 100 ml, sterilized by autoclaving at 121° C. for 20 minutes, cooled and inoculated with *Bacillus globisporus* N75, followed by culturing under rotary-shaking conditions at 27° C. and 230 rpm for 24 hours. The cells collected from the culture by centrifugation were suspended in TES buffer (pH 8.0), the suspended solution was admixed with lysozyme to give a concentration of 0.05% (w/v), and incubated at 37° C. for 30 minutes. After freezing the lysate at −80° C. for one hour, the lysate was added with TES buffer (pH 9.0) and heated to 60° C. The solution was added with a mixture of TES buffer and phenol, and was vigorously shook for five minute in an ice bath, and the supernatant was collected by centrifugation. The supernatant was added twice volume of cold ethanol, and resulting crude precipitate was collected as crude chromosomal DNA. The crude chromosomal DNA was dissolved in SSC buffer (pH 7.1), and admixed with 7.5 µg of ribonuclease and 125 µg of proteinase, and incubated 37° C. for one hour. The chromosomal DNA was extracted from the reactant by adding chloroform/isoamylalcohol mixture, then added cold ethanol, and the resulting precipitate containing chromosomal DNA was collected. The purified chromosomal DNA, obtained according to the method described above, was dissolved in SSC buffer (pH 7.1) to give a concentration of about one mg/ml and frozen at −80° C.

Experiment 7-2

Preparation of a Transformant, BGN2

One hundred µl (0.1 ml) of purified chromosomal DNA solution, prepared by the method in Experiment 7-1, was admixed with about 200 units of a restriction enzyme, Kpn I, and incubated at 37° C. for 16 hours to digest the chromosomal DNA. The resulting DNA fragments were separated by agarose gel electrophoresis, and DNA fragments corresponding to about 3,000 to 7,000 base pairs were collected. A plasmid vector, Bluescript II SK(+), commercialized by Stratagene Cloning System, was completely digested with a restriction enzyme, Kpn I. A recombinant DNA was obtained by ligating 0.5 µg of the digested plasmid vector with about 5 µg of the DNA fragments prepared before by using a "DNA ligation kit", commercialized by Takara Shuzo Co., Ltd., according to the method described in a document attached with the kit. Then, a gene library was prepared by transforming 100 µl portion of the competent cell, "Epicurian Coli XL2-Blue", commercialized by Stratagene Cloning System, with the recombinant DNA by conventional competent cell method. The transformants thus obtained as gene library were inoculated into a fresh agar plate medium (pH 7.0) containing 10 g/L of tryptone, 5 g/L of yeast extract, 5 g/L of sodium chloride, 100 mg/L of ampicillin sodium salt, and 50 mg/L of 5-bromo-4-chloro-3-indolyl-β-galactoside, and incubated at 37° C. for 24 hours. About 2,500 white colonies grown on the plate were transferred to and fixed on a nylon membrane, "Hybond-N+", commercialized by Amasham Bioscience K. K. An oligonucleotide having a nucleotide sequence of "5'-GAYGCNTGGATGTTYGGNGAYTGG-3'" was chemically synthesized on the bases of an amino acid sequence of fourth to eleventh of SEQ ID NO: 24, which disclosed by the method in Experiment 5-3. A synthetic DNA (probe 1) was obtained by labeling the oligonucleotide with radioisotope using [γ-$^{32}$P]ATP and T4 polynucleotide kinase according to the conventional method. Subsequently, three types of transformant showing remarkable hybridization with probe 1 were selected from the colonies fixed on the nylon membrane obtained before, using conventional colony hybridization. The recombinant DNAs were collected from these three types of transformant by conventional method. On the other hand, probe 2 having the nucleotide sequence of "5'-GTNAAYCARAAYCAYTGGTTYTA-3'" was chemically synthesized based on a amino acid sequence of fourteenth to twenty-first of SEQ ID NO: 23 and labeled with radioisotope in the same manner. The recombinant DNAs obtained and probe 2 were used for conventional southern-hybridization, and a recombinant DNA showing a remarkable hybridization with probe 2 was selected. A transformant thus selected was named "BGN2".

Experiment 7-3

Analysis of DNA Sequence

Figure 18:
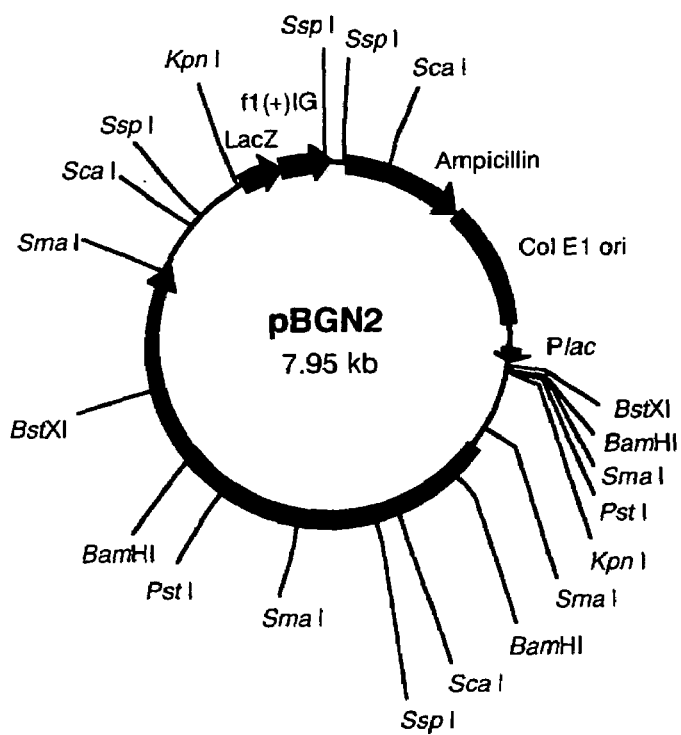
FIG. 18 shows a restriction enzyme map of a recombinant DNA, pBGN2, of the present invention. In the figure, a section indicated with a black bold line is a DNA encoding a polypeptide having α-isomaltosyl-transferring enzyme activity from a microorganism of *Bacillus globisporus* N75.

According to the conventional method, the transformant, BGN2, obtained by the method in Experiment 7-2, was inoculated into L-broth medium (pH 7.0) containing 100 µg/ml of ampicillin sodium salt, and cultured under rotary-shaking conditions at 37° C. for 24 hours. After the completion of the culture, cells were collected by centrifugation, and the recombinant DNA was extracted from the cells by conventional alkaline-SDS method. When the nucleotide sequence of the recombinant DNA was analyzed by conventional dideoxy method, it was revealed that the recombinant DNA contained a DNA having the nucleotide sequence of SEQ ID NO: 25, 4,991 base pairs, which originated from *Bacillus globisporus* N75. In the recombinant DNA, as shown in FIG. 18, the DNA was ligated at downstream of recognition site of a restriction enzyme, Kpn I. The amino acid sequence deduced from the nucleotide sequence is as shown in parallel in SEQ ID NO: 25. The amino acid sequence was compared with amino acid sequences of polypeptide of the present invention, i.e., the N-terminal amino acid sequence of SEQ ID NO: 19 disclosed by the method in Experiment 5-1 and the internal partial amino acid sequences of SEQ ID NOs:20 to 24 disclosed by the method in Experiment 5-3. An amino acid sequence of SEQ ID NO: 19 was completely identical with that of 36th to 43rd of the amino acid sequence shown in parallel in SEQ ID NO: 25. Amino acid sequences of SEQ ID NOs:20, 21, 22, 23, and 24were completely identical with those of 907th to925th, 367th to 386th, 1,034th to 1,058th, 996th to 1,020th, and 632nd to 642nd of the amino acid sequence shown in parallel in SEQ ID NO: 25, respectively. Since the nucleotide sequence of 4,294th to 4,296th of SEQ ID NO: 25encodes a codon for terminating the translation (stop codon, 5'-TAA-3'), it is revealed that C-terminal amino acid of the polypeptide of the present invention is glutamine (1,286th amino acid of the amino acid sequence shown in parallel in SEQ ID NO: 25). These results indicate that the polypeptide of the present invention contains the amino acid sequence of SEQ ID NO: 2, and that the polypeptide is encoded by the DNA having the nucleotide sequence of SEQ ID NO: 5 in the case of *Bacillus globisporus* N75. An amino acid sequence of the first to 35th of that showing in parallel in SEQ ID NO: 25 was presumed to be a secretion signal sequence of the polypeptide. According to the results described above, it was revealed that the precursor peptide of the polypeptide before secretion had the amino acid sequence shown in parallel in SEQ ID NO: 25, and the amino acid sequence was encoded by the nucleotide sequence of SEQ ID NO: 25. The recombinant DNA prepared and confirmed the nucleotide sequence as described above was named "pBGN2".

EXPERIMENT 8

Preparation of a Recombinant DNA Containing a DNA Encoding Polypeptide from *Arthrobacter globiformis* A19 and a Transformant Experiment 8-1

Preparation of Chromosomal DNA

A liquid culture medium consisting 2% (w/v) of "PINE-DEX #4", a partial starch hydrolyzate, 1.0% (w/v) of "ASA-HIMEAST", a yeast extract, 0.1% (w/v) of dipotassium phosphate, 0.06% (w/v) of sodium phosphate dodeca-hydrate, 0.05% (w/v) of magnesium sulfate hepta-hydrate, and water was placed in 500-ml Erlenmeyer flasks in a respective amount of 100 ml, sterilized by autoclaving at 121° C. for 20 minutes, cooled and inoculated with *Arthrobacter globiformis* A19, followed by culturing under rotary-shaking conditions at 27° C. and 230 rpm for 24 hours. The cells collected from the culture by centrifugation were suspended in TES buffer (pH 8.0), the suspended solution was admixed with lysozyme to give a concentration of 0.05% (w/v), and incubated at 37° C. for 30 minutes. After freezing the lysate at −80° C. for one hour, the lysate was added with TES buffer (pH 9.0) and heated to 60° C. The solution was added with a mixture of TES buffer and phenol, and was vigorously shook for five minute in an ice bath, and the supernatant was collected by centrifugation. The supernatant was added twice volume of cold ethanol, and resulting crude precipitate was collected as crude chromosomal DNA. The crude chromosomal DNA was dissolved in SSC buffer (pH 7.1), and admixed with 7.5 μg of ribonuclease and 125 μg of proteinase, and incubated 37° C. for one hour. The chromosomal DNA was extracted from the reactant by adding chloroform/isoamylalcohol mixture, then added cold ethanol, and the resulting precipitate containing chromosomal DNA was collected. The purified chromosomal DNA, obtained according to the method described above, was dissolved in SSC buffer (pH 7.1) to give a concentration of about one mg/ml and frozen at −80° C.

Experiment 8-2

Preparation of a Transformant, AGA1

One ml of purified chromosomal DNA solution, prepared by the method in Experiment 8-1, was admixed with about 10 units of a restriction enzyme, Kpn I, and incubated at 37° C. for 30 minutes to digest partially the chromosomal DNA. The resulting DNA fragments were separated by agarose gel electrophoresis, and DNA fragments corresponding to about 4,000 to 8,000 base pairs were collected. A plasmid vector, Bluescript II SK(+), commercialized by Stratagene Cloning System, was completely digested with a restriction enzyme, Kpn I. A recombinant DNA was obtained by ligating 0.5 μg of the digested plasmid vector with about 5 μg of the DNA fragments prepared before by using a "DNA ligation kit", commercialized by Takara Shuzo Co., Ltd., according to the method described in a document attached with the kit. Then, a gene library was prepared by transforming 100 μl portion of the competent cell, "Epicurian Coli XL2-Blue", commercialized by Stratagene Cloning System, with the recombinant DNA by conventional competent cell method. The transformants thus obtained as gene library were inoculated into a fresh agar plate medium (pH 7.0) containing 10 g/L of tryptone, 5 g/L of yeast extract, 5 g/L of sodium chloride, 100 mg/L of ampicillin sodium salt, and 50 mg/L of 5-bromo-4-chloro-3-indolyl-β-galactoside, and incubated at 37° C. for 24 hours. About six thousands white colonies grown on the plate were transferred to and fixed on a nylon membrane, "Hybond-N+", commercialized by Amasham Bioscience K. K. An oligonucleotide having a nucleotide sequence of "5'-CARGARTGGAAYYTNACNGGNGAYC-CNTGGAC-3'" was chemically synthesized on the bases of an amino acid sequence of first to eleventh of SEQ ID NO: 27, which disclosed by the method in Experiment 5-4. A synthetic DNA (probe 1) was obtained by labeling the oligonucleotide with radioisotope using [γ-$^{32}$P]ATP and T4 polynucleotide kinase according to the conventional method. Subsequently, two types of transformant showing remarkable hybridization with probe 1 were selected from the colonies fixed on the nylon membrane obtained before, using conventional colony hybridization. The recombinant DNAs were collected from these two types of transformant by conventional method. On the other hand, probe 2 having the nucleotide sequence of "5'-TGGACNCARCCN-GARGCNGGNGCNGTNTTGCA-3'" was chemically synthesized based on a amino acid sequence of sixth to sixteenth of SEQ ID NO: 29 and labeled with radioisotope in the same manner. The recombinant DNAs obtained and probe 2 were used for conventional southern-hybridization, and a recombinant DNA showing a remarkable hybridization with probe 2 was selected. A transformant thus selected was named "AGA1".

Experiment 8-3

Analysis of DNA Sequence

Figure 19:
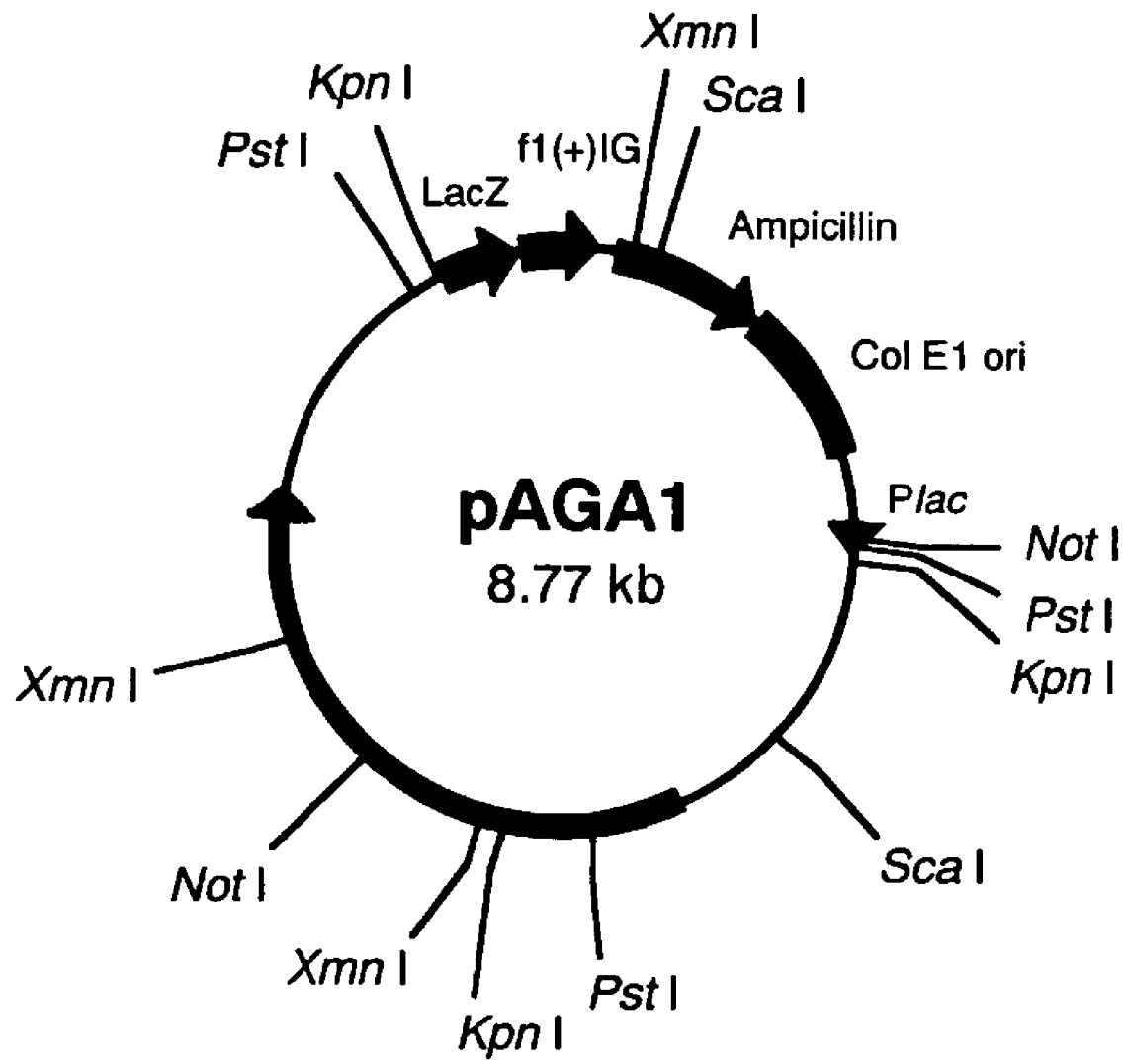
FIG. 19 shows a restriction enzyme map of a recombinant DNA, pAGA1, of the present invention. In the figure, a section indicated with a black bold line is a DNA encoding a polypeptide having α-isomaltosyl-transferring enzyme activity from a microorganism of *Arthrobacter globiformis* A19.

According to the conventional method, the transformant, AGA1, obtained by the method in Experiment 8-2, was inoculated into L-broth medium (pH 7.0) containing 100 µg/ml of ampicillin sodium salt, and cultured under rotary-shaking conditions at 37° C. for 24 hours. After the completion of the culture, cells were collected by centrifugation, and the recombinant DNA was extracted from the cells by conventional alkaline-SDS method. When the nucleotide sequence of the recombinant DNA was analyzed by conventional dideoxy method, it was revealed that the recombinant DNA contained a DNA having the nucleotide sequence of SEQ ID NO: 32, 5,811 base pairs, which originated from *Arthrobacter globiformis* A19. In the recombinant DNA, as shown in FIG. 19, the DNA was ligated at downstream of recognition site of a restriction enzyme, Kpn I. The amino acid sequence deduced from the nucleotide sequence is as shown in parallel in SEQ ID NO: 32. The amino acid sequence was compared with amino acid sequences of polypeptide of the present invention, i.e., the N-terminal amino acid sequence of SEQ ID NO: 26 disclosed by the method in Experiment 5-1 and the internal partial amino acid sequences of SEQ ID NOs:27 to 31 disclosed by the method in Experiment 5-4. An amino acid sequence of SEQ ID NO: 26 was completely identical with that of 37th to 49th of the amino acid sequence shown in parallel in SEQ ID NO: 32. Amino acid sequences of SEQ ID NOs: 27, 28, 29, 30, and 31 were completely identical with those of 227th to 239th, 345th to 374th, 401st to 430th, 89th to 115th, and 641st to 667th of the amino acid sequence shown in parallel in SEQ ID NO: 32, respectively. Since the nucleotide sequence of 4,550th to 4,552nd of SEQ ID NO: 32 encodes a codon for terminating the translation (stop codon, 5'-TGA-3'), it is revealed that C-terminal amino acid of the polypeptide of the present invention is phenylalanine (965th amino acid of the amino acid sequence shown in parallel in SEQ ID NO: 32).

These results indicate that the polypeptide of the present invention contains the amino acid sequence of SEQ ID NO: 3, and that the polypeptide is encoded by the DNA having the nucleotide sequence of SEQ ID NO: 6 in the case of *Arthrobacter globiformis* A19 (FERM BP-7590). An amino acid sequence of the first to 36th of that showing in parallel in SEQ ID NO: 32 was presumed to be a secretion signal sequence of the polypeptide. According to the results described above, it was revealed that the precursor peptide of the polypeptide before secretion had the amino acid sequence shown in parallel in SEQ ID NO: 32, and the amino acid sequence was encoded by the nucleotide sequence of SEQ ID NO: 32. The recombinant DNA prepared and confirmed the nucleotide sequence as described above was named "pAGA1".

EXPERIMENT 9

Production of Polypeptides by Transformants of the Present Invention

Experiment 9-1

A Transformant, BGC2

A liquid culture medium consisting 5 g/L of "PINE-DEX #4", a partial starch hydrolyzate, 20 g/L of polypeptone, 20 g/L of yeast extract, 1 g/L of sodium phosphate dodecahydrate, and water was placed in a 500-ml Erlenmeyer flask in an amount of 100 ml, sterilized by autoclaving at 121° C. for 15 minutes, and cooled. Then, the liquid medium was sterilely set to pH 7.0, and sterilely admixed with 10 mg of ampicillin sodium salt. A transformant, BGC2, obtained by the method in Experiment 6-2, was inoculated into the above liquid medium, and cultured at 27° C. and for 48 hours under aeration-agitation conditions. To investigate the location of the polypeptide in the culture, cells and supernatant were separately collected by conventional centrifugation. In the case of the cells, whole-cell extract, obtained by ultrasonic disruption, and periplasmic extract, obtained by osmotic shock procedure were prepared separately. In the case of ultrasonic disruption, cells were suspended in 10 mM sodium phosphate buffer (pH 7.0), and then disrupted in an ice bath using a ultrasonic homogenizer, "model UH-600", commercialized by MST Corporation, Aichi, Japan, to extract whole-cell fraction. In the case of osmotic shock procedure, cells were washed with 10 mM Tris-HCl buffer (pH 7.3) containing 30 mM sodium chloride, and the washed cells were suspended in 33 mM Tris-HCl buffer (pH 7.3) containing 200 g/L of sucrose and 1 mM EDTA, shook at 27° C. for 20 minutes, and then centrifuged to collect the cells. Subsequently, the cells were suspended in 0.5 mM magnesium chloride solution pre-cooled at about 4° C., and shaken in an ice bath for 20 minutes to extract periplasmic fraction. After centrifuging, the resulting supernatant was collected as periplasmic extract.

α-Isomaltosylglucosaccharide-forming enzyme activities of culture supernatant, whole-cell extract and periplasmic extract, prepared as described above, were assayed, and those values were expressed in terms of the activities/ml-culture, respectively. The results are shown in Table 12.

TABLE 12

| Sample | α-isomaltosylglucosaccharide-forming enzyme activity (units/ml-culture) |
|---|---|
| Culture supernatant | 0.0 |
| Whole-cell extract | 1.1 |
| Periplasmic extract | 1.0 |

As evident from the results in Table 12, it was revealed that the transformant, BGC2, produced the polypeptide of the present invention intracellularly, and secreted most of it in periplasmic fraction. As the first control experiment, *E. coli* XL2-Blue was cultured with the same conditions in the case of the transformant described above except for the addition of ampicillin, and a supernatant and a cell-extract were prepared from the culture. As the second control experiment, *Bacillus globisporus* C11, was cultured with the same conditions in the case of the transformant described above except for the addition of ampicillin, and a supernatant and a cell-extract were prepared from the culture. In the first control experiment, the enzyme activity was not detected from either of the culture supernatant and the cell-extract. In the second control experiment, the enzyme activity of the culture supernatant and the cell-extract were about 0.37 units and about 0.02 units, respectively. Compared with the case of the transformant BGC2, the enzyme activity was evidently low-level values.

The periplasmic fraction was further purified by salting out, dialysis and successive column chromatographies on "SEPABEADS FP-DA13" gel, "SEPHACRYL HR S-200" gel, and "BTJTYL-TOYOPEARL 650M" gel according to the methods described in Experiment 1, and the purified polypeptide was analyzed according to the methods described in Experiment 1. As the results, the molecular weight was about 137,000±2,000 daltons by SDS-polyacrylamide gel electrophoresis, the isoelectric point was about 5.2±0.5 by polyacrylamide gel isoelectrophoresis, the optimum temperature of α-isomaltosylglucosaccharide-transferring enzyme activity was about 45° C. (in the absence of $Ca^{2+}$) and about 50° C. (in the presence of $Ca^{2+}$), the optimum pH was about 6.0, the thermal stability was up to about 40° C. (in the absence of $Ca^{2+}$) and about 50° C. (in the presence of $Ca^{2+}$), and the pH stability was in the range of about pH 5.0 to about 10.0. These physicochemical properties were practically identical to those of the polypeptide having α-isomaltosylglucosaccharide-forming enzyme activity prepared in Experiment 1.

Experiment 9-2

A Transformant, BGN2

A liquid culture medium consisting 5 g/L of "PINE-DEX #4", a partial starch hydrolyzate, 20 g/L of polypeptone, 20 g/L of yeast extract, 1 g/L of sodium phosphate dodecahydrate, and water was placed in a 500-ml Erlenmeyer flask in a amount of 100 ml, sterilized by autoclaving at 121° C. for 15 minutes, and cooled. Then, the liquid medium was sterilely set to pH 7.0, and sterilely admixed with 10 mg of ampicillin sodium salt. A transformant, BGN2, obtained by the method in Experiment 7-2, was inoculated into the above liquid medium, and cultured at 27° C. and for 48 hours under aeration-agitation conditions. To investigate the location of the polypeptide in the culture, culture supernatant, whole-cell extract, and periplasmic extract were separately prepared according to the method in Experiment 9-1. α-Isomaltosylglucosaccharide-forming enzyme activities of culture supernatant, whole-cell extract and periplasmic extract were assayed, and those values were expressed in terms of the activities/ml-culture, respectively. The results are shown in Table 13.

TABLE 13

| Sample | α-isomaltosylglucosaccharide-forming enzyme activity (units/ml-culture) |
| --- | --- |
| Culture supernatant | 0.54 |
| Whole-cell extract | 0.91 |
| Periplasmic extract | 0.85 |

As evident from the results in Table 13, it was revealed that the transformant, BGN2, produced the polypeptide of the present invention intracellularly, and secreted most of it in periplasmic fraction. As the first control experiment, *E. coli* XL2-Blue was cultured with the same conditions in the case of the transformant described above except for the addition of ampicillin, and a supernatant and a cell-extract were prepared from the culture. As the second control experiment, *Bacillus globisporus* N75, was cultured with the same conditions in the case of the transformant described above except for the addition of ampicillin, and a supernatant and a cell-extract were prepared from the culture. In the first control experiment, the enzyme activity was not detected from either of the culture supernatant and the cell-extract. In the second control experiment, the enzyme activity of the culture supernatant and the cell-extract were about 0.21 units and about 0.01 units, respectively. Compared with the case of the transformant BGN2, the enzyme activity was evidently low-level values.

The periplasmic fraction was further purified by salting out, dialysis and successive column chromatographies on "SEPABEADS FP-DA13" gel, "SEPHACRYL HR S-200" gel, and "BUTYL-TOYOPEARL 650M" gel according to the methods described in Experiment 2, and the purified polypeptide was analyzed according to the methods described in Experiment 2. As the results, the molecular weight was about 136,000±2,000 daltons by SDS-polyacrylamide gel electrophoresis, the isoelectric point was about 7.3±0.5 by polyacrylamide gel isoelectrophoresis, the optimum temperature of α-isomaltosylglucosaccharide-transferring enzyme activity was about 50° C. (in the absence of $Ca^{2+}$) and about 55° C. (in the presence of $Ca^{2+}$), the optimum pH was about 6.0, the thermal stability was up to about 45° C. (in the absence of $Ca^{2+}$) and about 50° C. (in the presence of $Ca^{2+}$), and the pH stability was in the range of about pH 5.0 to about 9.0. These physicochemicalL properties were practically identical to those of the polypeptide having α-isomaltosylglucosaccharide-forming enzyme activity prepared in Experiment 2.

Experiment 9-3

A Transformant, AGA1

A liquid culture medium consisting 5 g/L of "PINE-DEX #4", a partial starch hydrolyzate, 20. g/L of polypeptone, 20 g/L of yeast extract, 1 g/L of sodium phosphate dodecahydrate, and water was placed in a 500-ml Erlenmeyer flask in a amount of 100 ml, sterilized by autoclaving at 121° C. for 15 minutes, and cooled. Then, the liquid medium was sterilely set to pH 7.0, and sterilely admixed with 10 mg of ampicillin sodium salt. A transformant, AGA1, obtained by the method in Experiment 8-2, was inoculated into the above liquid medium, and cultured at 27° C. and for 48 hours under aeration-agitation conditions. To investigate the location of the polypeptide in the culture, culture supernatant, whole-cell extract, and periplasmic extract were separately prepared according to the method in Experiment 9-1. α-Isomaltosylglucosaccharide-forming enzyme activities of culture supernatant, whole-cell extract and periplasmic extract were assayed, and those values were expressed in terms of the activities/ml-culture, respectively. The results are shown in Table 14.

TABLE 14

| Sample | α-isomaltosylglucosaccharide-forming enzyme activity (units/ml-culture) |
| --- | --- |
| Culture supernatant | 0.51 |
| Whole-cell extract | 2.5 |
| Periplasmic extract | 2.4 |

As evident from the results in Table 14, it was revealed that the transformant, AGA1, produced the polypeptide of the present invention intracellularly, and secreted most of it in periplasmic fraction. As the first control experiment, *E. coli* XL2-Blue was cultured with the same conditions in the case of the transformant described above except for the addition of ampicillin, and a supernatant and a cell-extract were prepared from the culture. As the second control experiment, *Arthrobacter globiformis* A19, was cultured with the same conditions in the case of the transformant described above except for the addition of ampicillin, and a supernatant and a cell-extract were prepared from the culture. In the first control experiment, the enzyme activity was not detected from either of the culture supernatant and the cell-extract. In the second control experiment, the enzyme activity of the culture supernatant and the cell-extract were about 0.33 units and about 0.01 units, respectively. Compared with the case of the transformant AGA1, the enzyme activity was evidently low-level values.

The periplasmic fraction was further purified by salting out, dialysis and successive column chromatographies on "DEAE-TOYOPEARL 650M" gel and "SEPHACRYL HR S-200" gel according to the methods described in Experiment 3, and the purified polypeptide was analyzed according to the methods described in Experiment 3. As the results, the molecular weight was about 94,000±2,000 daltons by SDS-polyacrylamide gel electrophoresis, the isoelectric point was about 4.3±0.5 by polyacrylamide gel isoelectrophoresis, the optimum temperature of α-isomaltosylglucosaccharide-transferring enzyme activity was about 60° C. (in the absence of $Ca^{2+}$) and about 65° C. (in the presence of $Ca^{2+}$), the optimum pH was about 8.4, the thermal stability was up to about 55° C. (in the absence of $Ca^{2+}$) and about 60° C. (in the presence of $Ca^{2+}$), and the pH stability was in the range of about pH 5.0 to about 9.0. These physicochemical properties were practically identical to those of the polypeptide having α-isomaltosylglucosaccharide-forming enzyme activity prepared in Experiment 3.

From the results described above, it is revealed that the polypeptide of the present invention can be produced by recombinant DNA techniques, and that the productivity of the polypeptide is remarkably increased.

The following examples concretely explain the production processes for the polypeptide of the present invention, cyclotetrasaccharide obtainable thereby, and saccharides comprising the same:

EXAMPLE 1

Production of the Polypeptide of the Present Invention

A liquid medium containing 5 g/L of "PINE-DEX #4", a partial starch hydrolyzate, 20 g/L of polypeptorie, 20 g/L of yeast extract, 1 g/L of sodium phosphate, and water was placed in a 500-ml Erlenmeyer flask in an amount of 100 ml, sterilized at 121° C. for 15 minutes, and cooled. Then, the liquid medium was sterilely set to pH 7.0, and admixed with ampicillin sodium salt to give a final concentration of 100 µg/ml. A transformant, BGC2, obtained by the method in Experiment 5-2, was inoculated into the above liquid medium, and cultured at 27° C. and at 230 rpm for 24 hours to obtain the seed culture. Subsequently, about 18 L of a fresh preparation of the same liquid culture medium as used for the above seed culture was placed in a 30-L fermentor, sterilized with the same manner, cooled to 27° C., and then admixed with ampicillin to give a concentration of 50 g/ml, and inoculated with 1%(v/v) of the seed culture, followed by culturing at 27° C. for 48 hours under aeration condition. After collecting cells in the culture by centrifugation, suspending the cells in 10 mM sodium phosphate buffer (pH 7.0), disrupting the cells by ultrasonication, and removing the cell-debris by centrifugation, supernatant was obtained. About 1,100 units/L-culture of enzyme activity was detected by the assay of the activity in the resulting supernatant. About 70 ml of enzyme solution containing about 61 units/ml of the polypeptide of the present invention, whose specific activity is about 13.5 units/mg-protein, was obtained by purifying the supernatant according to the method described in Experiment 1.

EXAMPLE 2

Production of the Polypeptide of the Present Invention

A liquid medium containing 5 g/L of "PINE-DEX #4", a partial starch hydrolyzate, 20 g/L of polypeptone, 20 g/L of yeast extract, 1 g/L of sodium phosphate, and water was placed in a 500-ml Erlenmeyer flask in an amount of 100 ml, sterilized at 121° C. for 15 minutes, and cooled. Then, the liquid medium was sterilely set to pH 7.0, and admixed with ampicillin sodium salt to give a final concentration of 100 µg/ml. A transformant, BGN2, obtained by the method in Experiment 6-2, was inoculated into the above liquid medium, and cultured at 27° C. and at 230 rpm for 24 hours to obtain the seed culture. Subsequently, about 18 L of a fresh preparation of the same liquid culture medium as used above seed culture was placed in a 30-L ferment6r, sterilized with the same manner, cooled to 27° C., and then admixed with ampicillin to give a concentration of 50 µg/ml, and inoculated with 1%(v/v) of the seed culture, followed by culturing at 27° C. for 48 hours under aeration condition. Culture supernatant was obtained by centrifuging the resultant culture. About 750 units/L-culture of enzyme activity was detected by the assay of the activity in the resulting culture supernatant. About 75 ml of enzyme solution containing about 72 units/ml of the polypeptide of the present invention, whose specific activity is about 12.6 units/mg-protein, was obtained by purifying the supernatant according to the method described in Experiment 2.

EXAMPLE 3

Production of a Syrupy Composition Containing Cyclotetrasaccharide

A tapioca starch was prepared into an about 25% starch suspension, admixed with 0.2%/g-starch, d.s.b., of "NEOSPITASE", an α-amylase commercialized by Nagase Biochemicals, Ltd., Kyoto, Japan, and then heated at 85–90° C. for about 25 minutes. After autoclaving at 120° C. for 20 minutes, the reaction mixture was cooled to about 35° C. to obtain a liquefied-solution with a DE about four. The liquefied solution was admixed with2.2 units/g-starch,d.s.b., of the polypeptide of the present invention, obtained in Example 1, 6.6 units/g-starch, d.s.b., of α-isomaltosyl-transferring enzyme obtained by the method in Experiment 1-4, and 10 units/g-starch, d.s.b., of cyclomaltodextrin glucanotransferase commercialized by Hayashibara Biochemical Laboratories Inc., followed by the enzymatic reaction at pH 6.0 and at 35° C. for 48 hours. After heating to 95° C. for 30 minutes, the reaction mixture was adjusted at pH 5.0 and 50° C., admixed with 300 units/g-starch, d.s.b., of "TRANS-GLUCOSIDASE L AMANO™", an α-glucosidase commercialized by Amano Pharmaceutical Co., Ltd., Aichi, Japan, followed by the enzymatic reaction for 24 hours. Further the reaction mixture was mixed with 30 units/g-starch, d.s.b., of "GLUCOZYME", a glucoamylase preparation commercialized by Nagase Biochemicals, Ltd., Kyoto, Japan, and then enzymatically reacted for 17 hours. The reaction mixture was heated to 95° C. and kept for 30 minute, and then cooled and filtered to obtain a filtrate. According to the conventional manner, the resulting filtrate was decolored with activated charcoal, desalted and purified with ion exchangers in H- and OH-forms, and then concentrated into a 60% cyclotetrasaccharide syrup in a yield of about 90% to the material starch, d.s.b.

Since the product contains, on a dry solid basis, 36.4% glucose, 58.1% cyclotetrasaccharide, and 3.5% of other saccharides and has a mild sweetness, an adequate viscosity, moisture-retaining ability, clathrating ability, it can be advantageously used in a variety of compositions such as food products, cosmetics, and pharmaceuticals as a sweetener, taste-improving agent, quality-improving agent, syneresis-preventing agent, stabilizer, discoloration-preventing agent, filler, and clathrating agent.

EXAMPLE 4

Production of a Crystalline Powder of Cyclotetrasaccharide

A corn starch was prepared into a 25% starch suspension, admixed with calcium carbonate to give a final concentration of 0.1%, adjusted to pH 6.5, and admixed with 0.3%/g-starch of "THERMAMYL 60 L", an α-amylase commercialized by Novo Industries A/S, Copenhagen, Denmark, and then heated at 95° C. for 15 minutes. After autoclaving at 120° C. for 20 minutes, the reaction mixture was cooled to 35° C. to obtain a liquefied solution with a DE of about four. To the liquefied solution was added 2.5 units/g-starch, d.s.b., of the polypeptide of the present invention, obtained in Example 1, 7.0 units/g-starch, d.s.b., of α-isomaltosyl-transferring enzyme obtained by the method in Experiment 1-4, and 10 units/g-starch, d.s.b., of cyclomaltodextrin glucanotransferase commercialized by Hayashibara Biochemical Laboratories Inc., followed by the enzymatic reaction at pH 6.0 and 35° C. for 48 hours. After heating to 95° C. for 30 minutes, the reaction mixture was adjusted at pH 5.0, and 50° C., admixed with 300 units/g-starch, d.s.b., of "TRANSGLUCOSIDASE L AMANO™", an α-glucosidase commercialized by Amano Pharmaceutical Co., Ltd., Aichi, Japan, followed by the enzymatic reaction for 24 hours. Further the reaction mixture was mixed with 30 units/g-starch, d.s.b., of "GLUCOZYME", a glucoamylase preparation commercialized by Nagase Biochemicals, Ltd., Kyoto, Japan, and then enzymatically reacted for 24 hours. The reaction mixture was heated to 95° C. and kept for 30 minute, and then cooled and filtered to obtain a filtrate. According to the conventional manner, the resulting filtrate was decolored with activated charcoal, desalted and purified with ion exchangers in H- and OH-forms, and then concentrated into a 60% syrup containing, on a dry solid basis, 34.2% glucose, 62.7% cyclotetrasaccharide, and 3.1% of other saccharides.

The resulting saccharide solution was subjected to a column chromatography using "AMBERLITE CR-1310 (Na-form)", a strong acid cation-exchanger resin commercialized by Japan Organo Co., Ltd., Tokyo, Japan. The resin was packed into four-jacketed stainless steel columns having a diameter of 5.4 cm, which were then cascaded in series to give a total gel bed depth of 20 m. Under the conditions of keeping the inner column temperature at 60° C., the saccharide solution was fed to the columns in a volume of 5%(v/v) and fractionated by feeding to the columns hot water heated to 60° C. at an SV (space velocity) of 0.13 to obtain high cyclotetrasaccharide content fractions while monitoring the saccharide composition of eluate by HPLC, and then collected the high cyclotetrasaccharide content solution containing about 98%, d.s.b., of cyclotetrasaccharide.

The solution was concentrated to give a concentration of about 70% and then placed in a crystallizer, admixed with about 2% crystalline cyclotetrasaccharide penta- or hexahydrate as seed crystal, and gradually cooled to obtain a massecuite with a crystallinity of about 45%. The massecuite was sprayed from a nozzle equipped on top of drying tower at high pressure of 150 kg/cm$^2$. Simultaneously, hot air heated to 85° C. was being blown down from the upper part of the drying tower, and the resulting crystal powder was collected on a transporting wire conveyor provided on the basement of the tower and gradually moved out of the tower while blowing thereunto a hot air heated to 45° C. The resulting crystalline powder was injected to an aging tower and aged for 10 hours while a hot air was being blown to the contents to complete crystallization and drying to obtain a crystalline powder of cyclotetrasaccharide penta- or hexahydrate in a yield of about 20% to the material starch, d.s.b.

Since the product has a relatively low reducibility, does substantially neither cause the amino-carbonyl reaction nor exhibit hygroscopicity, and has a satisfactory handleability, mild low sweetness, adequate viscosity, moisture-retaining ability, clathrating ability, and substantially non-digestibility, it can be advantageously used in a variety of compositions such as food products, cosmetics, and pharmaceuticals as a sweetener, low calorie food, taste-improving agent, flavor-improving agent, quality-improving agent, syneresis-preventing agent, stabilizer, filler, clathrating agent, and base for pulverization.

EXAMPLE 5

Production of a Crystalline Powder of Cyclotetrasaccharide

A corn starch was prepared into a 30% starch suspension, admixed with calcium carbonate to give a concentration of 0.1%, adjusted to pH 6.5, and admixed with 0.3%/g-starch, d.s.b., of "THERMAMYL 60 L", an α-amylase commercialized by Novo Industries A/S, Copenhagen, Denmark, and then heated at 95° C. for 15 minutes. After autoclaving at 120° C. for 20 minutes, the reaction mixture was cooled to 51° C. to obtain a liquefied solution with a DE of about four. To the liquefied solution was added 2.4 units/g-starch, d.s.b., of the polypeptide of the present invention, obtained in Example 2, 8.0 units/g-starch, d.s.b., of α-isomaltosyl-transferring enzyme obtained by the method in Experiment 2-4, and 3 units/g-starch, d.s.b., of cyclomaltodextrin glucanotransferase commercialized by Hayashibara Biochemical Laboratories Inc., followed by the enzymatic reaction at pH 5.5 and 51° C. for 48 hours. After heating to 95° C. for 30 minutes, the reaction mixture was adjusted to pH 5.0, and 50° C., admixed with 300 units/g-starch of "TRANSGLUCOSIDASE L AMANOυ", an α-glucosidase commercialized by Amano Pharmaceutical Co., Ltd., Aichi, Japan, followed by the enzymatic reaction for 24 hours. Further the reaction mixture was mixed with 30 units/g-starch, d.s.b., of "GLUCOZYME", a glucoamylase preparation commercialized by Nagase Biochemicals, Ltd., Kyoto, Japan, and then reacted for 17 hours. The reaction mixture was heated to 95° C. and kept for 30 minute, and then cooled and filtered to obtain a filtrate. According to the conventional manner, the resulting filtrate was decolored with activated charcoal, desalted and purified with ion exchangers in H- and OH-forms, and then concentrated into a 60% syrup containing, on a dry solid basis, 46.8% glucose, 44.0% cyclotetrasaccharide, and 9.8% of other saccharides. In order to increase the content of cyclotetrasaccharide, the resulting saccharide syrup was fractionated by a column chromatography using a strong acid cation-exchanger resin described in Example 5, and then collected the high cyclotetrasaccharide content fractions. After purifying, concentrating, and spray-drying, a powdery product containing cyclotetrasaccharide was obtained in a yield of about 45% to the material starch, d.s.b.

Since the product contains, on a dry solid basis, 3.7% glucose, 80.5% cyclotetrasaccharide, and 15.8% of other saccharides and has a mild sweetness, an adequate viscosity, moisture-retaining ability, clathrating ability, it can be advantageously used in a variety of compositions such as food products, cosmetics, and pharmaceuticals as a sweetener, taste-improving agent, quality-improving agent, syneresis-preventing agent, stabilizer, discoloration-preventing agent, filler, clathrating agent, and base for pulverization.

The present invention, having these outstanding functions and effects, is a significantly important invention that greatly contributes to this art.

The invention claimed is:

1. An isolated DNA, which encodes a polypeptide comprising the amino acid sequence of SEQ ID NO:2; wherein said polypeptide has an enzymatic activity of forming a saccharide with a glucose polymerization degree of 3 or higher and bearing both the α-1,6 glucosidic linkage as a linkage at the non-reducing end and the α-1,4 glucosidic linkage other than the linkage at the non-reducing end from a saccharide with a glucose polymerization degree of 2 or higher and bearing the α-1,4 glucosidic linkage as a linkage at the non-reducing end by an α-glucosyl transferring reaction.

2. The isolated DNA of claim 1, which comprises the nucleotide sequence of SEQ ID NO;5 or the full length complement thereof.

3. The isolated DNA of claim 1, which is obtained by replacing one or more nucleotides of SEQ ID NO:5with other nucleotides based on the genetic code degeneracy wherein the amino acid sequence of SEQ ID NO: 2 remains unchanged.

4. The isolated DNA of claim 1, which is isolated from a microorganism of the genus *Bacillus*.

5. An isolated replicable recombinant DNA, which comprises the DNA of claim 1 and an autonomously replicable vector.

6. The replicable recombinant DNA of claim 5, wherein said autonomously-replicable vector is a plasmid vector, Bluescript IT SK(+).

7. An isolated host cell tramsformed with the recombinant DNA of claim 5 or 6.

8. The isolated host cell of claim 7, wherein said host is a microorganism of the species *Escherichia coil*.

9. A process for producing a polypeptide having an enzymatic activity of forming a saccharide with a glucose polymerization degree of 3 or higher and bearing both the α-1,6 glucosidic linkage as a linkage at the non-reducing end and the α-1,4 glucosidic linkage other than the linkage at the non-reducing end from a saccharide with a glucose polymerization degree of 2 or higher and bearing the α-1,4 glucosidic linkage as a linkage at the non-reducing end by α-glucosyl transferring reaction, which comprises the steps of culturing the isolated transformed host cell of claim 7 to produce the polypeptide and collecting the polypeptide from the resulting culture.

10. The process of claim 9, wherein the polypeptide is collected by one or more techniques selected from the group consisting of centrifuge, filtration, concentration, salting out, dialysis, concentration, separatory precipitation, ion-exchange chromatography, gel filtration chromatography, hydrophobic chromatography, affinity chromatography, gel electrophoresis, and isoelectric focusing.

* * * * *